(12) United States Patent
Li et al.

(10) Patent No.: US 12,091,552 B2
(45) Date of Patent: Sep. 17, 2024

(54) REACTIVE DYES AND PREPARATION METHODS THEREOF

(71) Applicant: NANTONG UNIVERSITY, Jiangsu (CN)

(72) Inventors: Min Li, Nantong (CN); Wujun Ma, Nantong (CN); Jialiang Zhou, Nantong (CN); Wenlin Qu, Nantong (CN); Ting Ding, Nantong (CN); Lifen Mao, Nantong (CN); Shiyu Li, Nantong (CN)

(73) Assignee: NANTONG UNIVERSITY, Nantong (CN)

( * ) Notice: Subject to any disclaimer, the term of this patent is extended or adjusted under 35 U.S.C. 154(b) by 0 days.

(21) Appl. No.: 18/366,655

(22) Filed: Aug. 7, 2023

(65) Prior Publication Data

US 2024/0084144 A1 Mar. 14, 2024

(30) Foreign Application Priority Data

Aug. 11, 2022 (CN) .......................... 202210961845.1
Aug. 11, 2022 (CN) .......................... 202210962830.7
Aug. 29, 2022 (CN) .......................... 202211047206.0

(51) Int. Cl.
*C09B 61/00* (2006.01)
*C09B 33/048* (2006.01)
(Continued)

(52) U.S. Cl.
CPC ............ *C09B 62/01* (2013.01); *C09B 33/048* (2013.01); *D06P 1/06* (2013.01); *G01N 33/52* (2013.01)

(58) Field of Classification Search
CPC ......... C09B 62/01; C09B 33/048; D06P 1/06; G01N 33/52
(Continued)

(56) References Cited

U.S. PATENT DOCUMENTS 5,364,416 A * 11/1994 Schwarz ............. C09B 67/0048 8/549
6,444,794 B1 * 9/2002 Dannheim .......... C09B 62/4403 8/549

(Continued)

FOREIGN PATENT DOCUMENTS

CN 104164229 A 11/2014
CN 104277492 A 1/2015
(Continued)

OTHER PUBLICATIONS

Qu, Jiangang et al., Study on the Factors of Color Fastness to the Perspiration and Light of Reactive Azo-Dyes, Textile Auxiliaries, 31(1): 24-27, 2014.
(Continued)

*Primary Examiner* — Eisa B Elhilo
(74) *Attorney, Agent, or Firm* — Runzhi Lai

(57) ABSTRACT

Disclosed are reactive dyes and preparation methods thereof. The reactive dye may be prepared using heterocyclic primary amine as a diazo component, 4,4'-diamino-2,2'-stilbenedisulfonic acid, s-triazine, or ethylenediamine as a bridging group, and a dimonochlortriazine group as an active group. The color-changing compound is covalently bonded into the fiber chemical structure by nucleophilic substitution reaction between monochlorotriazine and the hydroxyl group in a textile structure, and the size of the conjugated system and the range of electron delocalization of the dye are changed by a reversible isomerization reaction of the hydroxyl group adjacent to the diazo group and the diazo group under different pH regulations. Moreover, the
(Continued)

dye has a double color changing structure, which improves the capability of the dye combined with —H/—OH. The pH value range that can cause color changes in the dye is effectively expanded to include weak alkali, weak acid or even neutral conditions.

7 Claims, 28 Drawing Sheets

(51) Int. Cl.
 *C09B 62/01* (2006.01)
 *D06P 1/06* (2006.01)
 *G01N 33/52* (2006.01)
(58) Field of Classification Search
 USPC .................................................. 8/549
 See application file for complete search history.

(56) References Cited

U.S. PATENT DOCUMENTS

| | | | | |
|---|---|---|---|---|
| 6,447,554 | B1* | 9/2002 | Brock | A61K 8/4926 8/549 |
| 7,108,727 | B2* | 9/2006 | Reichelt | A61K 8/418 8/549 |
| 2005/0034253 | A1* | 2/2005 | Meier | C09B 67/0047 8/543 |
| 2008/0216256 | A1* | 9/2008 | Freeman | C09B 62/043 8/549 |
| 2008/0257208 | A1* | 10/2008 | Ebenezer | D06P 5/30 8/549 |
| 2011/0173764 | A1 | 7/2011 | Ehrenberg | |
| 2020/0231819 | A1* | 7/2020 | Gao | C09B 62/513 |

FOREIGN PATENT DOCUMENTS

| | | | | |
|---|---|---|---|---|
| CN | 105440728 | A | | 3/2016 |
| CN | 105273437 | B | * | 5/2017 ............ D06P 1/382 |
| CN | 107722667 | A | | 2/2018 |
| CN | 108084732 | A | | 5/2018 |
| CN | 109825108 | A | | 5/2019 |
| CN | 111073338 | A | * | 4/2020 ......... C09B 67/0072 |
| CN | 112341838 | A | * | 2/2021 ........... C09D 11/328 |
| CN | 112625460 | A | | 4/2021 |
| CN | 112679984 | A | * | 4/2021 ............... D06P 3/66 |
| CN | 112940530 | A | | 6/2021 |
| CN | 113683901 | A | | 11/2021 |
| CN | 113683903 | A | | 11/2021 |
| GB | 1318879 | A | | 5/1973 |
| GB | 1426382 | A | | 2/1976 |
| GB | 1569246 | A | | 6/1980 |
| JP | H08176453 | A | | 7/1996 |
| WO | 2013018071 | A2 | | 2/2013 |

OTHER PUBLICATIONS

Yu, Guangtao, Improving Color Fastness of the Reactive Dyeings, Print and Dye, 7: 21-23, 2006.
First Office Action in Chinese Application No. 202210961845.1 mailed on Jun. 27, 2023, 13 pages.
Notification to Grant Patent Right for Invention in Chinese Application No. 202210961845.1 mailed on Aug. 29, 2023, 2 pages.

* cited by examiner

REACTIVE DYES AND PREPARATION METHODS THEREOF

CROSS-REFERENCE TO RELATED APPLICATIONS

This application claims priority of the Chinese Patent Application No. 202211047206.0, filed on Aug. 29, 2022, the Chinese Patent Application No. 202210961845.1, filed on Aug. 11, 2022, and the Chinese Patent Application No. 202210962830.7, filed on Aug. 11, 2022, the entire contents of each of which are hereby incorporated by reference.

TECHNICAL FIELD

The present disclosure relates to the technical field of fine chemicals, and in particular to reactive dyes and preparation methods thereof.

BACKGROUND pH-sensitive color-changing materials belong to the category of ionic color-changing materials, and their color changes in response to variations in pH levels. Color-changing textiles are prepared by applying pH-sensitive reactive dyes, e.g., compounds with pH indication properties, to fabrics through dyeing, coating or printing processes. These textiles have diverse applications, such as protective clothing for warning against corrosive gases, color-changing bandages for indicating wound healing, and agricultural textiles for measuring soil pH levels. However, the current pH-sensitive reactive dyes face issues, including a low dyeing rate on cotton fabrics, resulting in a low color yield. Additionally, the color-changing effect is only observable under strong acidic or strong alkaline conditions.

Therefore, it is desirable to prepare a pH-sensitive reactive dye that can establish a stable covalent bonding reaction with textiles while exhibiting color changes under weak alkali, weak acid, or even neutral conditions.

SUMMARY

One of the embodiments of the present disclosure provides a reactive dye. The reactive dye is represented by formula (1):

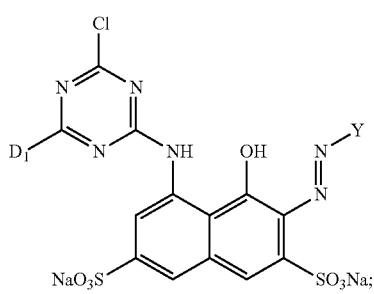

formula (1)

In some embodiments, Y in the formula (1) may be represented by formula (2), formula (3), formula (4), formula (5), or formula (6):

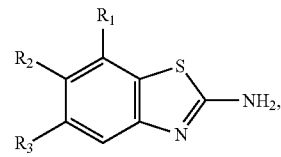

formula (2)

where $R_1$, $R_2$ and $R_3$ in the formula (2) may be independently —H, —NO$_2$, —OCH$_3$, or halogen;

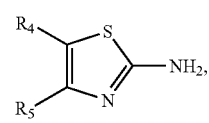

formula (3)

where $R_4$ and $R_5$ in formula (3) may be independently —H or —NO$_2$;

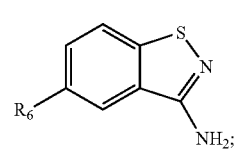

formula (4)

where $R_6$ in the formula (4) may be independently —H or —NO$_2$;

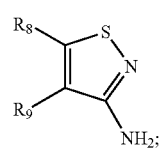

formula (5)

where $R_7$ and $R_8$ in the formula (5) may be independently —H or —NO$_2$;

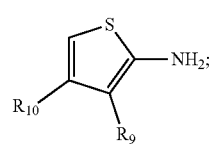

formula (6)

where $R_9$ and $R_{10}$ in the formula (6) may be independently —H, —NO$_2$, —CN, or halogen.

In some embodiments, D1 in the formula (1) is represented by formula (A):

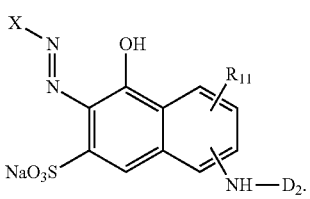

formula (A)

In some embodiments, X in the formula (A) may be one of the formula (2), the formula (3), the formula (4), the formula (5), or the formula (6), $R_{11}$ may be —H or —SO$_3$Na, and D2 may be —H or a formula (B);

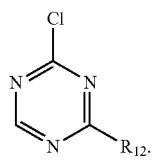

formula (B)

In some embodiments, $R_{12}$ in the formula (B) may be formula (B1) or formula (B2):

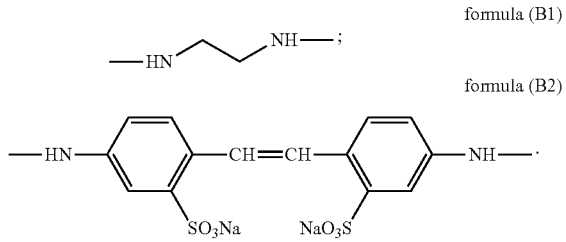

formula (B1)

formula (B2)

One of the embodiments of the present disclosure provides a preparation method of a reactive dye. In some embodiments, the preparation method may include:
(i) Primary Condensation Reaction
   adding cyanuric chloride and sodium butyl naphthalene sulfonate in an ice-water mixture to obtain a cyanuric chloride solution; adding a parent compound of the reactive dye into water to obtain a parent compound solution of the dye compound; mixing the parent compound solution of the dye compound with the cyanuric chloride solution, and obtaining a primary condensation solution after the reaction is finished; and regulating a pH value of the primary condensation solution to 1.5, then adding potassium chloride to precipitate solid powder, dispersing the precipitated solid powder in absolute ethanol, filtering, and freeze-drying to obtain a primary condensation product;
(ii) Secondary Condensation Reaction
   dissolving the primary condensation product in water to obtain an aqueous solution of the primary condensation product; mixing the aqueous solution of the primary condensation product with the reaction solution, increasing temperature to 30-35° C., regulating the pH to 4.5-5.0, and continuing the reaction at 30-35° C. to obtain a secondary condensation solution, wherein the reaction solution corresponds to the parent compound; regulating the pH value of the secondary condensation solution to 2.0, and then adding potassium chloride to precipitate solid powder; and dispersing the precipitated solid powder in absolute ethanol, filtering, and freeze-drying to obtain a secondary condensation product;
(iii) Diazotization-Coupling Reaction
   dissolving a heterocyclic primary arylamine derivative in acid, adding a diazotization reagent to react, and after the reaction is finished, eliminating excess nitrous acid to obtain a heterocyclic primary arylamine diazonium salt; dissolving the secondary condensation product in water, and slowly adding the heterocyclic primary arylamine diazo salt into the reaction; and after the reaction is finished, obtaining the reactive dye compound after salting out, suction filtration, washing with ethanol and drying.

One of the embodiments of the present disclosure provides a color changing textile. In some embodiments, the color changing textile may be obtained by dyeing a textile with the reactive dye.

One of the embodiments of the present disclosure provides a sweat detection sensor performing sweat detection and sensing using the reactive dye above.

BRIEF DESCRIPTION OF THE DRAWINGS

The present disclosure is further illustrated in terms of exemplary embodiments. These exemplary embodiments are described in detail with reference to the drawings. These examples are non-limiting exemplary embodiments, wherein.

DETAILED DESCRIPTION

Figure 1:
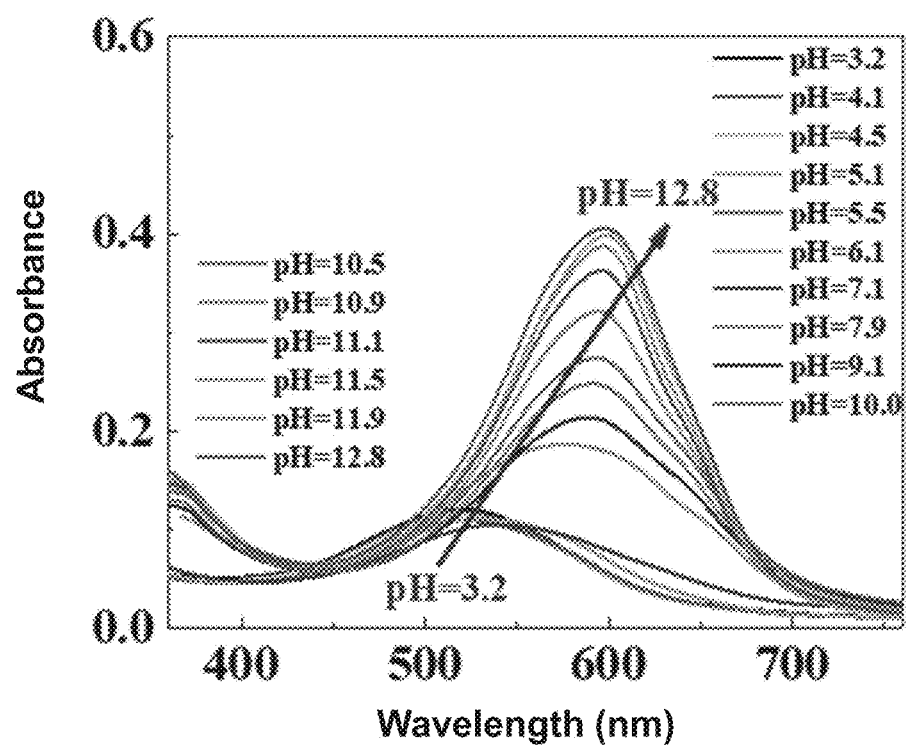
FIG. 1 is a spectrum curve illustrating a dye in Example 1 under different pH conditions (pH=3.2-12.8).

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

As used in the disclosure and the appended claims, the singular forms "a," "an," and "the" include plural referents unless the content clearly dictates otherwise. Generally speaking, the terms "comprise", "comprises", "comprising", "includes", "include" and "including" when used in this specification, specify the presence of stated steps and elements, these steps and elements do not constitute an exclusive list, and the method or the device may also include other steps or elements.

pH-sensitive color-changing fabrics refer to textiles that exhibit color changes as a pH value of the surrounding environment changes. They belong to a branch of ion color-changing materials and can be applied in various fields. Most of the dyes used for pH-sensitive color-changing fabrics are pH indicators or chemically reactive dyes. However, current pH-sensitive color-changing reactive dyes suffer from drawbacks such as a low dyeing rate on cotton fabrics, resulting in a low color yield. Moreover, the color-changing effect is only observable under strong acidic or strong alkaline conditions, making it challenging to distinguish substances (e.g., sweat) under neutral conditions.

In order to solve the problems, the present disclosure provides various reactive dyes, with heterocyclic primary amine as a diazo component, a compound containing a s-triazine active group as a coupling component, and bridging groups with different structures. In some embodiments, the s-triazine active group may include a group with a substituent group. For example, the s-triazine active group may be halogenated s-triazine. In some embodiments, the s-triazine reactive group may be monochloro-s-triazine. In some embodiments, the bridging group may be 4,4'-diamino-2,2'-stilbenedisulfonic acid or s-triazine. In some embodiments, the bridging group may be ethylenediamine. The pH-sensitive color-changing compound of the reactive dye is covalently bonded with a chemical structure of the fiber by nucleophilic substitution reaction between s-triazine and the hydroxyl group in the textile structure. The size of the conjugated system and the range of electron delocalization of the dye are changed by the reversible isomerization reaction between the hydroxyl group adjacent to the diazo group and the diazo group under different pH conditions. This reversible color change mechanism allows for the dye's color to change in response to pH variations. Moreover, the dye of the present disclosure has a double-color-changing structure, increasing the capability of the dye bonding with —H/—OH. The double-color-changing structure refers to a structure having two color changing groups of the dye structure. The color changing group may a group having a conjugated structure. The two color changing groups may be located at two sides of the bridging group and linked to s-triazine. In some embodiments, the double-color-changing structure may include H acid (1-amino-8-hydroxy-3,6-sodium naphthalenedisulfonic acid) and/or 2-amino-5-naphthol-7-sulfonic acid. The pH value range that can cause color changes in the dye is effectively expanded to include weak alkali, weak acid or even neutral conditions. This expanded range allows the dye to be effectively applied for coloring cotton fabrics and detecting substances such as sweat within a pH range of 4.2-8.3. The color fixation rate of the reactive dye of the present disclosure can reach more than 50%, and the reactive dye exhibits excellent colorfastness to water washing, rubbing, and sunlight exposure, with a rating of 3-4 or higher. The reactive dye of the present disclosure exhibits a high color changing precision by shifting the maximum absorption wavelength of the solution by 51 nm within a pH range of 0.70-0.80 units. Furthermore, the color-changing isoelectric point (corresponding to the absorbance value of the dye solution when its color is changed) occurs at a pH value of 6.00-7.00. This solves the issue associated with current pH-sensitive reactive dyes, which require strong acidic or alkaline conditions for color change.

One aspect of the embodiments of the present disclosure provides a reactive dye. In some embodiments, a structural formula of the reactive dye may be in a general formula (1):

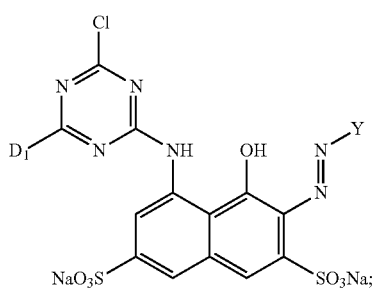

formula (1)

In some embodiments, a structure of Y in the formula (1) is one of a formula (2), a formula (3), a formula (4), a formula (5), or a formula (6):

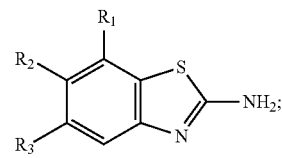

formula (2)

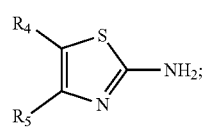

formula (3)

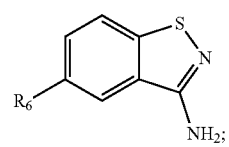

formula (4)

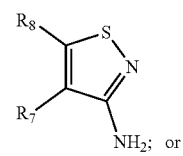

formula (5)

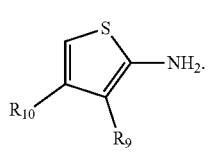

formula (6)

In some embodiments, $R_1$, $R_2$ and $R_3$ in the formula (2) may be independently —H, —NO$_2$, —OCH$_3$, and halogen; $R_4$ and $R_5$ in the formula (3), and $R_7$ and $R_8$ in the formula (5) may be independently —H, —NO$_2$; $R_6$ in the formula (4) may be one of —H and —NO$_2$; and $R_9$ and $R_{10}$ in the formula (6) may be independently —H, —NO$_2$, —CN, and halogen.

In some embodiments, D1 in the formula (1) may be represented by formula (A):

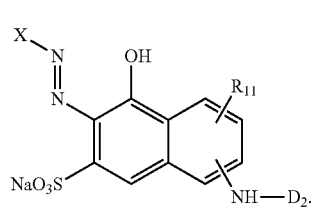

formula (A)

In some embodiments, X in the formula (A) may be one of the formula (2), the formula (3), the formula (4), the formula (5), or the formula (6), and $R_{11}$ may be —H or —SO$_3$Na, D2 is —H, or a formula (B);

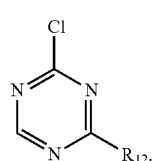

formula (B)

In some embodiments, $R_{12}$ in the formula (B) may be formula (B1) or a formula (B2):

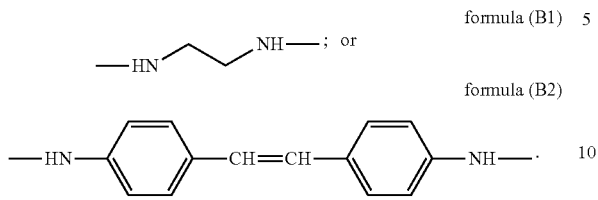

formula (B1)

formula (B2)

In some embodiments, the reactive dye may include a reactive dye with a structure of a formula (1-1):

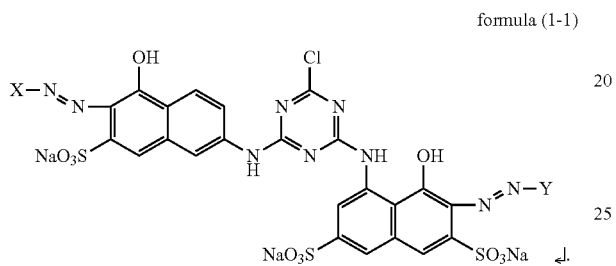

formula (1-1)

In some embodiments, the reactive dye may include a reactive dye with a structure of a formula (1-2):

Another aspect of the embodiments of the present disclosure provides a preparation method of a reactive dye. The preparation method may comprise:

(i) Primary Condensation Reaction adding cyanuric chloride and sodium butyl naphthalene sulfonate into an ice-water mixture to obtain a cyanuric chloride solution; adding a parent compound of the reactive dye into water to obtain a parent compound solution of the reactive dye; mixing the parent compound solution with the cyanuric chloride solution, and obtaining a primary condensation solution after the reaction is finished; and regulating a pH value of the primary condensation solution to 1.5, then adding potassium chloride to precipitate solid powder, dispersing the precipitated solid powder in absolute ethanol, filtering, and freeze-drying to obtain a primary condensation product;

(ii) Secondary Condensation Reaction dissolving the primary condensation product in water to obtain an aqueous solution of the primary condensation product; mixing the aqueous solution of the primary condensation product with a reaction solution, increasing temperature to 30-35° C., regulating the pH to 4.5-5.0, and continuing the reaction at 30-35° C. to obtain a secondary condensation solution, wherein the reaction solution corresponds to the parent compound; regulating the pH value of the secondary condensation solution to 2.0, and adding potassium chloride to precipitate solid powder; and dispersing the precipitated formula (1-2)

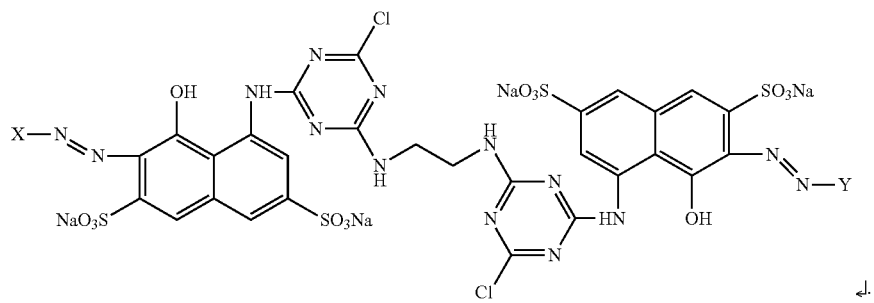

In some embodiments, the reactive dye may include a reactive dye with a structure of a formula (1-3):

solid powder in absolute ethanol, filtering, and freeze-drying to obtain a secondary condensation product;

formula (1-3)

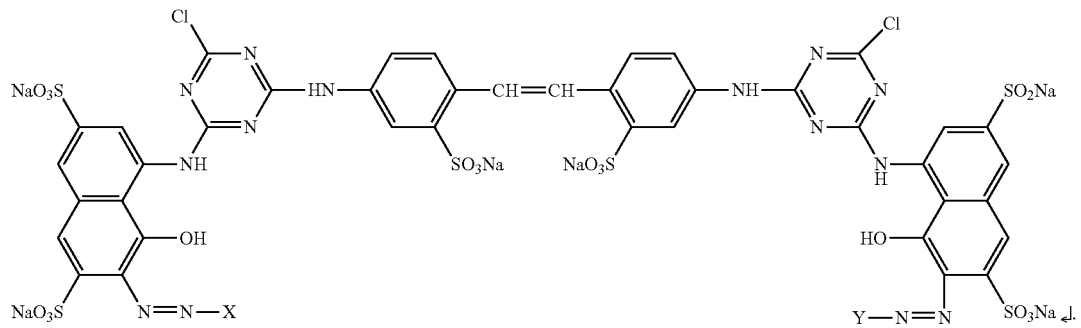

(iii) Diazotization-Coupling Reaction dissolving a heterocyclic primary arylamine derivative in acid, adding a diazotization reagent to react, and after the reaction is finished, eliminating excess nitrous acid to obtain a heterocyclic primary arylamine diazonium salt; dissolving the secondary condensation product in water, and slowly adding the heterocyclic primary arylamine diazo salt; and after the reaction is finished, obtaining the reactive dye after salting out, suction filtration, ethanol washing and drying.

In some embodiments, the cyanuric chloride solution in (i) may be obtained in various ways. For example, the cyanuric chloride solution may be obtained by fully beating cyanuric chloride and sodium butyl naphthalene sulfonate under a certain condition.

In some embodiments, the pH may be regulated using one or more of acetic acid, a saturated sodium bicarbonate solution, sodium hydroxide or potassium hydroxide, ammonia water, hydrochloric acid, propionic acid, concentrated sulfuric acid (98%, w/w) or dilute sulfuric acid (40-70%, w/w), phosphoric acid, and nitric acid.

In some embodiments, a reaction endpoint of (ii) and (iii) may be determined using a reaction endpoint reagent. For example, the reaction endpoint of the secondary condensation solution obtained in (ii) may be detected using an amino reagent, or the reaction endpoint of the reactive dye in (iii) may be detected using H acid (1-amino-8-hydroxy-3,6-sodium naphthalenedisulfonic acid).

In some embodiments, the parent compound of the dye compound may be 4,4'-diamino-2,2'-stilbenedisulfonic acid or 2-amino-5-naphthol-7-sulfonic acid, and the reaction solution may be an aqueous solution of 1-amino-8-hydroxy-3,6-naphthalenedisulfonic acid.

In some embodiments, the pH of the aqueous solution of 1-amino-8-hydroxy-3,6-naphthalenedisulfonic acid may be within a range of 6.0-6.5.

In some embodiments, the parent compound may be 1-amino-8-hydroxy-3,6-naphthalenedisulfonic acid, and the reaction solution may be ethylenediamine.

In some embodiments, the pH of ethylenediamine may be 9.

In some embodiments, the heterocyclic primary arylamine derivative in (iii) may include the compound represented by the formula (2), the formula (3), the formula (4), the formula (5), or the formula (6).

In some embodiments, a molar ratio of the secondary condensation solution to the heterocyclic primary arylamine diazo salt in (iii) may be 1:2.

In some embodiments, when the parent compound is 4,4'-diamino-2,2'-stilbenedisulfonic acid and the reaction solution is the aqueous solution of 1-amino-8-hydroxyl-3,6-naphthalenedisulfonic acid, the reactive dye with the structure in the formula (1-3) may be prepared. The specific preparation method may comprise:

(1) Primary Condensation Reaction adding cyanuric chloride and sodium butylnaphthalene sulfonate into an ice-water mixture, and fully pulping at 0-5° C. to obtain a cyanuric chloride solution; adding 4,4'-diamino-2,2'-stilbenedisulfonic acid into water, regulating the pH to 6.0-6.5, and fully dissolving to obtain a 4,4'-diamino-2,2'-stilbenedisulfonic acid solution; then slowly adding the 4,4'-diamino-2,2'-stilbenedisulfonic acid solution into the cyanuric chloride solution and mixing, regulating the pH to 3.0-3.5, continuing the reaction at 0-5° C., and detecting the reaction endpoint using an amino reagent to obtain a primary condensation solution; regulating the pH value of the primary condensation solution to 1.5 by using acetic acid, and adding potassium chloride to precipitate solid powder; and dispersing the precipitated solid powder in absolute ethanol, filtering, and freeze-drying to obtain a primary condensation product;

(2) Secondary Condensation Reaction dissolving the primary condensation product in water to obtain an aqueous solution of the primary condensation product; adding 1-amino-8-hydroxy-3,6-naphthalenedisulfonic acid into water, and regulating the pH to 6.0-6.5 to obtain a 1-amino-8-hydroxy-3,6-naphthalenedisulfonic acid solution; then adding the 1-amino-8-hydroxy-3,6-naphthalenedisulfonic acid solution into the aqueous solution of the primary condensation product, increasing temperature to 30-35° C., regulating the pH to 4.5-5.0, continuing the reaction at 30-35° C., and detecting the reaction endpoint using the amino reagent to obtain a secondary condensation solution; regulating the pH value of the secondary condensation solution to 2.0 using acetic acid, and then adding potassium chloride to precipitate solid powder; and dispersing the precipitated solid powder in absolute ethanol, filtering, and freeze-drying to obtain a secondary condensation product;

(3) Diazotization-Coupling Reaction dissolving the heterocyclic primary arylamine derivative in acid, adding a diazotization reagent at 0-5° C. and keeping the temperature for 3-4 h, after the reaction is finished, eliminating excess nitrous acid to obtain a heterocyclic primary arylamine diazo salt; dissolving the secondary condensation product in water, reducing the temperature of the solution to 10-15° C., slowly adding the primary arylamine diazo salt, continuing the reaction at 10-15° C. for 1-3 h, regulating the pH to 6, continuing the reaction, and detecting the reaction endpoint using H acid (1-amino-8-hydroxy-3,6-sodium naphthalenedisulfonic acid); and after the reaction is finished, obtaining the reactive dye.

In some embodiments, a mass ratio of cyanuric chloride, sodium butylnaphthalene sulfonate, and the ice-water mixture in (1) may be (2-5):(0.05-0.5):(12-18). In some embodiments, a mass ratio of cyanuric chloride, sodium butylnaphthalene sulfonate, and the ice-water mixture in (1) may be (3-4):(0.08-0.4):(14-16). In some embodiments, a mass ratio of cyanuric chloride, sodium butylnaphthalene sulfonate, and the ice-water mixture in (1) may be (3.5-4.0):(0.1-0.3):15. In some embodiments, a mass ratio of cyanuric chloride, sodium butylnaphthalene sulfonate, and the ice-water mixture in (1) may be 3:0.4:15. In some embodiments, a mass ratio of cyanuric chloride, sodium butylnaphthalene sulfonate, and the ice-water mixture in (1) may be 2:0.1:12. In some embodiments, a mass ratio of cyanuric chloride, sodium butylnaphthalene sulfonate, and the ice-water mixture in (1) may be 5:0.4:17.

In some embodiments, a mass ratio of cyanuric chloride, sodium butylnaphthalene sulfonate, and the ice-water mixture in (1) may be 3.74:0.19:15.

In some embodiments, a mass ratio of 4,4'-diamino-2,2'-stilbenedisulfonic acid to water in (1) may be (2-5):10. In some embodiments, a mass ratio of 4,4'-diamino-2,2'-stilbenedisulfonic acid to water in (1) may be (3-4):10. In some embodiments, a mass ratio of 4,4'-diamino-2,2'-stilbenedisulfonic acid to water in (1) may be 2:10, 3:10, 4:10, or 5:10. In some embodiments, a mass ratio of 4,4'-diamino-2,2'-stilbenedisulfonic acid to water in (1) may be 3.82:10.

In some embodiments, the pH of the 4,4'-diamino-2,2'-stilbenedisulfonic acid solution in (1) may be regulated using a saturated sodium carbonate solution.

In some embodiments, a molar ratio of 4,4'-diamino-2,2'-stilbenedisulfonic acid to cyanuric chloride in (1) may be 1:2.

In some embodiments, the pH of the primary condensation solution in (1) may be regulated using the saturated sodium carbonate solution.

In some embodiments, a mass ratio of potassium chloride to the primary condensation solution in (1) may be (0.250-0.342):1.

In some embodiments, a dosage ratio (g:mL) of the primary condensation product to water in (2) may be (6-8):(80-100).

In some embodiments, a dosage ratio (g:mL) of the primary condensation product to water in (2) may be 7.1:90.

In some embodiments, a dosage ratio of 1-amino-8-hydroxy-3,6-naphthalenedisulfonic acid to water in (2) may be (6-7):15.

In some embodiments, the pH of the 1-amino-8-hydroxy-3,6-naphthalenedisulfonic acid solution in (2) may be regulated using the saturated sodium carbonate solution.

In some embodiments, a molar ratio of the primary condensation solution to 1-amino-8-hydroxy-3,6-naphthalenedisulfonic acid in (2) may be 1:2.

In some embodiments, the pH may be regulated to 4.5-5.0 using the saturated sodium carbonate solution in (2).

In some embodiments, a mass ratio of potassium chloride to the primary condensation solution in (2) may be (0.250-0.342):1.

In some embodiments, the diazotization reagent in (3) may be a sodium nitrite solution or a nitrosyl sulfuric acid solution, a concentration of which may be 30% (w/w) and 40% (w/w) respectively.

In some embodiments, a molar ratio of heterocyclic primary arylamine to the diazotization reagent in (3) may be 1:(1.1-1.2), to ensure complete diazotization of the diazo component.

In some embodiments, the heterocyclic primary arylamine derivative in (3) may include one of the formula (2), the formula (3), the formula (4), the formula (5), and the formula (6).

In some embodiments, a mass ratio of the heterocyclic primary arylamine derivative to acid in (3) may be 1:(2-50), to ensure complete dissolution of the diazo component. In some embodiments, a mass ratio of the heterocyclic primary arylamine derivative to the acid in (3) may be 1:(2-40). In some embodiments, a mass ratio of the heterocyclic primary arylamine derivative to the acid in (3) may be 1:(2-20). In some embodiments, a mass ratio of the heterocyclic primary arylamine derivative to the acid in (3) may be 1:(2-10). In some embodiments, a mass ratio of the heterocyclic primary arylamine derivative to the acid in (3) may be 1:4.

In some embodiments, the acid in (3) may include one or more of hydrochloric acid, propionic acid, concentrated sulfuric acid (98%, w/w) or dilute sulfuric acid (40-70%, w/w), phosphoric acid, etc.

In some embodiments, the excess nitrous acid (e.g., nitrous acid) in (3) may be eliminated by adding sulfamic acid.

In some embodiments, a usage ratio (g:mL) of the secondary condensation product to water in (3) may be (12-15):85.

In some embodiments, a usage ratio (g:mL) of the secondary condensation product to water in (3) may be 13.61:85.

In some embodiments, a molar ratio of the secondary condensation solution to the heterocyclic primary arylamine diazo salt in (3) may be 1:2.

According to the reactive dye represented by the formula (1-3), the pH chromotropic reactive dye capable of dyeing cotton fabrics may be prepared by using heterocyclic primary amine as a diazo component, 4,4'-diamino-2,2'-stilbenedisulfonic acid and s-triazine as a bridging group, and a dichlorotriazine group as an active group. In some embodiments of the present disclosure, the pH-sensitive color-changing compound of the reactive dye is covalently bonded into the chemical structure of fiber by the nucleophilic substitution reaction between monochlorotriazine and the hydroxyl group in the textile structure. The size of the conjugated system and the range of electron delocalization of the dye are changed by the reversible isomerization reaction between the hydroxyl group adjacent to the diazo group and the diazo group under different pH conditions. This reversible color change mechanism allows for the dye's color to change in response to pH variations. Moreover, the dye in some embodiments of the present has a double-color-changing structure, which increases the capability of the dye bonding with —H/—OH. The pH value range that can cause color changes in the dye is effectively expanded to include weak alkali, weak acid or even neutral conditions.

In some embodiments, the reactive dye represented by the formula (1-1) may be prepared using the parent compound of the dye compound as 2-amino-5-naphthol-7-sulfonic acid, and the reaction solution as the aqueous solution of 1-amino-8-hydroxy-3,6-naphthalenedisulfonic acid. The specific preparation may comprise:

(1) Primary Condensation Reaction adding cyanuric chloride and sodium butylnaphthalene sulfonate into an ice-water mixture, and fully beating them at 0-5° C. to obtain a cyanuric chloride solution; adding 1-amino-8-hydroxy-3,6-naphthalenedisulfonic acid into water, regulating the pH to 6.0-6.5 to obtain a 1-amino-8-hydroxy-3,6-naphthalenedisulfonic acid solution; then mixing the 1-amino-8-hydroxy-3,6-naphthalenedisulfonic acid solution with the cyanuric chloride solution, regulating the pH to 3.0-3.5, continuing the reaction at 0-5° C., and maintain the pH value of the reaction solution at 3.0-3.5 using a sodium carbonate solution; detecting a reaction endpoint using an amino reagent to obtain a primary condensation solution; and regulating the pH value of the primary condensation solution to 1.5 using acetic acid, add potassium chloride to precipitate solid powder, and dispersing the precipitated solid powder in absolute ethanol, filtering, and freeze-drying to obtain a primary condensation product;

(2) Secondary Condensation Reaction dissolving the primary condensation product in water to obtain an aqueous solution of the primary condensation product; regulating the pH of ethylenediamine to 9.0; then slowly adding ethylenediamine with the pH of 9 into the aqueous solution of the primary condensation product, increasing temperature to 30-35° C., regulating the pH to 4.5-5.0, continuing the reaction at 30-35° C., and maintaining the pH value of the reaction solution at 4.0-4.5 using the sodium carbonate solution; detecting the reaction endpoint using the amino reagent to obtain a secondary condensation solution; then regulating the pH value of the secondary condensation solution to 2.0 using acetic acid, and adding potassium chloride to precipitate solid powder; and dispersing the precipitated solid powder in absolute ethanol, filtering, and freeze-drying to obtain a secondary condensation product;

(3) Diazotization-Coupling Reaction dissolving a heterocyclic primary arylamine derivative in acid, adding a diazotization reagent at 0-5° C. and keeping the temperature for 3-4 h, after the reaction is finished, eliminating excess nitrous acid to obtain a heterocyclic primary arylamine diazo salt; dissolving the secondary condensation product in water, reducing the temperature of the solution to 10-15° C., slowly adding the heterocyclic primary arylamine diazo salt, continuing the reaction at 10-15° C. for 1-3 h, regulating the pH to 6, continuing the reaction, and detecting the reaction endpoint using H acid (1-amino-8-hydroxy-3,6-sodium naphthalenedisulfonic acid); and after the reaction is finished, obtaining the reactive dye after salting out, suction filtration, ethanol washing and drying.

In some embodiments, a mass ratio of cyanuric chloride, sodium butylnaphthalene sulfonate and the ice-water mixture in (1) may be (2-5):(0.05-0.5):(12-18). In some embodiments, a mass ratio of cyanuric chloride, sodium butylnaphthalene sulfonate and the ice-water mixture in (1) may be (3-4):(0.08-0.4):(14-16). In some embodiments, a mass ratio of cyanuric chloride, sodium butylnaphthalene sulfonate and the ice-water mixture in (1) may be (3.5-4.0):(0.1-0.3):15. In some embodiments, a mass ratio of cyanuric chloride, sodium butylnaphthalene sulfonate and the ice-water mixture in (1) may be 3:0.4:15. In some embodiments, a mass ratio of cyanuric chloride, sodium butylnaphthalene sulfonate and the ice-water mixture in (1) may be 2:0.1:12. In some embodiments, a mass ratio of cyanuric chloride, sodium butylnaphthalene sulfonate and the ice-water mixture in (1) may be 5:0.4:17.

In some embodiments, a mass ratio of cyanuric chloride, sodium butylnaphthalene sulfonate and the ice-water mixture in (1) may be 3.74:0.19:15.

In some embodiments, a dosage ratio of 1-amino-8-hydroxy-3,6-naphthalenedisulfonic acid to water in (1) may be (0.5-1):1.

In some embodiments, a usage ratio of 1-amino-8-hydroxy-3,6-naphthalenedisulfonic acid to water in (1) may be 0.651:1.

In some embodiments, the pH of the 1-amino-8-hydroxy-3,6-naphthalenedisulfonic acid solution in (1) may be regulated using sodium carbonate.

In some embodiments, a molar ratio of 1-amino-8-hydroxy-3,6-naphthalenedisulfonic acid to cyanuric chloride in (1) may be 1:1.

In some embodiments, a mass ratio of potassium chloride to the primary condensation solution in (1) may be (0.250-0.342):1.

In some embodiments, the pH of the primary condensation solution in (1) may be regulated using a saturated sodium bicarbonate solution.

In some embodiments, a mass ratio of the primary condensation product to water in (2) may be (0.2-0.8):1. In some embodiments, a mass ratio of the primary condensation product to water in (2) may be (0.3-0.6):1.

In some embodiments, a mass ratio of the primary condensation product to water in (2) may be (0.4-0.5):1.

In some embodiments, a mass ratio of the primary condensation product to water in (2) may be 0.479:1.

In some embodiments, the pH of ethylenediamine in (2) may be regulated using hydrochloric acid.

In some embodiments, a molar ratio of the primary condensation product to ethylenediamine in (2) may be 2:1.

In some embodiments, the pH in (2) may be regulated using the saturated sodium bicarbonate solution.

In some embodiments, a mass ratio of potassium chloride to the secondary condensation solution in (2) may be (0.250-0.342):1.

In some embodiments, the diazotization reagent in (3) may be a sodium nitrite solution (30% mass concentration) or a nitrosyl sulfuric acid solution (40% mass concentration).

In some embodiments, a molar ratio of the heterocyclic primary arylamine derivative to the diazotization reagent in (3) may be 1:(1.1-1.2), to ensure complete diazotization of the diazo component.

In some embodiments, the heterocyclic primary arylamine derivative in (3) may include one of the formula (2), the formula (3), the formula (4), the formula (5), or the formula (6).

In some embodiments, a mass ratio of the heterocyclic primary arylamine derivative to the acid in (3) may be (0.01-15):1. In some embodiments, a mass ratio of the heterocyclic primary arylamine derivative to the acid in (3) may be (0.05-12):1. In some embodiments, a mass ratio of the heterocyclic primary arylamine derivative to the acid in (3) may be (0.01-10):1. In some embodiments, a mass ratio of the heterocyclic primary arylamine derivative to the acid in (3) may be (0.05-1):1. In some embodiments, a mass ratio of the heterocyclic primary arylamine derivative to the acid in (3) may be 0.25:1.

In some embodiments, the acid in (3) may include any one or more of a hydrochloric acid solution, a propionic acid solution, concentrated sulfuric acid solution (98%, w/w) or dilute sulfuric acid (40-70%, w/w), a phosphoric acid solution, etc.

In some embodiments, the excess nitrous acid in (3) may be eliminated by adding sulfamic acid.

In some embodiments, a dosage ratio of the secondary condensation product to water in (3) may be (0.05-0.6):1. In some embodiments, a dosage ratio of the secondary condensation product to water in (3) may be (0.2-0.6):1. In some embodiments, a dosage ratio of the secondary condensation product to water in (3) may be (0.05-0.2):1. In some embodiments, a usage ratio of the secondary condensation product to water in (3) may be 0.16:1. In some embodiments, the usage ratio of the secondary condensation product to water in (3) may be 0.36:1.

In some embodiments, a molar ratio of the secondary condensation product to the heterocyclic primary arylamine diazo salt in (3) may be 1:2.

The reactive dye represented by the formula (1-1) may be prepared using the heterocyclic primary amine as the diazo component, the compound containing the s-triazine group as the active group as the coupling component, and the s-triazine group as the bridging group. The pH-sensitive color-changing compound of the reactive dye is covalently bonded into the fiber chemical structure by the nucleophilic substitution reaction between s-triazine and the hydroxyl group in the textile structure, and the size of the conjugated system and the range of electron delocalization of the dye are changed by the reversible isomerization reaction of the hydroxyl group adjacent to the diazo group and the diazo group under different pH regulations, thereby achieving the reversible color change of the dye. Moreover, the dye of the present disclosure has a double-color-changing structure, which increases the capability of the dye bonding with —H/—OH. The pH value range that can cause color changes in the dye is effectively expanded to include weak alkali, weak acid or even neutral conditions. The dye can be used for sweat detection.

In some embodiments, the reactive dye represented by the formula (1-2) may be prepared when the parent compound is 1-amino-8-hydroxyl-3,6-naphthalenedisulfonic acid, and the reaction solution is the aqueous solution of ethylenediamine. The specific preparation may comprise:

(a) Primary Condensation Reaction adding cyanuric chloride and sodium butylnaphthalene sulfonate into an ice-water mixture, and fully beating them at 0-5° C. to obtain a cyanuric chloride solution; adding 2-amino-5-naphthol-7-sulfonic acid into water, regulating the pH to 6.0-6.5 to obtain a 2-amino-5-naphthol-7-sulfonic acid solution; then mixing the 2-amino-5-naphthol-7-sulfonic acid solution with the cyanuric chloride solution, regulating the pH to 3.0-3.5, continuing the reaction at 0-5° C., and maintaining the pH of the reaction solution at 3.0-3.5 using a sodium carbonate solution; detecting a reaction endpoint using an amino reagent to obtain a primary condensation solution; regulating the pH value of the primary condensation solution to 1.5 using acetic acid, and then adding potassium chloride to precipitate solid powder; and dispersing the precipitated solid powder in absolute ethanol, filtering and freeze-drying to obtain a primary condensation product;

(b) Secondary Condensation Reaction dissolving the primary condensation product in water to obtain an aqueous solution of the primary condensation product; adding 1-amino-8-hydroxy-3,6-naphthalenedisulfonic acid into water, and regulating the pH to 6.0-6.5 to obtain a 1-amino-8-hydroxy-3,6-sodium naphthalenedisulfonic acid solution; then adding the 1-amino-8-hydroxy-3,6-naphthalenedisulfonic acid solution into the aqueous solution of the primary condensation product, increasing the temperature to 30-35° C., regulating the pH to 4.5-5.0, at 30-35° C., continuing the reaction, and maintaining the pH value of the reaction solution at 4.0-4.5 using a sodium carbonate solution; detecting a reaction endpoint using an amino reagent to obtain a secondary condensation solution; regulating the pH value of the secondary condensation solution to 2.0 using acetic acid, and then adding potassium chloride to precipitate solid powder; and dispersing the precipitated solid powder in absolute ethanol, filtering and freeze-drying to obtain a secondary condensation product;

(c) Diazotization-Coupling Reaction dissolving a heterocyclic primary arylamine derivative in acid, adding a diazotization reagent at 0-5° C. and keeping the temperature for 3-4 h, after the reaction is finished, eliminating excess nitrous acid to obtain a heterocyclic primary arylamine diazo salt; dissolving the secondary condensation product in water, reducing the temperature of the solution to 10-15° C., slowly adding the heterocyclic primary arylamine diazo salt, continuing the reaction at 10-15° C. for 1-3 h, regulating the pH to 6, continuing the reaction, and detecting the reaction endpoint using H acid (1-amino-8-hydroxy-3,6-sodium naphthalenedisulfonic acid); and after the reaction is finished, obtaining the reactive dye after salting out, suction filtration, ethanol washing and drying.

In some embodiments, a mass ratio of cyanuric chloride, sodium butylnaphthalene sulfonate and the ice-water mixture in (1) may be (2-5):(0.05-0.5):(12-18). In some embodiments, a mass ratio of cyanuric chloride, sodium butylnaphthalene sulfonate and the ice-water mixture in (1) may be (3~4):(0.08~0.4):(14~16). In some embodiments, a mass ratio of cyanuric chloride, sodium butylnaphthalene sulfonate and the ice-water mixture in (1) may be (3.5-4.0):(0.1-0.3):15. In some embodiments, a mass ratio of cyanuric chloride, sodium butylnaphthalene sulfonate and the ice-water mixture in (1) may be 3:0.4:15. In some embodiments, a mass ratio of cyanuric chloride, sodium butylnaphthalene sulfonate and the ice-water mixture in (1) may be 2:0.1:12. In some embodiments, a mass ratio of cyanuric chloride, sodium butylnaphthalene sulfonate and the ice-water mixture in (1) may be 5:0.4:17.

In some embodiments, a mass ratio of cyanuric chloride, sodium butylnaphthalene sulfonate and the ice-water mixture in (1) may be 3.74:0.19:15.

In some embodiments, a dosage ratio of 2-amino-5-naphthol-7-sulfonic acid to water in (a) may be (0.20-1):1. In some embodiments, a dosage ratio of 2-amino-5-naphthol-7-sulfonic acid to water in (a) may be (0.30-0.7):1. In some embodiments, a dosage ratio of 2-amino-5-naphthol-7-sulfonic acid to water in (a) may be (0.20-0.50):1. In some embodiments, a dosage ratio of 2-amino-5-naphthol-7-sulfonic acid to water in (a) may be 0.493:1.

In some embodiments, the pH of the 2-amino-5-naphthol-7-sulfonic acid solution in (a) may be regulated using sodium carbonate.

In some embodiments, a molar ratio of 2-amino-5-naphthol-7-sulfonic acid to cyanuric chloride in (a) may be 1:1.

In some embodiments, a mass ratio of potassium chloride to the primary condensation solution in (a) may be (0.250-0.342):1.

In some embodiments, the pH of the primary condensation solution in (1) may be regulated using a saturated sodium bicarbonate solution.

In some embodiments, a mass ratio of the primary condensation product to water in (b) may be (1-6):20. In some embodiments, a mass ratio of the primary condensation product to water in (b) may be (2-5):20.

In some embodiments, a mass ratio of the primary condensation product to water in (b) may be (3-4):20.

In some embodiments, a mass ratio of the primary condensation product to water in (b) may be 3.74:20.

In some embodiments, a dosage ratio of 1-amino-8-hydroxy-3,6-naphthalenedisulfonic acid to water in (b) may be (0.25-0.45):1. In some embodiments, a dosage ratio of 1-amino-8-hydroxy-3,6-naphthalenedisulfonic acid to water in (b) may be 0.319:1.

In some embodiments, the pH of the 1-amino-8-hydroxy-3,6-naphthalenedisulfonic acid solution in (b) may be regulated using a saturated sodium carbonate solution.

In some embodiments, a molar ratio of the primary condensation product to 1-amino-8-hydroxy-3,6-naphthalenedisulfonic acid in (b) may be 1:1.

In some embodiments, the pH in (b) may be regulated to 4.5-5.0 using the saturated sodium bicarbonate solution.

In some embodiments, a mass ratio of potassium chloride to the secondary condensation solution in (b) may be (0.250-0.342):1.

In some embodiments, the heterocyclic primary arylamine derivative in (3) may include one of the formula (2), the formula (3), the formula (4), the formula (5), or the formula (6).

In some embodiments, the acid in (c) may include any one or more of a hydrochloric acid solution, a propionic acid solution, a concentrated sulfuric acid solution (98%, w/w) or dilute sulfuric acid (40-70%, w/w), a phosphoric acid solution, etc.

In some embodiments, a mass ratio of the heterocyclic primary arylamine derivative to the acid in (c) may be (0.01-15):1. In some embodiments, a mass ratio of the heterocyclic primary arylamine derivative to the acid in (c) may be (0.05-12):1. In some embodiments, a mass ratio of the heterocyclic primary arylamine derivative to the acid in (c) may be (0.01-10):1. In some embodiments, a mass ratio of the heterocyclic primary arylamine derivative to the acid in (c) may be (0.05-1):1. In some embodiments, a mass ratio of the heterocyclic primary arylamine derivative to the acid in (c) may be 0.25:1.

In some embodiments, the diazotization reagent in (c) may be a sodium nitrite solution or a nitrosyl sulfuric acid solution, a concentration of the sodium nitrite solution may be 30% (w/w), and a concentration of nitrosyl sulfuric acid solution may be 40% (w/w).

In some embodiments, a molar ratio of the heterocyclic primary arylamine to the diazotization reagent in (c) may be 1:(1.1-1.2), to ensure complete diazotization of the diazo component.

In some embodiments, the excess nitrous acid in (c) may be eliminated by adding sulfamic acid.

In some embodiments, a dosage ratio of the secondary condensation product to water in (c) may be (0.05-0.6):1. In some embodiments, the dosage ratio of the secondary condensation product to water in (c) may be (0.2-0.5):1. In some embodiments, the dosage ratio of the secondary condensation product to water in (c) may be (0.05-0.2):1. In some embodiments, the dosage ratio of the secondary condensation product to water in (c) may be 0.16:1. In some embodiments, the dosage ratio of the secondary condensation product to water in (c) may be 0.36:1.

In some embodiments, a molar ratio of the secondary condensation product to the heterocyclic primary arylamine diazo salt in (c) may be 1:2.

The reactive dye represented by the formula (1-2) uses heterocyclic primary amine as a diazo component, a compound containing a s-triazine group as an active group as a coupling component, and ethylenediamine as a bridging group. The pH-sensitive color-changing compound of the reactive dye is covalently bonded into the fiber chemical structure by the nucleophilic substitution reaction between s-triazine and the hydroxyl group in the textile structure, and the size of the conjugated system and the range of electron delocalization of the dye are changed by the reversible isomerization reaction of the hydroxyl group adjacent to the diazo group and the diazo group under different pH regulations. This reversible color change mechanism allows for the dye's color to change in response to pH variations. Moreover, the double-color-changing structure increases the capability of the dye bonding with —H/—OH. The pH value range that can cause color changes in the dye is effectively expanded to include weak alkali, weak acid or even neutral conditions, and the reactive dye can be used for the sweat detection.

Another aspect of the embodiments of the present disclosure provides a color-changing textile. In some embodiments, the color-changing textile may be obtained by dyeing a textile with the reactive dye described above.

In some embodiments, the textile may include a cotton fabric, a viscose fabric, a hemp fabric or blended fibers and fabrics thereof.

Another aspect of the embodiments of the present disclosure provides a sweat detection sensor using the reactive dye for sweat detection and sensing. For example, when there is sweat (the pH value of human sweat is within a range of 4.2-8.3), the sweat detection sensor may display a numerical value or display a color change.

Another aspect of the embodiments of the present disclosure provides a method for dyeing a cotton fabric with a reactive dye. The method may include adopting the reactive dye capable of dyeing the cotton fabrics to dye the cotton fabrics.

The following examples are some more specific illustrations of embodiments related to some embodiments. Part of the content in these examples may also be replaced or combined with corresponding content in other examples to form new examples. The experimental methods in the following examples are conventional methods unless otherwise specified. The experimental materials used in the following examples were purchased from general biochemical reagent companies unless otherwise specified. Quantitative experiments in the following examples were all set up to repeat the experiments three times, and the results were averaged. It should be understood that the following examples are intended to better explain the present disclosure, and not intended to limit the present disclosure.

EXAMPLE

Test Methods

1. Washing Fastness Test:
    measured in accordance with AATCC61/2003 "Test Procedure 1A, 2A and 3A Color Fastness to Household and Commercial Laundering: Accelerated".
2. Rubbing Color Fastness Test:
    measured in accordance with GB/T3920-1997 "Textile Color Fastness Test Color Fastness to Rubbing".
3. Fastness to Sunlight Test:
    measured in accordance with GB/T8427-1998 "Textile-Tests for color fastness Color Fastness to Artificial Light: Hernia Arc".
4. Proton Nuclear Magnetic Resonance Spectrum ($^1$H-NMR):
    samples were characterized by NMR using deuterated water as a solvent and an NMR spectrometer (AVANCE III).
5. Color Fixation Rate:
    the color fixation rate is a ratio of a K/S value of a printed fabric after soaping to a K/S value of the printed fabric after washing with 50% DMF for 10 min at 25° C., and the calculation formula is in the following formula (1):

$$F(\%) = \frac{(K/S) \text{ after } DMF}{(K/S) \text{ after soaping}} \quad (1)$$

6. Color-Changing Test:
    a dye was added into 500 mL of $1 \times 10^{-4}$ mol/L aqueous solution, and then the pH value of the solution was regulated using hydrochloric acid, acetic acid, an acetic acid/sodium acetate buffer solution, sodium bicarbonate, sodium hydroxide, etc., and the samples were measured respectively using an ultraviolet-visible spectrophotometer (UV-2450, Hitachi), wherein a detection wavelength range was 380-780 nm.

7. K/S Value Characterization:
   an apparent color depth of printed fabrics was expressed by a K/S value of the printed fabrics. According to the Kubelka-Munk law, see the following formula (2):

$$\frac{K}{S} = \frac{(1-R)^2}{2R} \qquad (2)$$

where: K is a light absorption coefficient; S is a scattering coefficient; and R is a reflectance at λmax when the light is not transmitted.

Example 1

1. Primary Condensation Reaction
   (1) 3.74 g (0.02 mol) of cyanuric chloride and 0.19 g of sodium butylnaphthalene sulfonate were added into 15 g of ice-water mixture, which are fully beated for 1 h at 0-5° C. to obtain a cyanuric chloride solution;
   (2) 3.82 g of 4,4'-diamino-2,2'-stilbenedisulfonic acid (0.01 mol, 97%) was added into 40 g of water, the pH was regulated to 6.0-6.5 using a saturated sodium carbonate solution, and after being fully dissolved, a 4,4'-diamino-2,2'-stilbenedisulfonic acid solution was obtained;
   (3) then the 4,4'-diamino-2,2'-stilbenedisulfonic acid solution was slowly added into the cyanuric chloride solution and mixed, and the pH was regulated to 3.0-3.5 using the saturated sodium bicarbonate solution, the reaction was continued at 5° C., and a reaction endpoint was detected using an amino reagent to obtain a primary condensation solution;
   (4) the pH of the primary condensation solution was regulated to 1.5 using acetic acid, and then potassium chloride was added to precipitate solid powder (a mass ratio of potassium chloride to the primary condensation solution was 0.3:1); and
   (5) the precipitated solid powder was dispersed in absolute ethanol, filtered, and freeze-dried to obtain a primary condensation product.
2. Secondary Condensation Reaction
   (1) 7.10 g (0.01 mol) of the primary condensation product was dissolved in 90 mL of water to prepare an aqueous solution of the primary condensation product;
   (2) 6.38 g (0.02 mol) of 1-amino-8-hydroxy-3,6-naphthalenedisulfonic acid was added into 15 g of water, and the pH was regulated to 6.0-6.5 using the saturated sodium carbonate solution to obtain 1-amino-8-hydroxy-3,6-sodium naphthalenedisulfonic acid solution;
   (3) then the 1-amino-8-hydroxy-3,6-naphthalenedisulfonic acid solution was added into the aqueous solution of the primary condensation product, the temperature was increased to 30-35° C., the pH was regulated to 4.5-5.0, the reaction was continued at 30-35° C., and the pH of the reaction solution was maintained at 4.0-4.5 using a sodium carbonate solution;
   (4) a reaction endpoint was detected using the amino reagent to obtain a secondary condensation solution;
   (5) the pH of the secondary condensation solution was regulated to 2.0 using acetic acid, then a certain amount of potassium chloride was added to precipitate solid powder (a mass ratio of potassium chloride to the secondary condensation solution was 0.3:1); and
   (6) the precipitated solid powder was dispersed in absolute ethanol, filtered, and freeze-dried to obtain a secondary condensation product.
3. Diazotization-Coupling Reaction
   (1) 15.6 g of 98% (w/w) sulfuric acid solution was added into a 250 mL three-necked flask, 3.90 g (0.02 mol) of 2-amino-6-nitrobenzothiazole was slowly added and stirred for 1 h to fully dissolve it, 6.99 g (0.022 mol) of 40% (w/w) nitrosyl sulfuric acid solution was added dropwise below 0° C., 3.9 g of glacial acetic acid was added dropwise at 0-5° C., and the reaction was finished in 3-4 h;
   (2) sulfamic acid was added to eliminate excess nitrous acid to obtain a heterocyclic primary arylamine diazo salt;
   (3) 13.61 g of the secondary condensation product (0.01 mol) was dissolved in 85 mL of water, the temperature was reduced to 10-15° C., and 0.02 mol of the prepared heterocyclic primary arylamine diazo salt was slowly added, the reaction was continued for 2 h at 10-15° C., the pH was regulated to 6, the reaction was continued, and a reaction endpoint was detected using H acid (1-amino-8-hydroxy-3,6-sodium naphthalenedisulfonic acid); and
   (4) after the reaction was finished, the reactive dye was obtained after salting out, suction filtration, washing with ethanol and drying.

Figure 41:
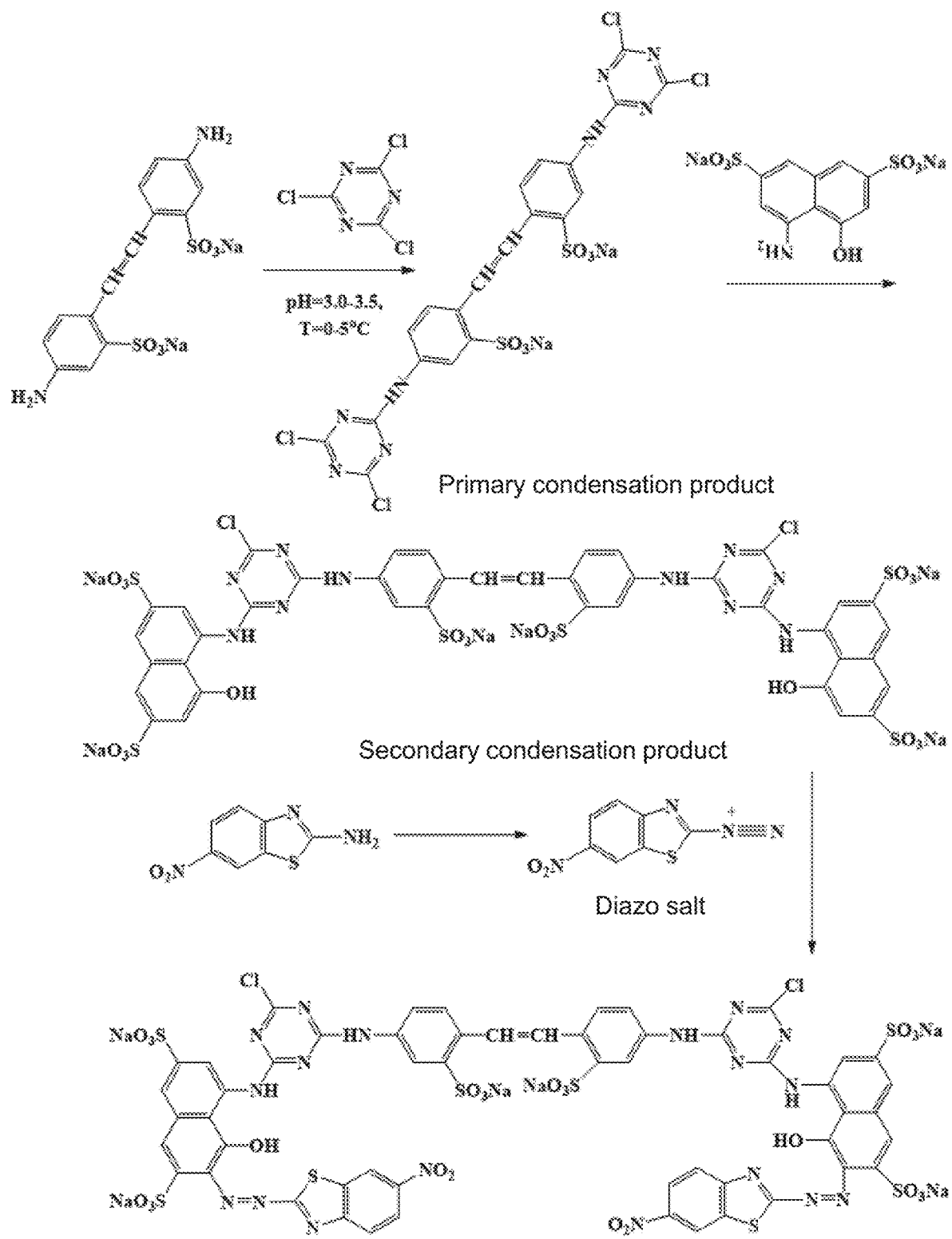
FIG. 41 illustrates a synthetic pathway of the reactive dye of Example 1.

The synthetic pathway of the reactive dye is shown in FIG. 41. The structural formula of the reactive dye is as follows:

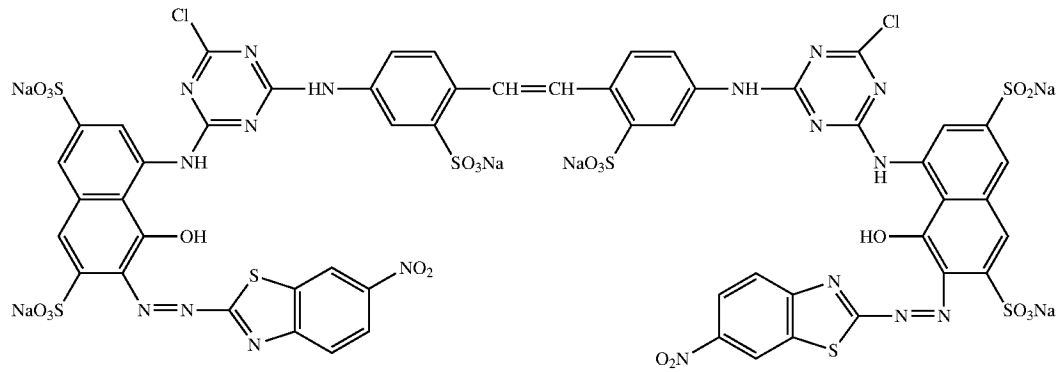

The structural characterization is as follows:

$^1$H-NMR (400 MHz, DMSO-d6): δ 9.43 (s, 4H, —NH—), 9.01 (s, 2H, —OH), 8.18 (s, 2H, hydrogen on the naphthalene ring), 8.05 (d, 2H, hydrogen on the naphthalene ring), 7.91, 7.89 (d, 2H, hydrogen on the benzene ring), 7.77 (s, 2H, hydrogen on the benzene ring), 7.56-7.51 (m, 6H, hydrogen on the benzene ring hydrogen and hydrogen on benzothiazole), 7.47 (s, 2H, hydrogen on naphthalene ring), 7.05 (s, 2H, —CH═CH—), and 7.00 (s, 2H, hydrogen on benzothiazole).

Figure 2:
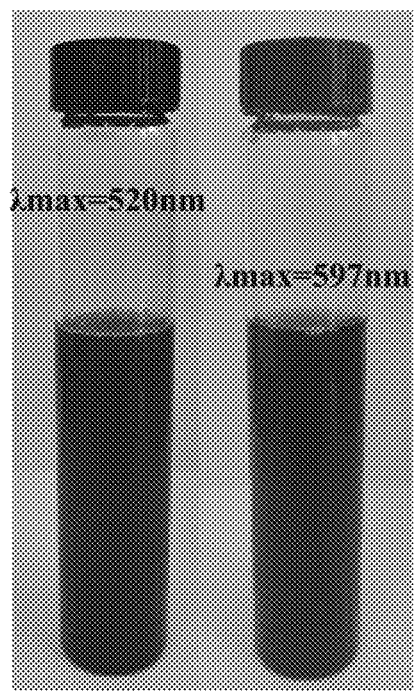
FIG. 2 is an optical picture of a dyeing solution after color changing in Example 1.

The spectral curves of the dye in Example 1 under different pH conditions (pH=3.2-12.8) are in FIG. 1, and the optical picture of the dye solution is in FIG. 2. It can be seen from FIG. 1 and FIG. 2 that when the pH value of the solution is greater than or equal to 7.9, the solution is blue (the maximum absorption wavelength is 597 nm), and when the pH value of the solution is less than 7.9, the solution is red (the maximum absorption wavelength is 520 nm).

Figure 3:
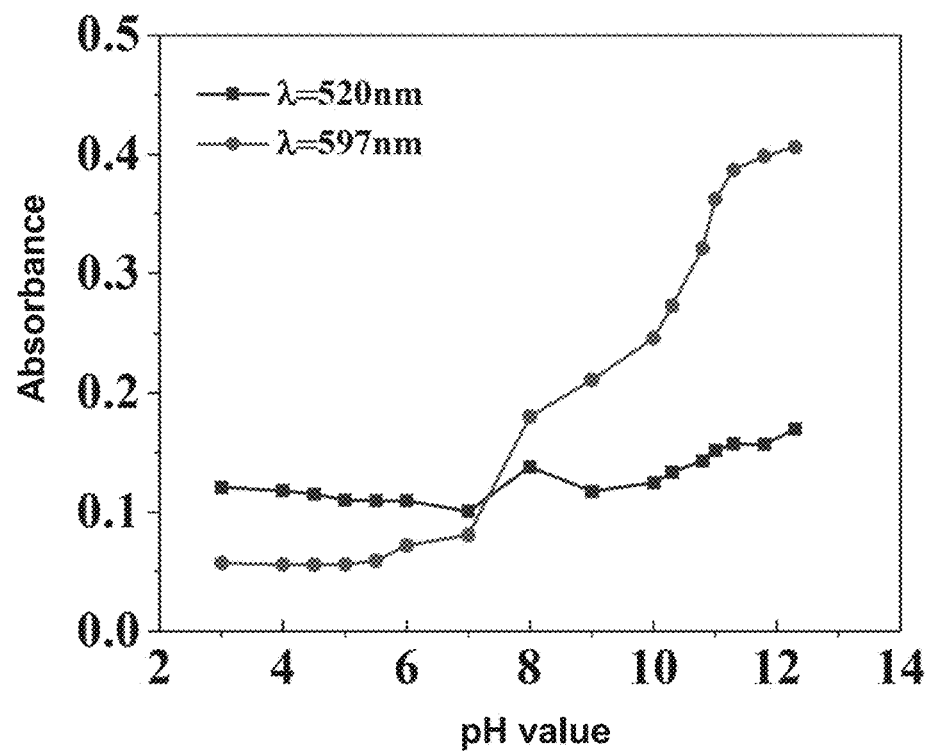
FIG. 3 illustrates a variation of an absorbance at a maximum absorption wavelength of a solution with a pH value before and after color changing of a dye in Example 1.
Figure 4:
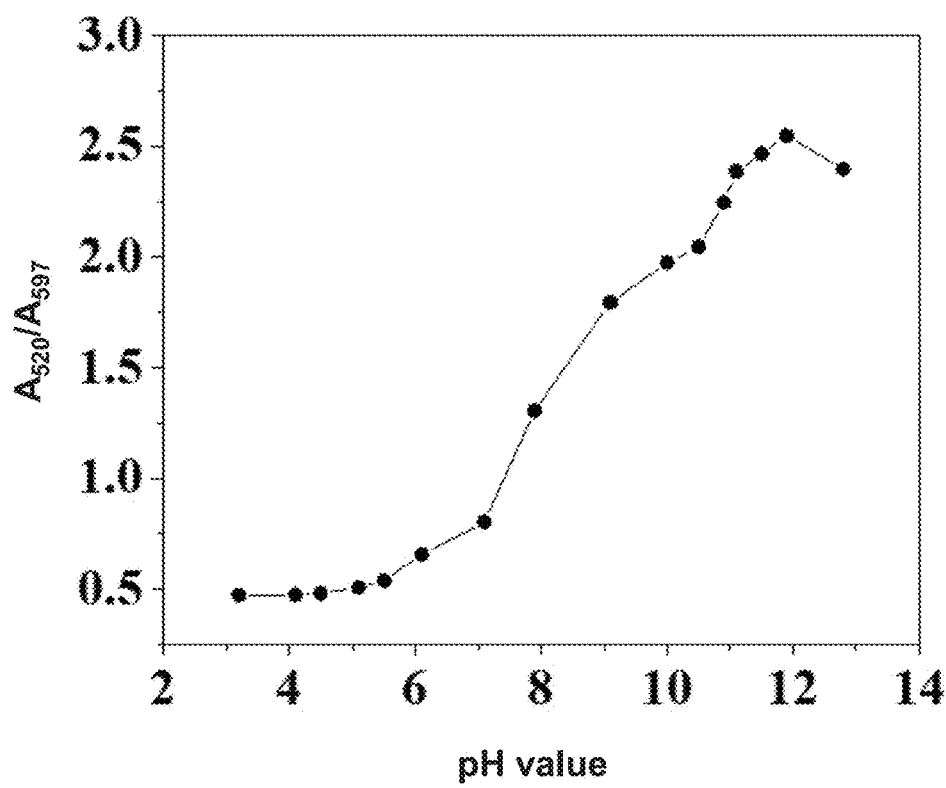
FIG. 4 illustrates a variation of an absorbance ratio of a solution with a pH value before and after color changing of a dye in Example 1.

A variation of an absorbance and an absorbance ratio at a maximum absorption wavelength with the pH of a solution before and after color changing of the dye in Example 1 is in FIG. 3 and FIG. 4. It can be seen from FIG. 3 and FIG. 4 that the pH value at the color-changing isoelectric point (the absorbance value of the solution when the color is changed) of the solution is 7.9.

Example 2

1. Primary Condensation Reaction was the Same as Step 1 of Example 1
2. Secondary Condensation Reaction was the Same as Step 2 of Example 1
3. Diazotization-Coupling Reaction
   (1) 15.6 g of 98% (w/w) sulfuric acid solution was added into a 250 mL three-necked flask, 3.9 g (0.02 mol) 3-amino-5-nitrobenzisothiazole was slowly added, and stirred for 1 h below 50° C. to fully dissolve it, 6.99 g (0.022 mol) 40% (w/w) nitrosyl sulfuric acid solution was slowly added dropwise below 0° C., and 3.9 g of glacial acetic acid was slowly added dropwise at 0-5° C. and reacted for 4 h;
   (2) after the reaction is finished, sulfamic acid was added to eliminate excess nitrous acid to obtain a heterocyclic primary arylamine diazo salt;
   (3) 7.22 g of the secondary condensation product (0.01 mol) was dissolved in 20 mL of water, the temperature was reduced to 10-15° C., and the prepared heterocyclic primary arylamine diazo salt was slowly added, the reaction was continued at 10-15° C. for 2 h, the pH was regulated to 6, the reaction was continued, and a reaction endpoint was detected using H acid (1-amino-8-hydroxy-3,6-naphthalenedisulfonic acid); and
   (4) after the reaction is finished, the reactive dye was obtained after salting out, suction filtration, washing with ethanol and drying.

Figure 42:
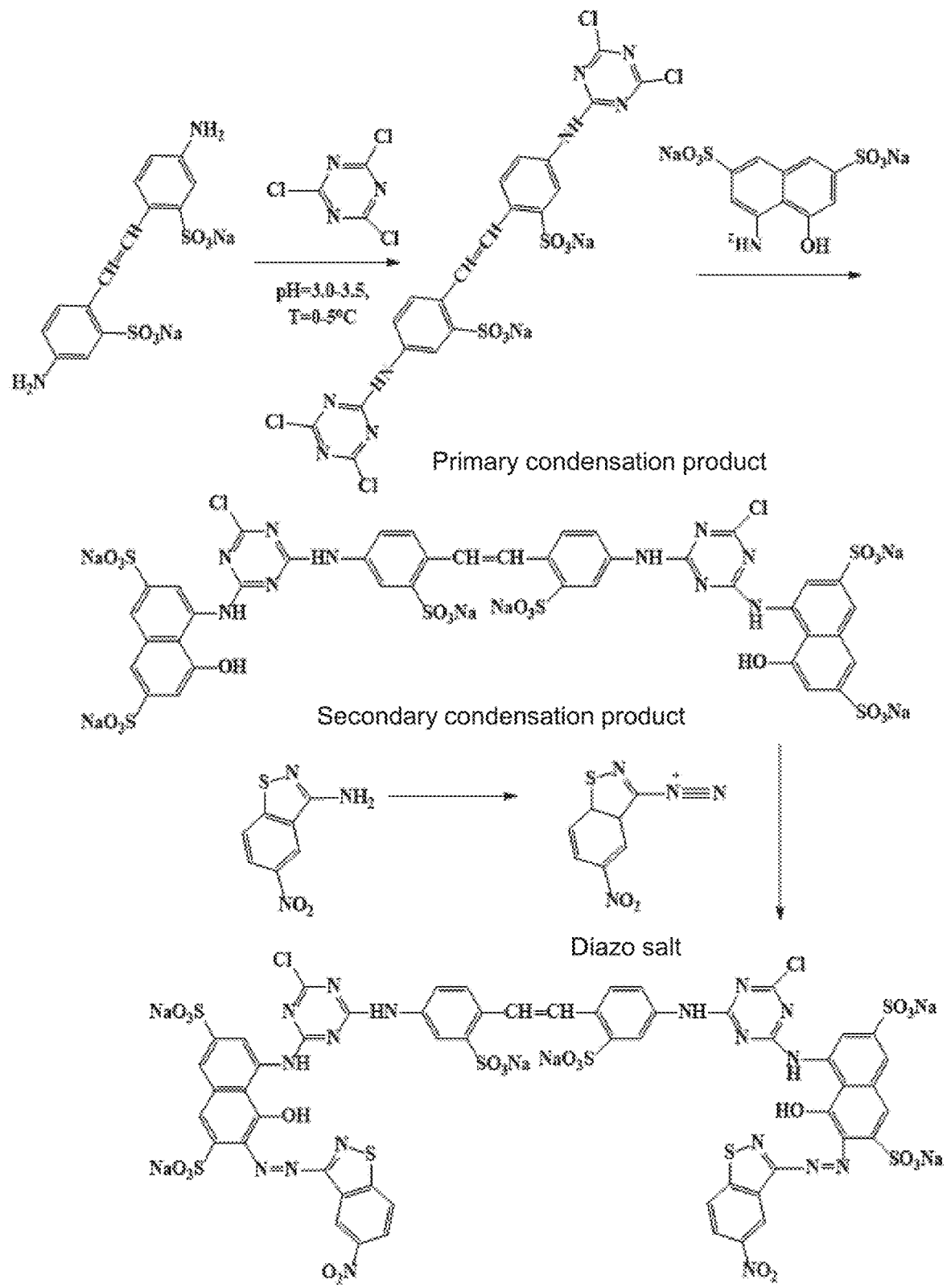
FIG. 42 illustrates a synthetic pathway of the reactive dye of Example 2.

The synthetic pathway of the reactive dye is shown in FIG. 42. The structural formula of the reactive dye is as follows:

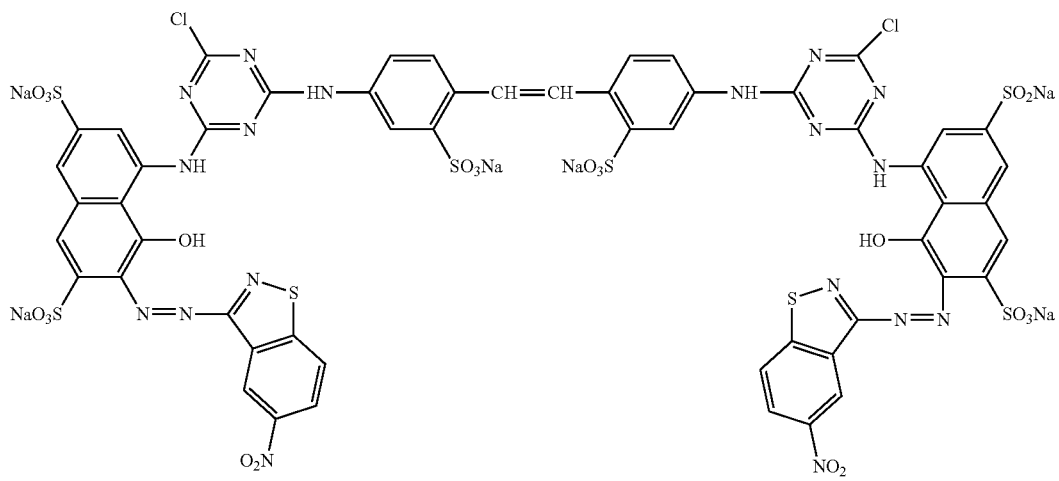

The structural characterization is as follows:

$^1$H-NMR (400 MHz, DMSO-d6): δ 9.43 (s, 4H, —NH—), 9.01 (s, 2H, —OH), 8.18 (s, 2H, hydrogen on the naphthalene ring), 8.05 (d, 2H, hydrogen on the naphthalene ring), 7.91, 7.89 (d, 2H, hydrogen on the benzene ring), 7.83, 7.81 (d, 2H, hydrogen on the benzothiazole), 7.77 (s, 2H, hydrogen on the benzene ring), 7.63, 7.61 (d, 2H, hydrogen on benzothiazole), 7.53, 7.51 (d, 2H, hydrogen on benzene ring), 7.47 (s, 2H, hydrogen on naphthalene ring), 7.05 (s, 2H, —CH═CH—), and 7.09 (s, 2H, hydrogen on benzisothiazole).

Figure 5:
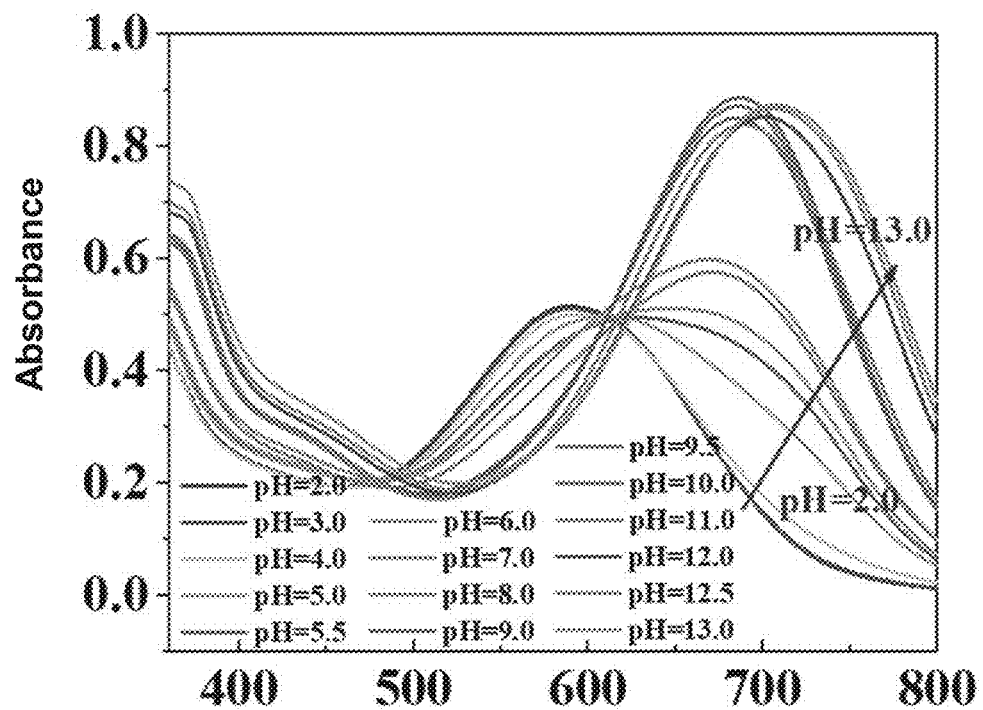
FIG. 5 is spectrum curves illustrating a dye in Example 2 under different pH conditions (pH=1-14).
Figure 6:
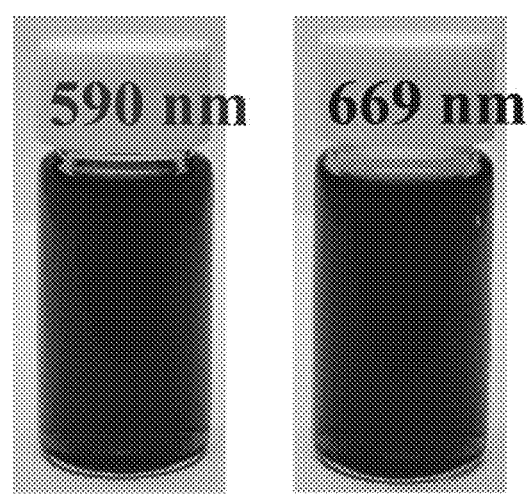
FIG. 6 is an optical picture of a dyeing solution after color changing in Example 2.

The spectral curves of the dye in Example 2 under different pH conditions (pH=1-14) are in FIG. 5, and the optical chronotropic picture of the dye is in FIG. 6. It can be seen from FIG. 5 and FIG. 6 that when the pH value of the solution is greater than or equal to 5.5, the solution is green (the maximum absorption wavelength is 669 nm), and when the pH value of the solution is less than 5.5, the solution is purple (the maximum absorption wavelength is 590 nm).

Figure 7:
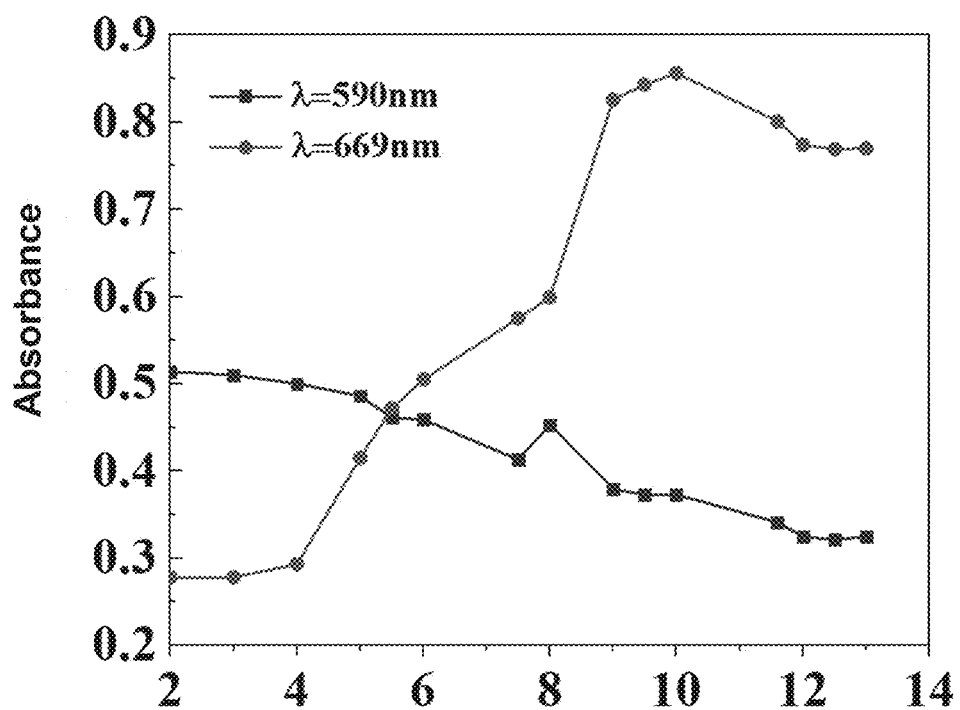
FIG. 7 illustrates a variation of an absorbance at a maximum absorption wavelength of a solution with a pH value before and after color changing of a dye in Example 2.
Figure 8:
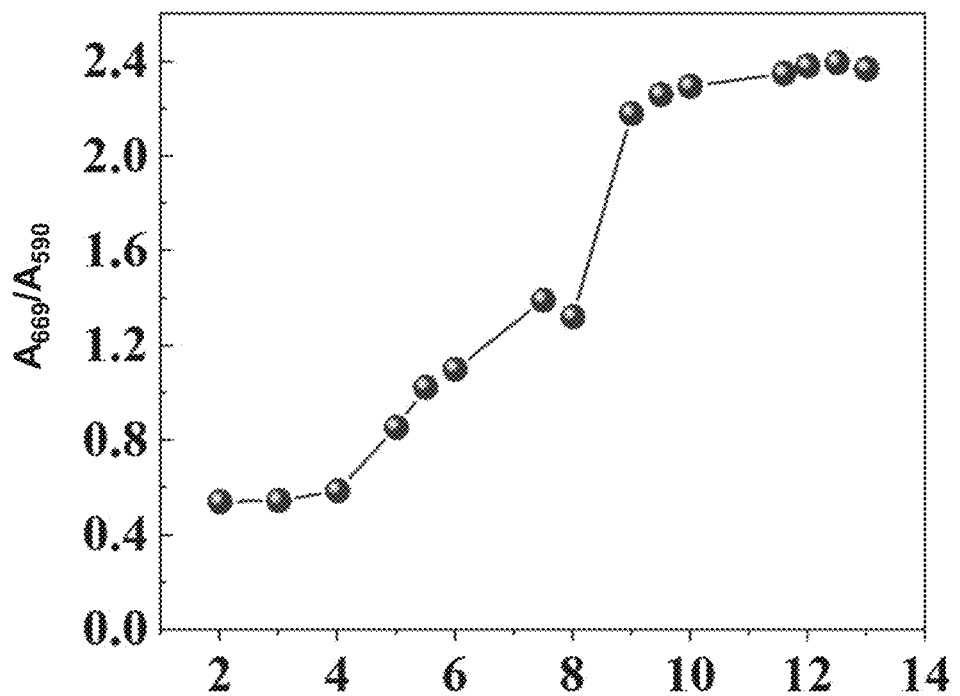
FIG. 8 illustrates a variation of an absorbance ratio of a solution with a pH value before and after color changing of a dye in Example 2.

A variation of an absorbance and an absorbance ratio at the maximum absorption wavelength of the solution with the pH value before and after color changing of the dye in Example 2 is in FIG. 7 and FIG. 8. It can be seen from FIG. 7 and FIG. 8 that the pH value at the color-changing isoelectric point (absorbance value of the solution when the color is changed) of the solution is 5.50.

Example 3 Dyeing the Cotton Fabrics Using Reactive Dyes

A preparation method of a color-changing cotton fabric (140 g/m$^2$, pure cotton bleached knitted fabric) is descripted as follows.

1. dyeing prescription: 2% owf of dye (the dyes obtained in Example 1 and Example 2), 25 g/L of anhydrous sodium sulphate, and 20 g/L of sodium carbonate; bath ratio 1:15;
2. dyeing process: preparing a dye solution according to the dyeing prescription, wetting the cotton fabric and adding the cotton fabric into a dyeing bottle, increasing the temperature to 60° C. for initial dyeing for 5 min, continuing to increase the temperature to 90° C., adding anhydrous sodium sulphate and sodium carbonate, and dyeing at the temperature for 60 min, cooling and drying to obtain the color-changing cotton fabric.

The cotton fabric obtained in Example 3 was soaked in sweat simulation solutions (see Table 1) with different pH values for testing. The test results are in Table 2 and FIGS. 9-12.

TABLE 1

Sweat simulation solutions with different pH values

| Component | Acid sweat simulation solution | Alkaline sweat simulation solution |
| --- | --- | --- |
| L-histidine hydrochloride monohydrate | 0.5 g/L | 0.5 g/L |
| Sodium chloride | 5 g/L | 5 g/L |
| Sodium dihydrogen phosphate dihydrate | 2.2 g/L | — |
| Disodium hydrogen phosphate dihydrate | — | 2.5 g/L |
| 0.1 mol/L sodium hydroxide solution | Regulating pH value to 5.5 | Regulating pH value to 8.0 |

TABLE 2

Performance test results

| Indicator | | Color fixation rate F % | Water fastness/ K/S | Rubbing fastness/level | | Fastness to sunlight/ level |
| --- | --- | --- | --- | --- | --- | --- |
| | | | | Dry | Wet | |
| Dye in Example 1 | Acid sweat simulation solution | 60.06 | 12.36 | 3-4 | 4 | 3~4 | 4 |
| | Alkaline sweat simulation solution | | 11.58 | 4 | 4 | 3~4 | 4 |
| Dye in Example 2 | Acid sweat simulation solution | 50.93 | 7.62 | 3-4 | 4 | 4 | 4 |
| | Alkaline sweat simulation solution | | 8.06 | 4 | 4 | 4 | 4 |

It can be seen from Table 2 that the color fixation rates of the printed cotton fabrics prepared by the dye in Example 1 and the dye in Example 2 all reached more than 50%, and the color fastness to washing, rubbing and sunlight all reached level 3-4 or above.

Figure 9:
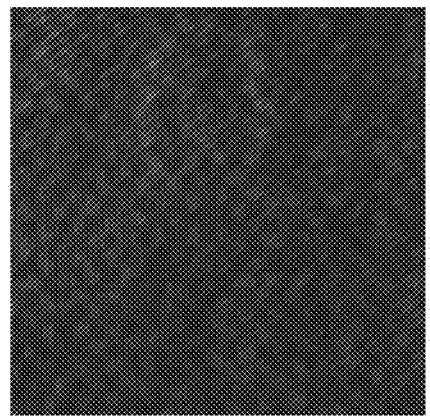
FIG. 9 illustrates a photograph of a printed cotton fabric using the dye in Example 1 under an acidic condition (pH=5.5).
Figure 10:
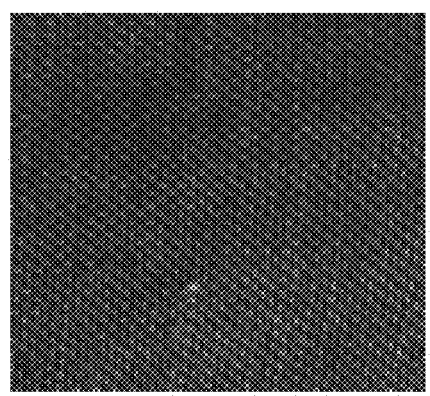
FIG. 10 illustrates a photograph of a printed cotton fabric using the dye in Example 1 under an alkaline condition (pH=8.0).

It can be seen from FIG. 9 and FIG. 10 that the dyed cotton fabric prepared by the dye in Example 1 was red under the acid sweat condition (pH=5.5), and blue under the alkaline sweat condition (pH=8.0), which can be applied to human sweat detection.

Figure 11:
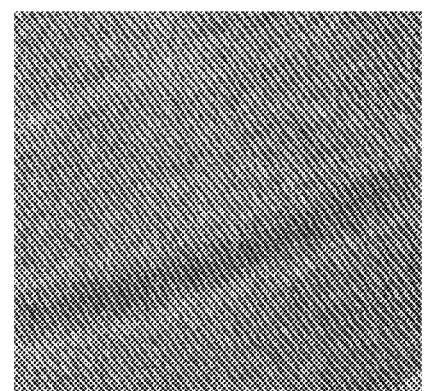
FIG. 11 illustrates a photograph of a printed cotton fabric using the dye in Example 2 under an acidic condition (pH=5.5).
Figure 12:
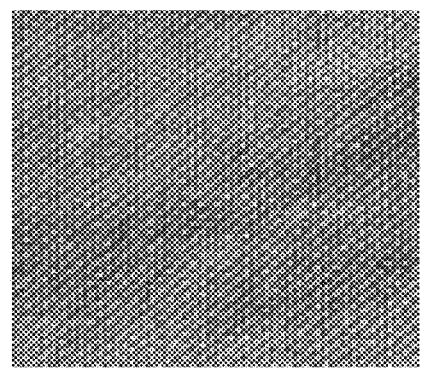
FIG. 12 illustrates a photograph of a printed cotton fabric using the dye in Example 2 under an alkaline condition (pH=8.0).

It can be seen from FIG. 11 and FIG. 12 that the dyed cotton fabric prepared by the dye in Example 2 was red under the acid sweat condition (pH=5.5), and blue under the alkaline sweat condition (pH=8.0), which can be applied to human sweat detection.

Comparative Example 1

A preparation method of a color-changing dye comprises:
1. Primary Condensation Reaction
   (1) adding 3.74 g (0.02 mol) of cyanuric chloride and 0.19 g of sodium butylnaphthalene sulfonate into 15 g of ice-water mixture, and fully pulping for 1 h at 0-5° C. to obtain a cyanuric chloride solution;
   (2) adding 5.5 g (0.02 mol) of 2-amino-1,4-benzenedisulfonic acid and 25.56 g water into a beaker and stirring evenly, regulating the pH to 6.0-6.5 using sodium carbonate, and fully dissolving to obtain an aniline-2,5-disulfonic acid solution;
   (3) then mixing the aniline-2,5-disulfonic acid solution and the cyanuric chloride solution, regulating the pH to 3.0-3.5 using a saturated sodium bicarbonate solution, continuing the reaction at 0-5° C., and maintaining the pH value of the reaction solution at 3.0-3.5 using a sodium carbonate solution;
   (4) detecting a reaction endpoint using an amino reagent to obtain a primary condensation solution;
   (5) regulating the pH value of the primary condensation solution to 1.5 using acetic acid, adding potassium chloride to precipitate solid powder (a mass ratio of potassium chloride to the primary condensation solution was 0.3:1); and
   (6) dispersing the precipitated solid powder in absolute ethanol, filtering, and freeze-drying to obtain a primary condensation product.
2. Secondary Condensation Reaction
   (1) dissolve 8.18 g (0.02 mol) of the primary condensation product in 20 mL of water to prepare an aqueous solution of the primary condensation product;
   (2) quickly adding 10.62 g (0.01 mol) of P-3R (CI reactive blue 49) chromogen dry powder into the aqueous solution of the primary condensation product, increasing the temperature to 30-35° C., regulating the pH to 4.5-5.0 using the saturated sodium bicarbonate solution, continuing the reaction at 30-35° C., and maintaining the pH of the reaction solution at 4.5-5.0 using the sodium carbonate solution;
   (3) detecting the reaction endpoint using the amino reagent to obtain a secondary condensation solution;
   (4) regulating the pH value of the secondary condensation solution to 2.0 using acetic acid, and then adding a certain amount of potassium chloride to precipitate solid powder (a mass ratio of potassium chloride to the secondary condensation solution was 0.3:1); and
   (5) dispersing the precipitated solid powder in absolute ethanol, filtering, and freeze-drying to obtain a secondary condensation product.
3. Diazotization-Coupling Reaction
   (1) adding 7.22 g (0.02 mol)) of meta-sulfonic acid para-ester into a 250 mL beaker, adding 6 mL of 36% (w/w) hydrochloric acid solution, stirring evenly, cooling down to 0-5° C., and slowly adding 0.022 mol 30% (w/w) sodium nitrite solution, wherein the reaction was finished in 1 h;
   (2) adding sulfamic acid to eliminate excess nitrous acid to obtain a m-sulfonic acid para-ester diazo salt;
   (3) dissolving 0.02 mol 18.23 g of the secondary condensation product in 20 mL of water, reducing the temperature to 10-15° C., and slowly adding the prepared m-sulfonic acid para-ester diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and (4) after the reaction is finished, obtaining the color-changing dye after salting out, suction filtration, ethanol washing and drying.

The structural formula of the obtained color-changing dye is as follows:

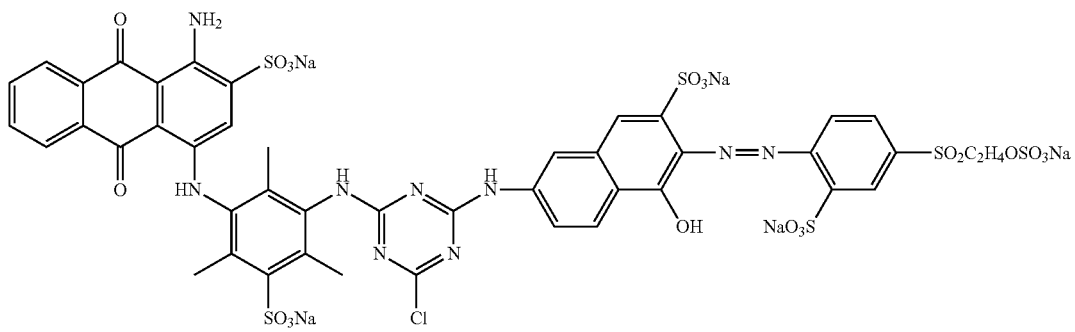

The cotton fabric was dyed according to the method of Example 3. The color fixation rate of the dye on the cotton fabric was only 21.08%, the effect of dyeing the cotton fabric was poor, and the pH value for making the dyed fabric color changed was greater than or equal to 9.0 (in strong alkali condition), which cannot be used for sweat detection.

Comparative Example 2

A preparation method of a chromotropic dye comprises:
1. Primary Condensation Reaction
   (1) adding 3.74 g (0.02 mol) of cyanuric chloride and 0.19 g of sodium butylnaphthalene sulfonate into 15 g of ice-water mixture, and fully pulping for 1 h at 0-5° C. to obtain a cyanuric chloride solution;
   (2) adding 5.5 g (0.02 mol) of 2,4-diaminobenzene sulfonate and 25.56 g of water into a beaker and stirring evenly, regulating the pH to 6.0-6.5 using sodium carbonate, and fully dissolving to obtain a 2,4-sodium diaminobenzene sulfonate solution;
   (3) then mixing the 2,4-sodium diaminobenzene sulfonate solution and the cyanuric chloride solution, regulating the pH to 3.0-3.5 using a saturated sodium bicarbonate solution, continuing the reaction at 0-5° C., and maintaining the pH of the reaction solution at 3.0-3.5 using a sodium carbonate solution;
   (4) detecting a reaction endpoint using an amino reagent to obtain a primary condensation solution;
   (5) regulating the pH value of the primary condensation solution to 1.5 using acetic acid, adding potassium chloride to precipitate solid powder (a mass ratio of potassium chloride to the primary condensation solution was 0.3:1); and
   (6) dispersing the precipitated solid powder in absolute ethanol, filtering, and freeze-drying to obtain a primary condensation product.

2. Secondary Condensation Reaction
   (1) dissolving 7.16 g (0.02 mol) of the primary condensation product in 20 mL of water to prepare an aqueous solution of the primary condensation product;
   (2) quickly adding 10.62 g (0.01 mol) of P-3R (CI reactive blue 49) chromogen dry powder into the aqueous solution of the primary condensation product, increasing the temperature to 30-35° C., regulating the pH to 4.5-5.0 using the saturated sodium bicarbonate solution, continuing the reaction at 30-35° C., and maintaining the pH of the reaction solution at 4.5-5.0 using the sodium carbonate solution;
   (3) detecting the reaction endpoint using the amino reagent to obtain a secondary condensation solution;
   (4) regulating the pH value of the secondary condensation solution to 2.0 using acetic acid, and then adding a certain amount of potassium chloride to precipitate solid powder (a mass ratio of potassium chloride to the secondary condensation solution was 0.3:1); and
   (5) dispersing the precipitated solid powder in absolute ethanol, filtering, and freeze-drying to obtain a secondary condensation product.

3. Diazotization-Coupling Reaction
   (1) adding 5.83 g (0.02 mol)) of para-ester into a 250 mL beaker, adding 6 mL of 36% (w/w) hydrochloric acid solution, stirring evenly, cooling down to 0-5° C., and slowly adding 0.022 mol 30% (w/w)/w) sodium nitrite solution, wherein the reaction was finished in 1 h;
   (2) adding sulfamic acid to eliminate excess nitrous acid to obtain a m-sulfonic acid para-ester diazo salt;
   (3) dissolving 0.02 mol 14.97 g of the secondary condensation product in 20 mL of water, reducing the temperature to 10-15° C., and slowly adding the prepared m-sulfonic acid para-ester diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and
   (4) after the reaction is finished, obtaining the pH chromotropic dye after salting out, suction filtration, ethanol washing and drying.

The structural formula of the obtained pH chromotropic dye is as follows:

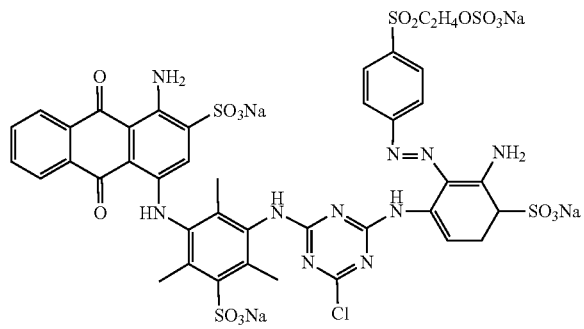

The cotton fabric was dyed according to the method of Example 3, the color fixing rate of the dye on the cotton fabric was only 19.23%, the effect of dyeing the cotton fabric was poor, and the pH value for making the dyed fabric color changed was less than or equal to 1.6 (in strong acid condition), which cannot be used for sweat detection.

Comparative Example 3

A preparation method of a pH chromotropic dye comprises:

1. Primary Condensation Reaction Being the Same as 1 of Example 1

2. Secondary Condensation Reaction
   (1) dissolving 8.80 g (0.02 mol) of the primary condensation product in 20 mL of water to prepare an aqueous solution of the primary condensation product;
   (2) adding 7.66 g (0.02 mol) of 7-amino-1,3,5-naphthalenetrisulfonic acid, regulating the pH to 9.0 using a hydrochloric acid solution, then slowly adding to the aqueous solution of the primary condensation product, increasing the temperature to 30-35° C., regulating the pH to 4.5-5.0 using a saturated sodium bicarbonate solution, continuing the reaction at 30-35° C., and maintaining the pH of the reaction solution at 4.5-5.0 using a sodium carbonate solution;
   (3) detecting reaction endpoint using an amino reagent to obtain a secondary condensation solution;
   (4) regulating the pH value of the secondary condensation solution to 2.0, and then adding a certain amount of potassium chloride to precipitate solid powder (a mass ratio of potassium chloride to the secondary condensation solution was 0.3:1); and
   (5) dispersing the precipitated solid powder in absolute ethanol, filtering, and freeze-drying to obtain a secondary condensation product.

3. Diazotization-Coupling Reaction
   (1) adding 15.6 g of 98% (w/w) sulfuric acid solution into a 250 mL three-necked flask, slowly adding 3.9 g (0.02 mol) 3-amino-5-nitrobenzisothiazole, and stirring for 1 h below 50° C. to fully dissolve it, slowly adding 6.99 g (0.022 mol) of 40% (w/w) nitrosyl sulfuric acid solution dropwise below 0° C., and slowly adding 3.90 g of glacial acetic acid dropwise at 0-5° C., wherein the reaction was finished in 4 h;
   (2) adding sulfamic acid to eliminate excess nitrous acid to obtain a heterocyclic primary arylamine diazo salt;
   (3) dissolving 0.01 mol 4.27 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and
   (4) after the reaction is finished, obtaining the pH chromotropic dye after salting out, suction filtration, ethanol washing and drying.

The structural formula of the obtained pH chromotropic dye is as follows:

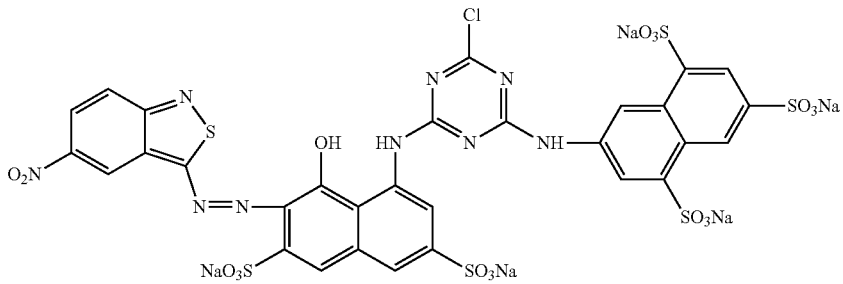

The cotton fabric was dyed according to the method of Example 3. The color fixation rate of the dye on the cotton fabric was only 15.23%, and the effect of dyeing the cotton fabric was poor. The pH value for making the dyed fabric color changed was less than or equal to 5.0, which cannot be used for sweat detection. The washing fastness was level 3, poor than the dyes of Examples 1 and 2.

Comparative Example 4

A preparation method of a dye comprises:
1. Primary Condensation Reaction Being the Same as 1 of Example 1
2. Secondary Condensation Reaction
   (1) dissolving 8.80 g (0.02 mol) of the primary condensation product in 20 mL of water to prepare an aqueous solution of the primary condensation product;

(2) adding 7.66 g (0.02 mol) of 7-amino-1,3,5-naphthalenetrisulfonic acid, regulating the pH to 9.0 using a hydrochloric acid solution, then slowly adding to the aqueous solution of the primary condensation product, increasing the temperature to 30-35° C., regulating the pH to 4.5-5.0 using a saturated sodium bicarbonate solution, continuing the reaction at 30-35° C., and maintaining the pH value of the reaction solution at 4.5-5.0 using sodium carbonate solution;
(3) detect a reaction endpoint using an amino reagent to obtain a secondary condensation solution;
(4) regulating the pH value of the secondary condensation solution to 2.0 using acetic acid, and then adding a certain amount of potassium chloride to precipitate solid powder (a mass ratio of potassium chloride to the secondary condensation solution was 0.3:1); and
(5) dispersing the precipitated solid powder in absolute ethanol, filtering, and freeze-drying to obtain a secondary condensation product.

3. Diazotization-Coupling Reaction
(1) adding 15.6 g of 98% (w/w) sulfuric acid solution into a 250 mL three-neck flask, slowly adding 3.48 g (0.02 mol) of 2,5-dinitrothiophene, and stirring for 1 h below 50° C. to fully dissolve it, slowly adding 6.99 g (0.022 mol) of 40% (w/w) nitrosyl sulfuric acid solution dropwise below 0° C., and slowly adding 3.48 g of glacial acetic acid dropwise at 0-5° C., wherein the reaction was finished in 3-4 h;
(2) adding sulfamic acid to eliminate excess nitrous acid to obtain a heterocyclic primary arylamine diazo salt;
(3) dissolving 0.01 mol 4.27 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and
(4) after the reaction was finished, obtaining the dye after salting out, suction filtration, ethanol washing and drying.

The structural formula of the obtained dye is as follows:

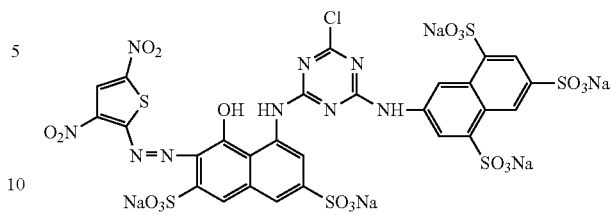

The cotton fabric was dyed according to the method of Example 3. The color fixation rate of the dye on the cotton fabric was only 17.13%, and the effect of dyeing the cotton fabric was poor. The pH value for making the dyed fabric color changed was less than or equal to 3.0 (in strong acid condition), which cannot be used for sweat testing. The washing fastness was level 3, poor than dyes of Examples 1 and 2.

Comparative Example 5

A preparation method of a dye comprises:
1. Primary Condensation Reaction Being the Same as 1 of Example 1
2. Secondary Condensation Reaction Being the Same as 2 of Example 1
3. Diazotization-Coupling Reaction
(1) adding 18.45 g of 98% (w/w) sulfuric acid solution into a 250 mL three-necked flask, slowly adding 4.14 g (0.02 mol) of 2,6-dichloro-4-nitroaniline, and stirring for 1 h below 50° C. to fully dissolve it, and slowly adding 6.99 g (0.022 mol) of 40% (w/w) nitrosyl sulfuric acid solution dropwise below 0° C., wherein the reaction was finished in 4 h;
(2) adding sulfamic acid to eliminate excess nitrous acid to obtain a heterocyclic primary arylamine diazo salt;
(3) dissolving 0.01 mol 13.61 g of the secondary condensation product in 85 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodiumnaphthalenedisulfonic acid); and
(4) after the reaction was finished, obtaining the dye after salting out, suction filtration, ethanol washing and drying.

The structural formula of the obtained dye is as follows:

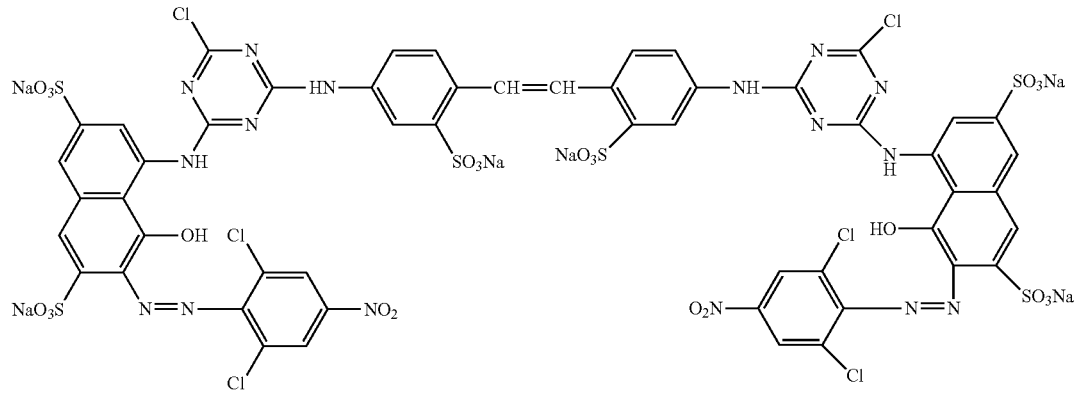

The cotton fabric was dyed according to the method of Example 3, the color fixation rate of the dye on the cotton fabric was 21.06%, and the effect of dyeing the cotton fabric was poor.

Comparative Example 6

A preparation method of a dye comprises:
1. Primary Condensation Reaction Being the Same as 1 of Example 1
2. Secondary Condensation Reaction
   (1) dissolving 7.10 g (0.01 mol) of the primary condensation product in 90 mL of water to prepare an aqueous solution of the primary condensation product;
   (2) add 4.78 g (0.02 mol) of 2-amino-5-naphthol-7-sulfonic acid to 15 g of water to obtain a 2-amino-5-naphthol-7-sulfonic acid solution;
   (3) then slowly adding the 2-amino-5-naphthol-7-sulfonic acid solution into the aqueous solution of the primary condensation product, increasing the temperature to 30-35° C., regulating the pH to 4.5-5.0 using a saturated sodium bicarbonate solution, continuing the reaction at 30-35° C., and maintaining the pH of the reaction solution at 4.5-5.0 using a sodium carbonate solution;
   (4) detecting the reaction end point using an amino reagent to obtain a secondary condensation solution;
   (5) regulating the pH value of the secondary condensation solution to 2.0 using acetic acid, and then adding a certain amount of potassium chloride to precipitate solid powder (a mass ratio of potassium chloride to the secondary condensation solution was 0.3:1); and
   (6) dispersing the precipitated solid powder in absolute ethanol, filtering, and freeze-drying to obtain a secondary condensation product.
3. Diazotization-Coupling Reaction
   (1) adding 50 g of 49% (w/w) sulfuric acid solution into a 250 mL three-necked flask, slowly adding 4.38 g (0.02 mol) of 2-amino-5,6-dichlorobenzothiazole, and stirring for 1 h below 50° C. to fully dissolve it;
   (2) slowly adding 6.99 g (0.022 mol) of 40% (w/w) nitrosylsulfuric acid solution dropwise below 0-5° C., wherein the reaction was finished in 4 h;
   (3) adding sulfamic acid to eliminate excess nitrous acid to obtain a heterocyclic primary arylamine diazo salt;
   (4) dissolving 0.01 mol 9.07 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and
   (5) after the reaction was finished, obtaining the dye after salting out, suction filtration, ethanol washing and drying.

The structural formula of the obtained dye is as follows:

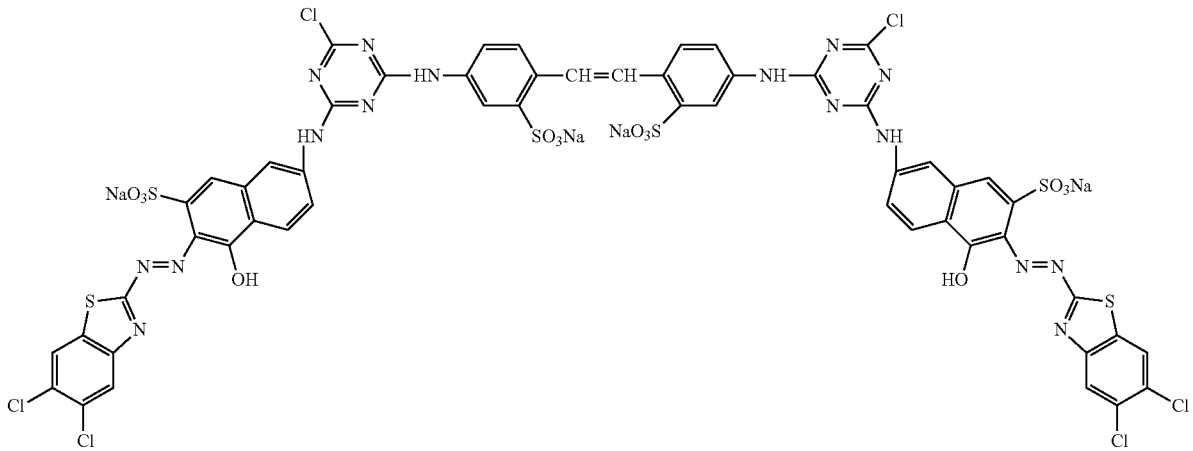

Then the cotton fabric was dyed according to the method of Example 3, the color fixation rate of this dye on the cotton fabric was 39.48%, and the effect of dyeing the cotton fabric was poor.

Example 4

1. Primary Condensation Reaction
   (1) 3.74 g (0.02 mol) of cyanuric chloride and 0.19 g of sodium butylnaphthalene sulfonate was added into 15 g of ice-water mixture, and fully pulped for 1 h at 0-5° C. to obtain a cyanuric chloride solution;
   (2) 6.51 g (0.02 mol, 98%) 1-amino-8-hydroxy-3,6-naphthalenedisulfonic acid was added into 10 g of water, the pH was regulated to 6.0-6.5 using sodium carbonate, and fully dissolved to obtain a 1-Amino-8-hydroxy-3, 6-naphthalenedisulfonic acid solution;
   (3) then the 1-amino-8-hydroxy-3,6-naphthalenedisulfonic acid solution and the cyanuric chloride solution were mixed, the pH was regulated to 3.0-3.5 using a saturated sodium bicarbonate solution at 0-5° C., the reaction was continued, and the pH value of the reaction solution was maintained at 3.0-3.5 using use a sodium carbonate solution;
(4) a reaction endpoint was detected using an amino reagent to obtain a primary condensation solution;
(5) the pH value of the primary condensation solution was regulated to 1.5 using acetic acid, and then potassium chloride was added to precipitate solid powder (a mass ratio of potassium chloride to the primary condensation solution was 0.3:1); and
(6) the precipitated solid powder was dispersed in absolute ethanol, filtered, and freeze-dried to obtain a primary condensation product.

2. Secondary Condensation Reaction
(1) 9.58 g (0.02 mol) of the primary condensation product was dissolved in 20 mL of water to prepare an aqueous solution of the primary condensation product;
(2) 0.62 g (0.01 mol, 97%) ethylenediamine was added, the pH was regulated to 9.0 using a hydrochloric acid solution, then slowly added into the aqueous solution of the primary condensation product, the temperature was increased to 30-35° C., the pH was regulated to 4.5-5.0 using a saturated sodium bicarbonate solution, the reaction was continued at 30-35° C., and the pH value of the reaction solution was maintained at 4.5-5.0 using the sodium carbonate solution;
(3) the reaction endpoint was detected using the amino reagent to obtain a secondary condensation solution;
(4) the pH value of the secondary condensation solution was regulated to 2.0 using acetic acid, and then potassium chloride was added to precipitate solid powder (a mass ratio of potassium chloride to the secondary condensation solution was 0.3:1); and
(5) the precipitated solid powder was dispersed in absolute ethanol, filtered, and freeze-dried to obtain a secondary condensation product.

3. Diazotization-Coupling Reaction
(1) 50 g of 49% (w/w) sulfuric acid solution was added into a 250 mL three-necked flask, 4.38 g (0.02 mol) of 2-amino-5,6-dichlorobenzothiazole was slowly added, and stirred for 1 h below 50° C. to fully dissolve it;
(2) 6.99 g (0.022 mol) 40% (w/w) nitrosylsulfuric acid solution was slowly added dropwise below 0-5° C., and the reaction was finished in 4 h;
(3) sulfamic acid was added to eliminate excess nitrous acid to obtain a heterocyclic primary arylamine diazo salt;
(4) 0.01 mol 10.09 g of the secondary condensation product was dissolves in 20 mL of water, the temperature was reduced to 10-15° C., and 0.02 mol of the prepared heterocyclic primary arylamine diazo salt was slowly added, the reaction was continued for 2 h at 10-15° C., the pH was regulated to 6, the reaction was continued, and the reaction endpoint was detected using H acid (1-amino-8-hydroxy-3,6-sodium naphthalenedisulfonic acid); and
(5) after the reaction was finished, the pH chromotropic reactive dye was obtained after salting out, suction filtration, ethanol washing and drying.

Figure 43:
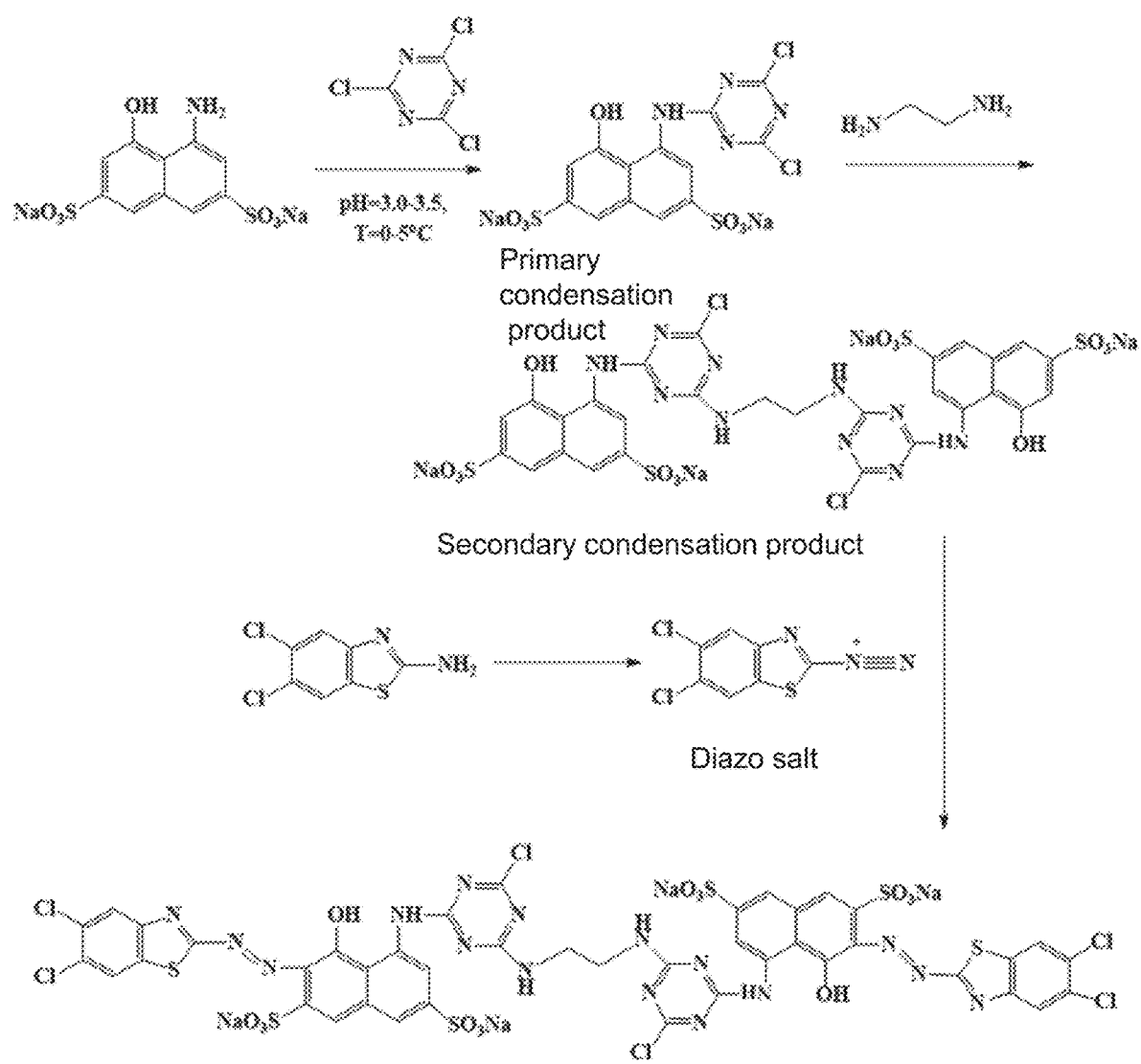
FIG. 43 illustrates a synthetic pathway of the reactive dye of Example 4.

The synthetic pathway of the double-chromosome pH chromotropic reactive dye is shown in FIG. 43. The structural formula of the pH chromotropic reactive dye is as follows:

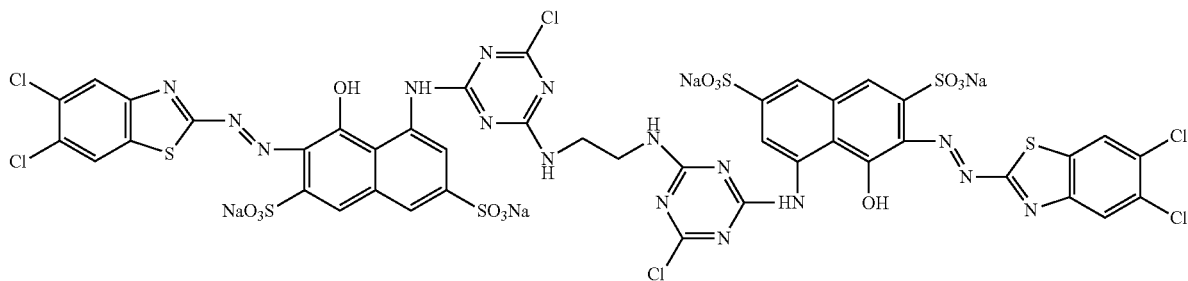

The structural characterization is as follows:
$^1$H-NMR (400 MHz, DMSO-d6): δ 9.43 (s, 2H, —NH—), 9.01 (s, 2H, —OH), 8.18 (s, 4H, hydrogen on Ar—H and naphthalene ring), 8.07 (s, 2H, Ar—H), 7.52 (s, 2H, hydrogen on the naphthalene ring), 7.47 (s, 2H, hydrogen on the naphthalene ring), 7.01 (s, 2H, —NH), 3.47 (m, 4H, HNCH$_2$CH$_2$NH).

Figure 13:
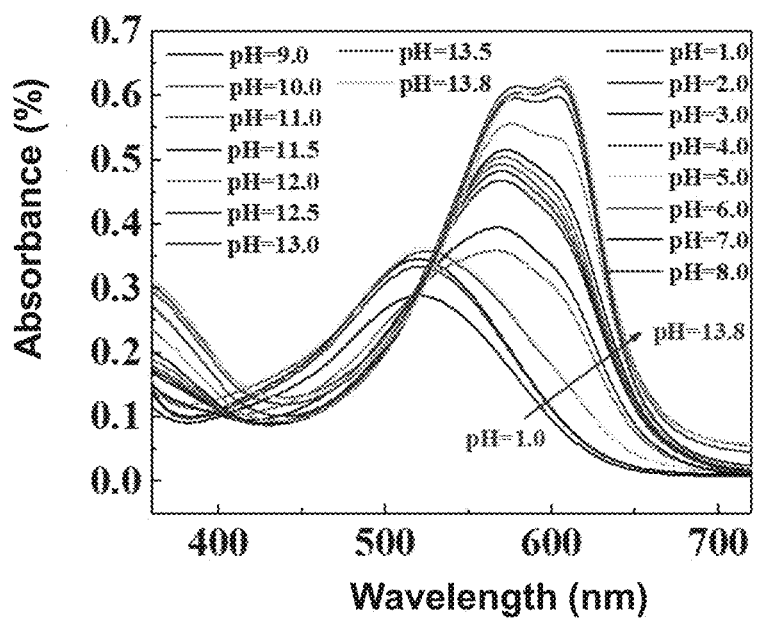
FIG. 13 is a spectrum curve illustrating a dye in Example 4 under different pH conditions (pH=1-13.8).
Figure 14:
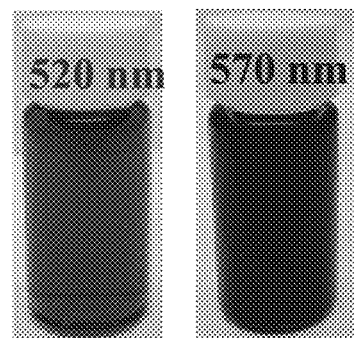
FIG. 14 is an optical picture of a dyeing solution after color changing in Example 4.

The obtained pH chromotropic reactive dye was subjected to a performance test, and the test results are as follows:

The spectral curves of the dye in Example 4 under different pH conditions (pH=1-13.8) are in FIG. 13, and the optical picture of the dye solution is in FIG. 14. It can be seen from FIG. 13 and FIG. 14 that: when the pH value of the solution is greater than or equal to 6.0, the solution is purple (the maximum absorption wavelength is 570 nm), and when the solution pH value is less than 6.0, the solution is red (the maximum absorption wavelength is 520 nm).

Figure 15:
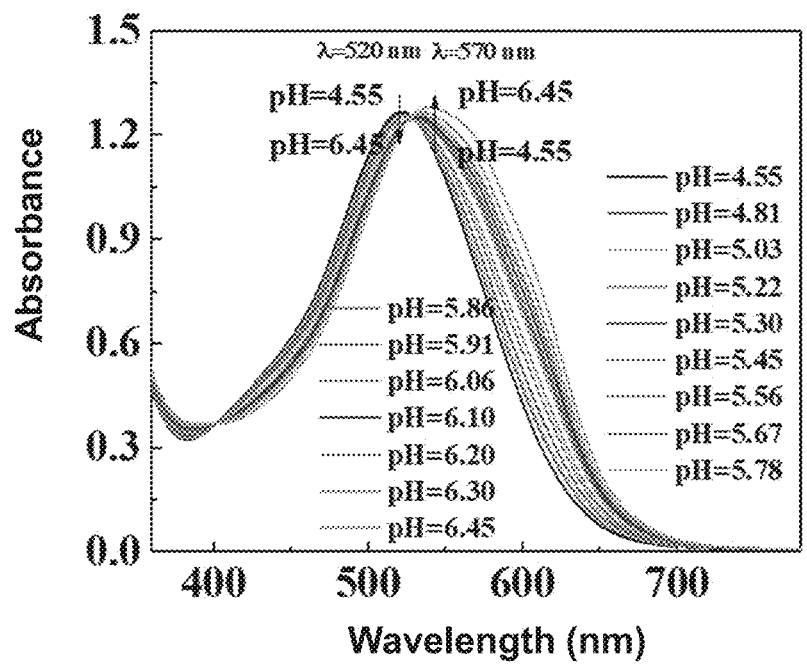
FIG. 15 is a spectrum curve illustrating the dye in Example 4 under different pH conditions (pH=4.55-6.45).

The spectral curves of the dye in Example 4 under different pH conditions (pH=4.55-6.45) are in FIG. 15. It can be seen from FIG. 15 that when the pH value of the solution is 5.03, the maximum absorption wavelength of the solution is 520 nm, and when the pH value of the solution is 6.20, the solution is purple, and the maximum absorption wavelength is 570 nm, which represents that the maximum absorption wavelength of the solution changes by 50 nm within 1.17 pH units of the dye, and thus the chromotropic precision of the dye is relatively high.

Figure 16:
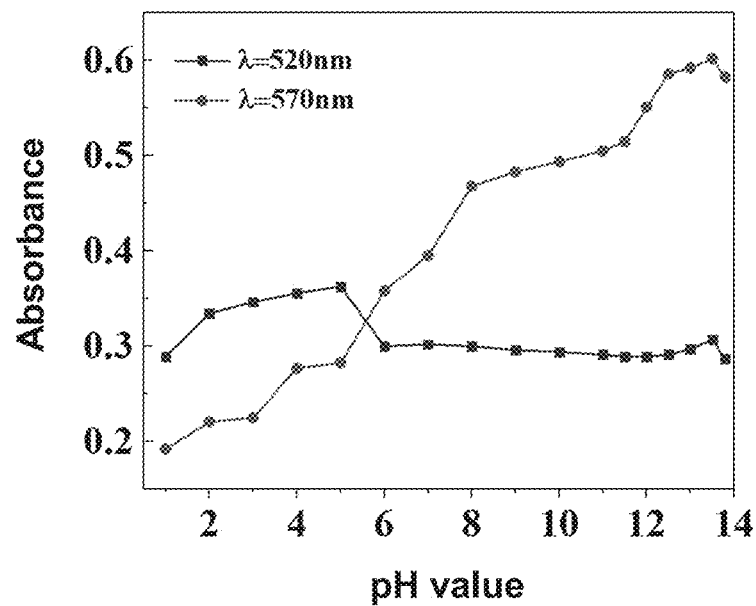
FIG. 16 illustrates a variation of an absorbance at a maximum absorption wavelength of a solution with a pH value before and after color changing of a dye in Example 4.
Figure 17:
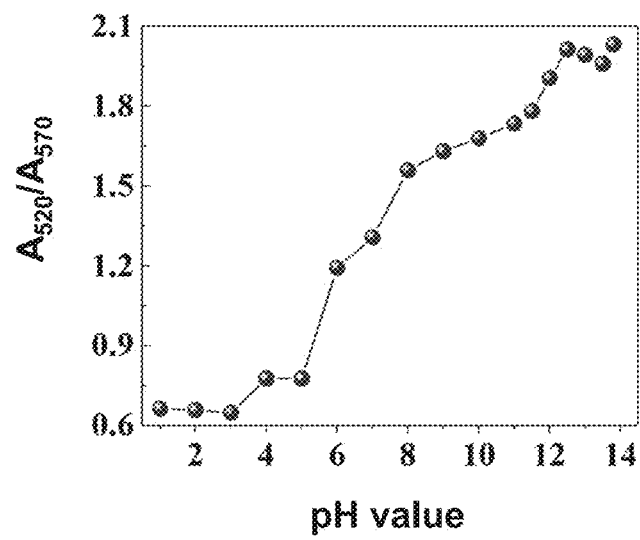
FIG. 17 illustrates a variation of an absorbance ratio of a solution with a pH value before and after color changing of the dye in Example 4.

A variation of a ratio of an absorbance at the maximum absorption wavelength with the pH value before and after color changing of the dye inf Example 4 is in FIG. 16 and FIG. 17. It can be seen from FIG. 16 and FIG. 17 that the pH value at the chromotropic isoelectric point (the absorbance value of the solution before and after color changing) of the solution is 5.66.

Example 5

1. Primary Condensation Reaction was the Same as 1 of Example 4
2. Secondary Condensation Reaction was the Same with 2 of Example 4
3. Diazotization-Coupling Reaction
    (1) 15.6 g of 98% (w/w) sulfuric acid was added into a 250 mL three-neck flask, 3.9 g (0.02 mol) of 3-amino-5-nitrobenzisothiazole was slowly added, and stirred for 1 h below 50° C. to fully dissolve it;
    (2) 6.99 g (0.022 mol) 40% (w/w) nitrosyl sulfuric acid solution dropwise below 0° C., 3.90 g of glacial acetic acid was slowly added dropwise at 0-5° C., and reacted for 4 h;
    (3) after the reaction was finished, sulfamic acid was added to eliminate excess nitrous acid to obtain a heterocyclic primary arylamine diazo salt;
    (4) 0.01 mol 10.09 g of the secondary condensation product was dissolved in 20 mL of water, the temperature was reduced to 10-15° C., and 0.02 mol of the prepared heterocyclic primary arylamine diazo salt was slowly added, the reaction was continued for 2 h at 10-15° C., the pH was regulated to 6, the reaction was continued, and a reaction endpoint was detected using (1-amino-8-hydroxy-3,6-sodium naphthalenedisulfonic acid); and
    (5) after the reaction was finished, the pH chromotropic reactive dye was obtained after salting out, suction filtration, ethanol washing and drying.

Figure 18:
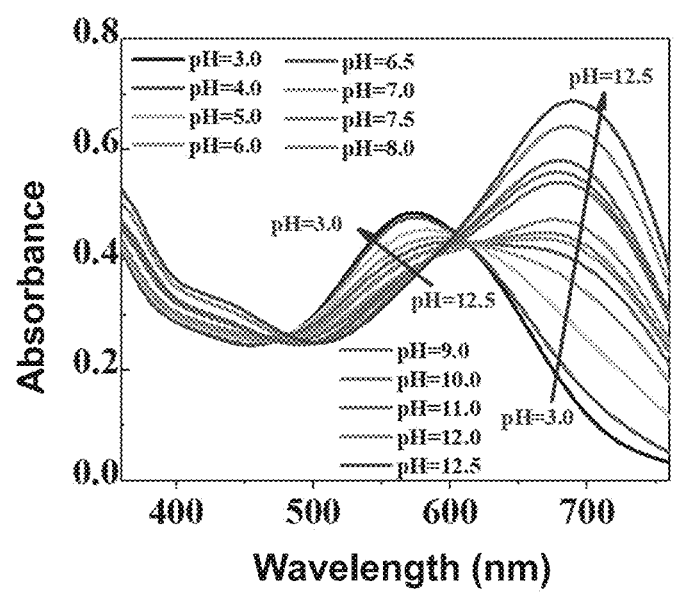
FIG. 18 is spectrum curves of a dye in Example 5 under different pH conditions (pH=3-12.5).
Figure 19:
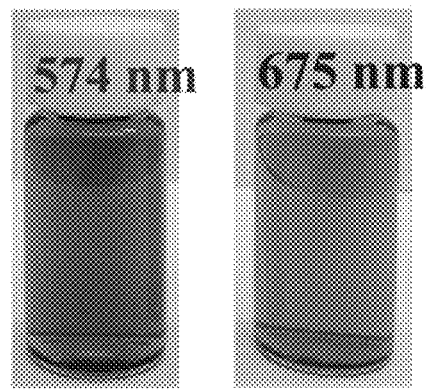
FIG. 19 is an optical picture of a dyeing solution after color changing in Example 5.
Figure 44:
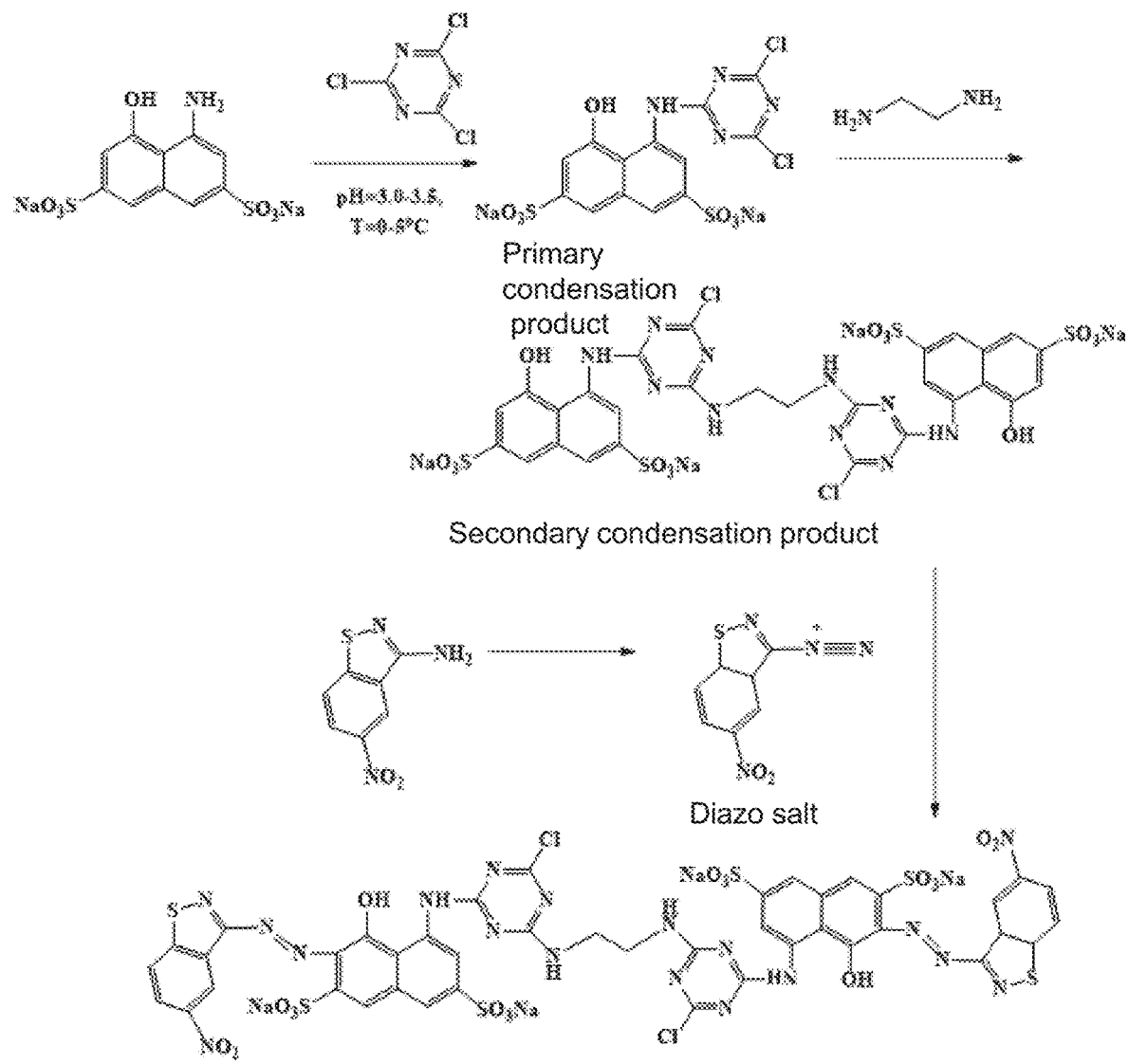
FIG. 44 illustrates a synthetic pathway of the reactive dye of Example 5.

The synthetic pathway of the pH chromotropic reactive dye is shown in FIG. 44. The structural formula of the obtained double-chromosome pH chromotropic reactive dye is as follows:

The obtained double-chromosome pH chromotropic reactive dye was subjected to a performance test, and the test results are as follows:

The spectral curves of the dye in Example 5 under different pH conditions (pH=3-12.5) are in FIG. 18, and the optical picture of the dye is in FIG. 19. It can be seen from FIG. 18 and FIG. 19 that when the pH value of the solution is greater than or equal to 6.5, the solution is green (the maximum absorption wavelength is 675 nm), and when the solution pH value is less than 6.5, the solution is purple (the maximum absorption wavelength is 574 nm).

Figure 20:
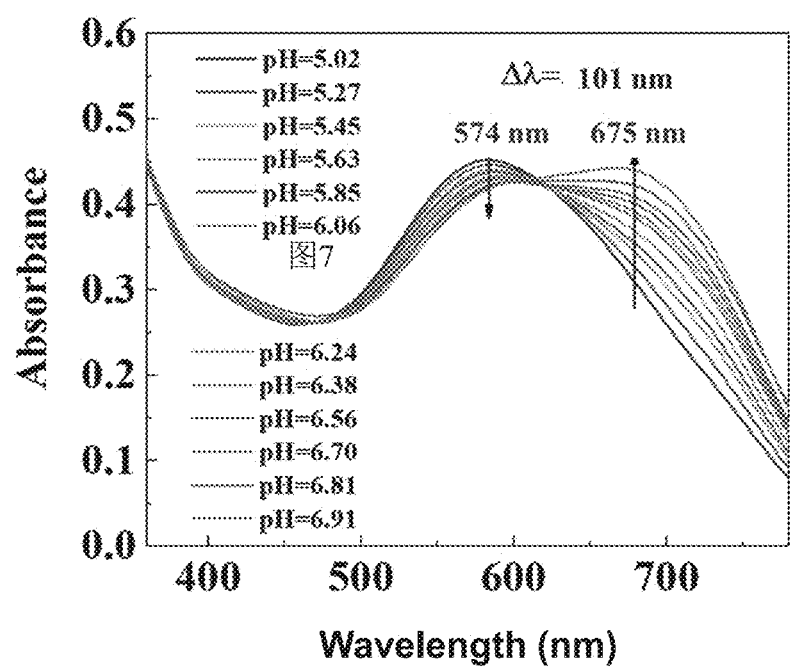
FIG. 20 is spectrum curves of the dye in Example 5 under different pH conditions (pH=5.02-6.91).

The spectral curves of the dye in Example 5 under different pH conditions (pH=5.02-6.91) are in FIG. 20. It can be seen from FIG. 20 that when the pH value of the solution is 5.63, the solution is purple, and the maximum absorption wavelength of the solution is 574 nm; and when the pH value of the solution is 6.56, the solution is green, and the maximum absorption wavelength is 675 nm, which represents that the maximum absorption wavelength of the solution changes by 101 nm within 0.93 pH units of the dye, and the chromotropic precision of the dye is relatively high.

Figure 21:
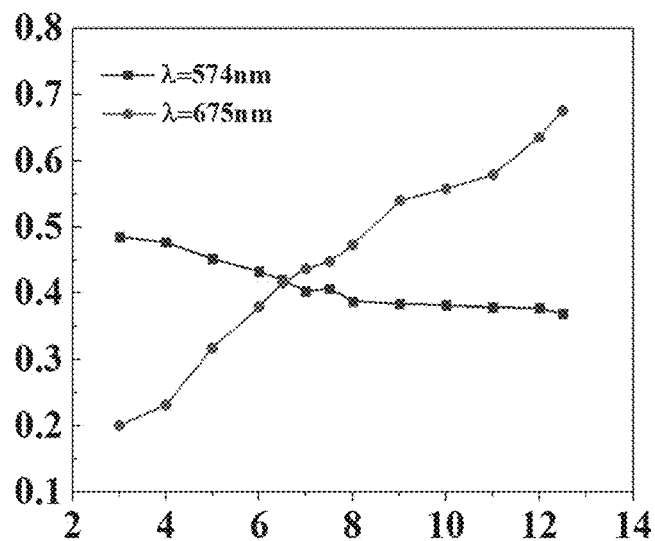
FIG. 21 illustrating a variation of an absorbance at a maximum absorption wavelength of a solution with a pH value before and after color changing of the dye in Example 5.
Figure 22:
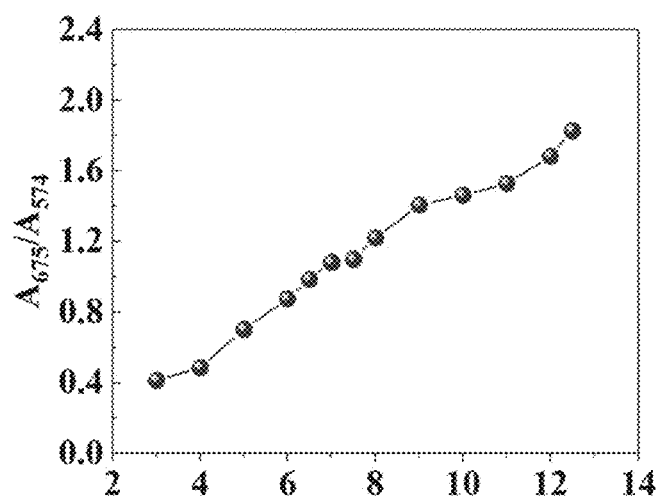
FIG. 22 illustrates a variation of an absorbance ratio of a solution with a pH value before and after color changing of the dye in Example 5.

A variation of a ratio of absorbance at the maximum absorption wavelength with the pH value before and after color changing of the dye in Example 5 is in FIG. 21 and FIG. 22. It can be seen from FIG. 21 and FIG. 22 that the pH value at the chromotropic isoelectric point (absorbance value of the solution before and after color changing) of the solution is 6.24.

Example 6 Dyeing the Cotton Fabrics Using Reactive Dyes

A preparation method of a color-changing cotton fabric (140 g/m², pure cotton bleached knitted fabric) is descripted as follows.
1. Printing color paste formula: 40 g/L of dye, 60 g/L of raw paste (sodium alginate aqueous solution with a mass concentration of 4%), 15 g/L of anti-dyeing salt S, 60 g/L of urea, 25 g/L of sodium carbonate, and adding water to make up 1000 g.

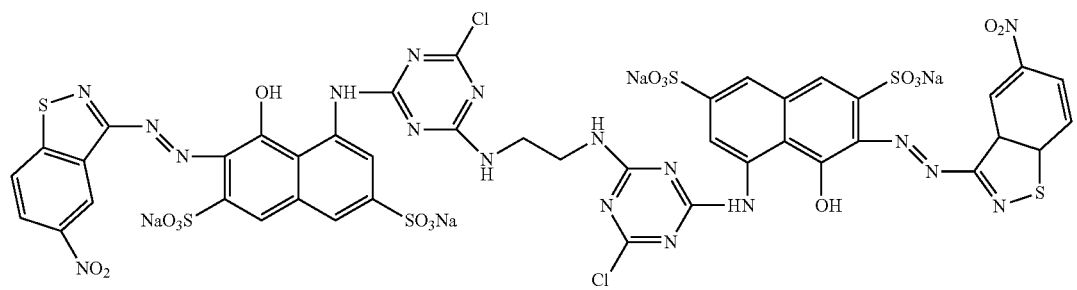

The structural characterization is as follows:

¹H-NMR (400 MHz, DMSO-d6): δ 9.43 (s, 2H, —NH—), 9.00 (s, 2H, —OH), 8.36, 8.34 (d, 4H, Ar—H), 8.26 (s, 2H, Ar—H), 8.18 (s, 2H, Ar—H), 7.52 (s, 2H, hydrogen on the naphthalene ring), 7.47 (s, 2H, hydrogen on the naphthalene ring), and 7.01 (s, 2H, —NH), 3.47 (m, 4H, HNCH2CH2NH).

2. Printing process: printing→pre-baking (100° C., 4 min)→steaming (105° C., 6 min)→cold water washing→soaping (98° C., 10 min)→reduction cleaning (85° C., 15 min)→hot water washing (80° C.)→cold water washing→drying.

The cotton fabric obtained in Example 3 was soaked in sweat simulation solutions with different pH values (as in Table 3) for performance testing. The test results are in Table 4 and FIGS. 23-26:

TABLE 3

Sweat simulation solutions with different pH values

| Component | Acid sweat simulation solution | Alkaline sweat simulation solution |
|---|---|---|
| L-histidine hydrochloride monohydrate | 0.5 g/L | 0.5 g/L |
| Sodium chloride | 5 g/L | 5 g/L |
| Sodium dihydrogen phosphate dihydrate | 2.2 g/L | — |
| Disodium hydrogen phosphate dihydrate | — | 2.5 g/L |
| 0.1 mol/L sodium hydroxide solution | Regulating pH value to 5.5 | Regulating pH value to 8.0 |

TABLE 4

Performance test results of printed fabric

| | Indicator | K/S | Color fixation rate | Water fastness/level | Rubbing fastness/level Dry | Rubbing fastness/level Wet | Fastness to sunlight/level |
|---|---|---|---|---|---|---|---|
| Dye of Example 4 | Acid sweat simulation solution | 12.51 | 63.26 | 4 | 4 | 3~4 | 3~4 |
| | Alkaline sweat simulation solution | 11.83 | | 4 | 4 | 4 | 3~4 |
| Dye of Example 5 | Acid sweat simulation solution | 15.17 | 58.63 | 4 | 4 | 3~4 | 4 |
| | Alkaline sweat simulation solution | 15.93 | | 4 | 4 | 4 | 4 |

It can be seen from Table 3 that the color fixation rates of the printed cotton fabric prepared by the dye in Example 4 and the dye in Example 5 all reached more than 55%, and the color fastness to washing, rubbing and sunlight all reached level 3-4 or above.

Figure 23:
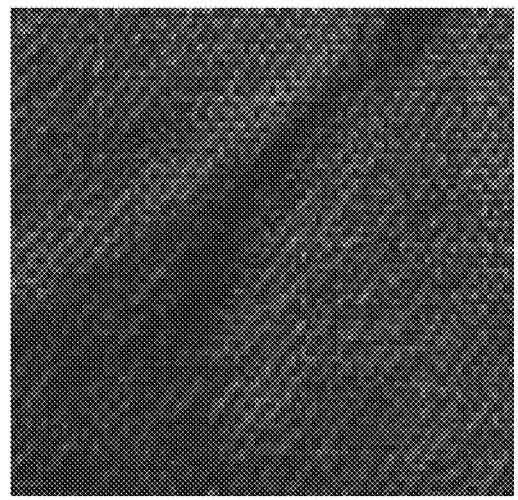
FIG. 23 illustrates a photograph of a printed cotton fabric using the dye in Example 4 under an acidic condition.
Figure 24:
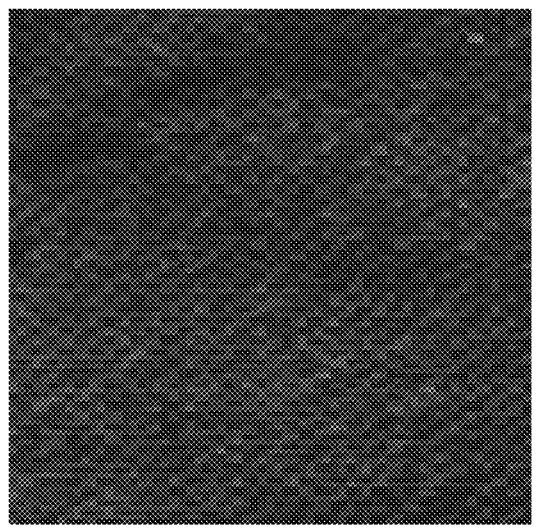
FIG. 24 illustrates a photograph of a printed cotton fabric using the dye in Example 4 under an alkaline condition.

It can be seen from FIGS. 23-24 that the printed cotton fabric prepared with the dye in Example 4 is red under an acid sweat condition, and purple under an alkaline sweat condition, which can be applied to human sweat detection.

Figure 25:
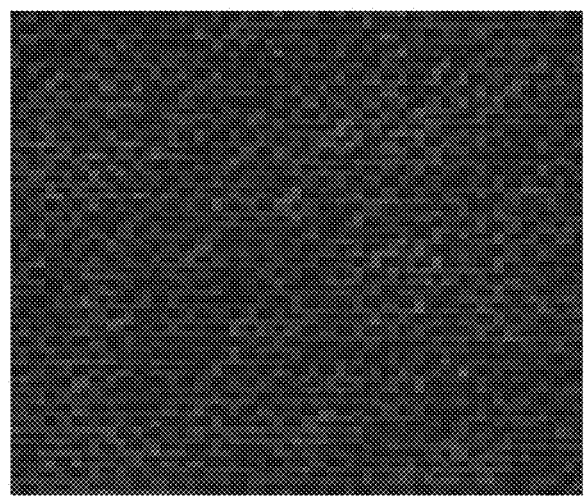
FIG. 25 illustrates a photograph of a printed cotton fabric using the dye in Example 5 under an acidic condition.
Figure 26:
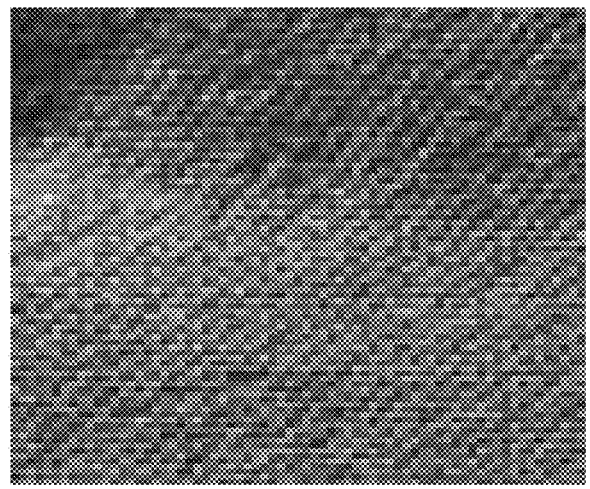
FIG. 26 illustrates a photograph of a printed cotton fabric using the dye in Example 5 under an alkaline condition.

It can be seen from FIGS. 25-26 that the printed cotton fabric prepared with the dye in Example 5 is blue under an acid sweat condition, and green under an alkaline sweat condition, which can be applied to human sweat detection.

Comparative Example 7

A preparation method of a color-changing dye comprises:

1. Primary Condensation Reaction Being the Same as 1 of Example 4

2, Secondary Condensation Reaction Being the Same with 2 of Example 4

3. Diazotization-Coupling Reaction
   (1) adding 18.45 g of 98% (w/w) sulfuric acid solution into a 250 mL three-necked flask, slowly adding 4.14 g (0.02 mol) of 2,6-dichloro-4-nitroaniline, and stirring for 1 h below 50° C. to fully dissolve it, and slowly adding 6.99 g (0.022 mol) of 40% (w/w) nitrosylsulfuric acid solution dropwise below 0° C., wherein the reaction was finished in 3-4 h;
   (2) adding sulfamic acid to eliminate excess nitrous acid to obtain a heterocyclic primary arylamine diazo salt;
   (3) dissolving 0.01 mol 10.09 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting a reaction endpoint using H acid (1-amino-8-hydroxy-3,6-sodium naphthalenedisulfonic acid); and
   (4) after the reaction was finished, obtaining the pH chromotropic dye after salting out, suction filtration, ethanol washing and drying.

Figure 45:
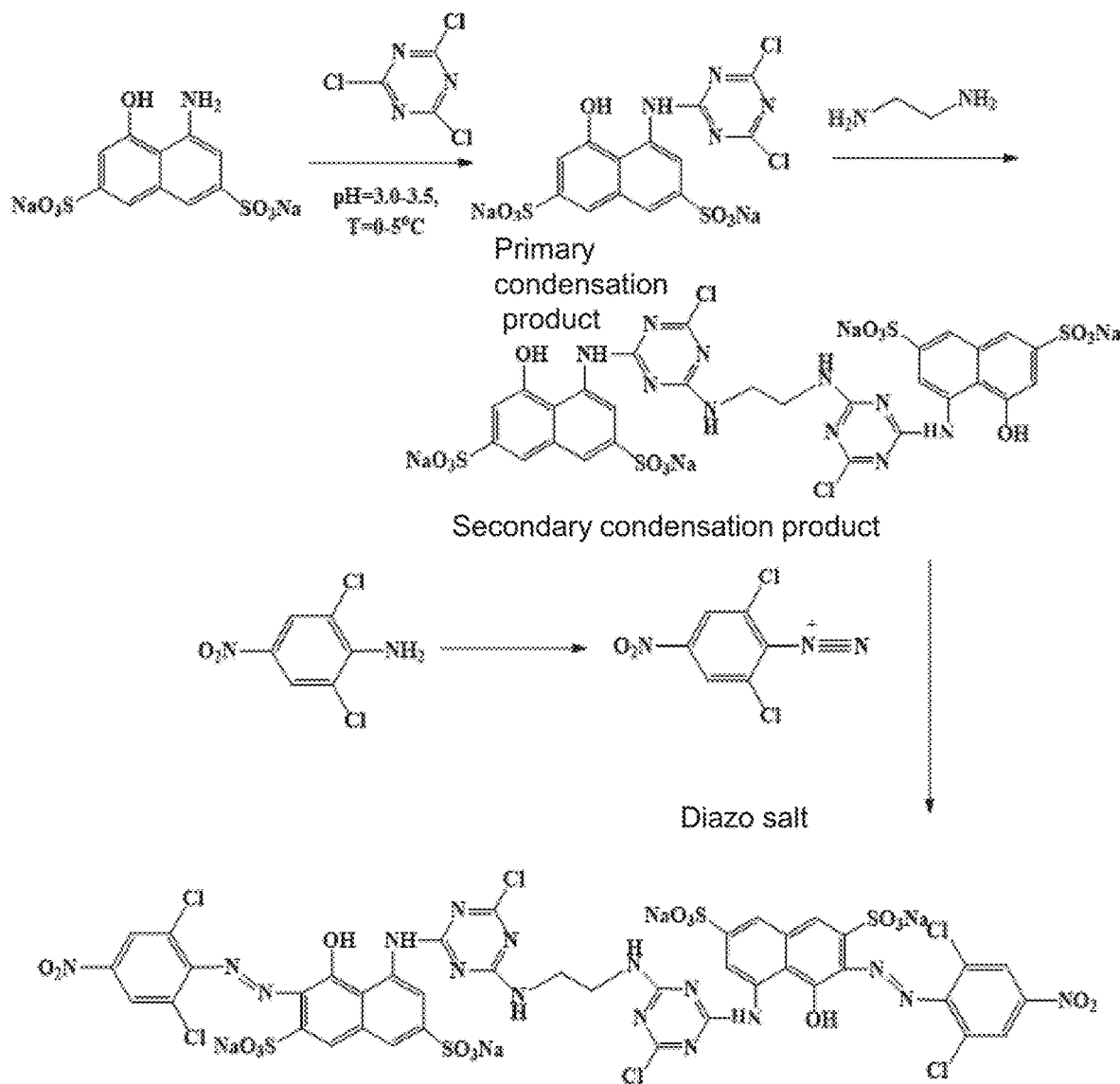
FIG. 45 illustrates a synthetic pathway of the reactive dye of Comparative Example 7.

The synthetic pathway of the dye is shown in FIG. 45. The structural formula of the obtained pH chromotropic dye is as follows:

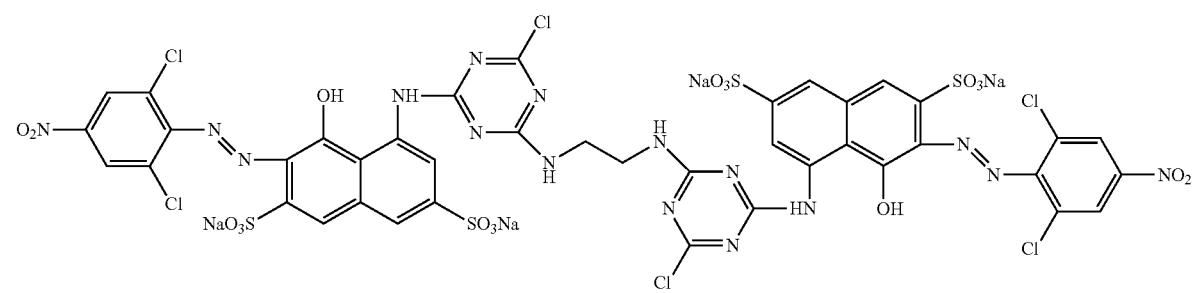

The dye obtained in Comparative Example 7 was printed on the cotton fabric according to the method of Example 6, and the color fixation rate of the dye on the cotton fabric was only 39.36%.

Comparative Example 8

A preparation method of a dye comprises: Diazo salt
1. Primary Condensation Reaction
   (1) adding 3.74 g (0.02 mol) of cyanuric chloride and 0.19 g of sodium butylnaphthalene sulfonate into 15 g of ice-water mixture, and fully pulping for 1 h at 0-5° C. to obtain a cyanuric chloride solution;

(2) adding 4.78 g (0.02 mol) of 2-amino-5-naphthol-7-sulfonic acid to 15 g of water, regulating the pH to 6.0-6.5 using sodium carbonate, and fully dissolve to obtain a 2-amino-5-naphthol-7-sodium sulfonate solution;
(3) then mixing the 2-amino-5-naphthol-7-sodium sulfonate solution with the cyanuric chloride solution, regulating the pH to 3.0-3.5 using a saturated sodium bicarbonate solution, continuing the reaction at 0-5° C., and maintaining the pH value of the reaction solution at 3.0-3.5 using a sodium carbonate solution;
(4) detecting a reaction endpoint using an amino reagent to obtain a primary condensation solution;
(5) regulating the pH value of the primary condensation solution to 1.5 using acetic acid, and then adding a certain amount of potassium chloride to precipitate solid powder (a mass ratio of potassium chloride to the primary condensation solution was 0.3:1); and
(6) dispersing the precipitated solid powder in absolute ethanol, filtering, and freeze-drying to obtain a primary condensation product.

2. Secondary Condensation Reaction
(1) dissolving 9.44 g (0.02 mol) of the primary condensation product in 20 mL of water to prepare an aqueous solution of the primary condensation product;
(2) adding 0.62 g (0.01 mol, 97%) ethylenediamine, regulating the pH to 9.0 using ah hydrochloric acid solution, then slowly adding to the aqueous solution of the primary condensation product, increasing the temperature to 30-35° C., regulating the pH of the sodium solution to 4.5-5.0 using the saturated hydrogen carbonate solution, continuing the reaction at 30-35° C., and maintaining the pH value of the reaction solution at 4.5-5.0 using the sodium carbonate solution;
(3) detecting the reaction endpoint using the amino reagent to obtain a secondary condensation solution;
(4) regulating the pH value of the secondary condensation solution to 2.0 using acetic acid, and then adding a certain amount of potassium chloride to precipitate solid powder (a mass ratio of potassium chloride to the secondary condensation solution was 0.3:1); and
(5) dispersing the precipitated solid powder in absolute ethanol, filtering, and freeze-drying to obtain a secondary condensation product.

3. Diazotization-Coupling Reaction
(1) adding 50 g of 49% (w/w) sulfuric acid solution into a 250 mL three-necked flask, slowly adding 4.38 g (0.02 mol) of 2-amino-5,6-dichlorobenzothiazole, and stirring for 1 h below 50° C. to fully dissolve it;
(2) slowly adding 6.99 g (0.022 mol) of 40% (w/w) nitrosylsulfuric acid solution dropwise below 0-5° C., wherein the reaction was finished in 4 h;
(3) adding sulfamic acid to eliminate excess nitrous acid to obtain a heterocyclic primary arylamine diazo salt;
(4) dissolving 0.01 mol 9.07 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and
(5) after the reaction was finished, obtaining the double-chromosome pH chromotropic reactive dye after salting out, suction filtration, ethanol washing and drying. The preparation method of the pH chromotropic dye comprises the following operations.

Figure 46:
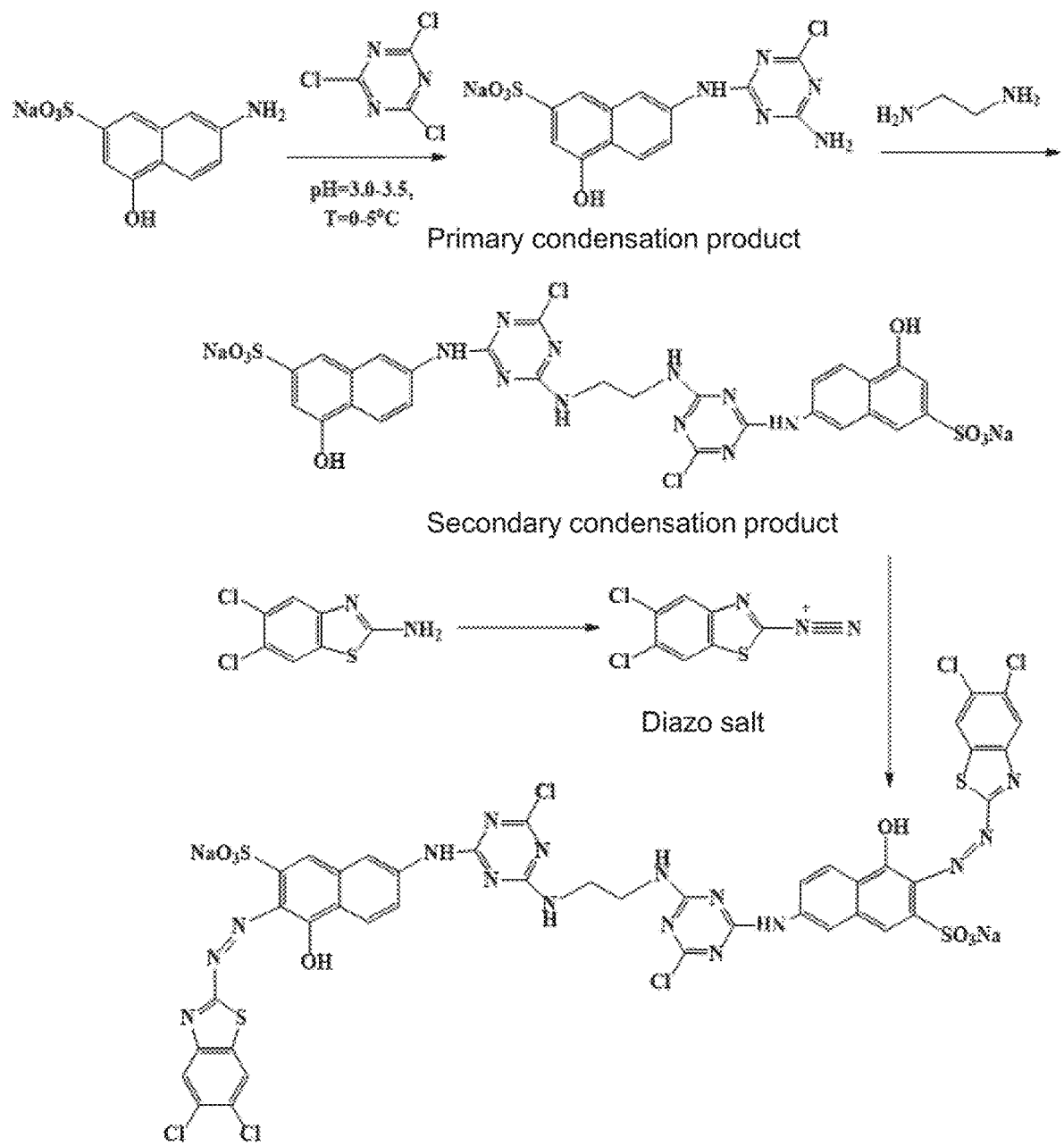
FIG. 46 illustrates a synthetic pathway of the reactive dye of Comparative Example 8.

The synthetic pathway of the dye is shown in FIG. 46. The structural formula of the obtained dye is as follows:

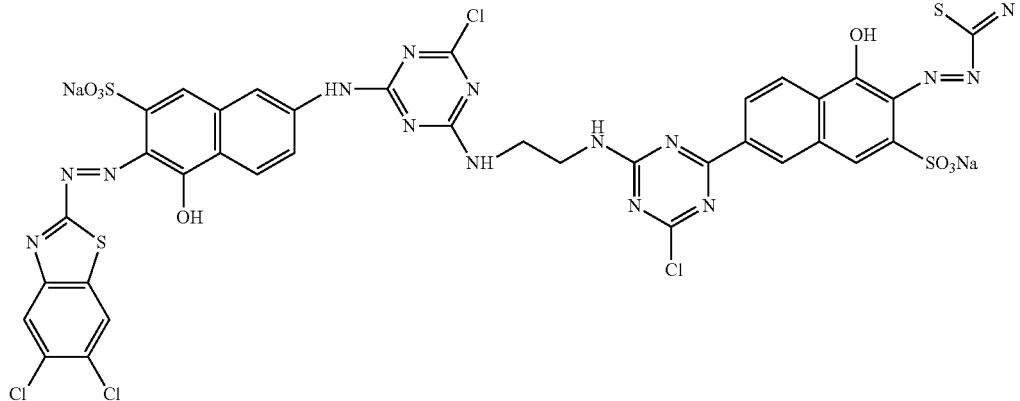

The dye prepared in Comparative Example 8 was printed on the cotton fabric according to the method of Example 6, and the color fixation rate of the dye on the cotton fabric was only 39.36%.

Example 7

A preparation method of a reactive dye comprises:
1. Primary Condensation Reaction
(1) adding 3.74 g (0.02 mol) of cyanuric chloride and 0.19 g of sodium butylnaphthalene sulfonate into 15 g of ice-water mixture, which are fully beated for 1 h at 0-5° C. to obtain a cyanuric chloride solution;
(2) adding 4.93 g (0.02 mol, 97%) 2-amino-5-naphthol-7-sulfonic acid into 10 g of water, regulating the pH to 6.0-6.5 using a saturated sodium carbonate solution, and fully dissolving to obtain a 2-amino-Sodium 5-naphthol-7-sodium sulfonate solution;

(3) then mixing 2-amino-5-naphthol-7-sodium sulfonate and the cyanuric chloride solution, regulating the pH to 3.0-3.5 using the saturated sodium bicarbonate solution, continuing the reaction at 0-5° C., and detecting a reaction endpoint using an amino reagent to obtain a primary condensation solution;

(4) regulating the pH value of the primary condensation solution to 1.5 with acetic acid, and then adding potassium chloride to precipitate solid powder (a mass ratio of potassium chloride to the primary condensation solution was 0.3:1); and (5) dispersing the precipitated solid powder in absolute ethanol, filtering, and freeze-drying to obtain a primary condensation product.

2. Secondary Condensation Reaction (1) dissolving 3.74 g (0.01 mol) of the primary condensation product in 20 mL of water to prepare an aqueous solution of the primary condensation product;

(2) adding 3.19 g (0.01 mol) of 1-amino-8-hydroxy-3,6-naphthalenedisulfonic acid into 10 g of water, regulating the pH to 6.0-6.5 using the saturated sodium carbonate solution to obtain a 1-amino-8-hydroxy-3,6-naphthalenedisulfonic acid solution;

(3) then adding the 1-amino-8-hydroxy-3,6-naphthalenedisulfonic acid solution into the aqueous solution of the primary condensation product, increasing the temperature to 30-35° C., regulating the pH to 4.5-5.0, continuing the reaction at 30-35° C., and maintaining the pH value of the reaction solution at 4.0-4.5 using a sodium carbonate solution;

(4) detecting the reaction endpoint using the amino reagent to obtain a secondary condensation solution; regulating the pH value of the secondary condensation solution to 2.0 using acetic acid, and then adding a certain amount of potassium chloride to precipitate solid powder (a mass ratio of potassium chloride to the secondary condensation solution was 0.3:1); and (5) dispersing the precipitated solid powder in absolute ethanol, filtering, and freeze-drying to obtain a secondary condensation product.

3. Diazotization-Coupling Reaction (1) adding 15.6 g of 98% (w/w) sulfuric acid solution into a 250 mL three-necked flask, slowly adding 3.9 g (0.02 mol) 3-amino-5-nitrobenzisothiazole, and stirring for 1 h below 50° C. to fully dissolve it;

(2) slowly adding 6.99 g (0.022 mol) 40% (w/w) nitrosylsulfuric acid solution dropwise below 0° C., and slowly adding 3.9 g of glacial acetic acid dropwise at 0-5° C., wherein the reaction was finished in 3-4 h;

(3) adding sulfamic acid to eliminate excess nitrous acid to obtain a heterocyclic primary arylamine diazo salt;

(4) dissolving 0.01 mol 7.22 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and (5) after the reaction was finished, obtaining the pH chromotropic reactive dye for sweat detection after salting out, suction filtration, ethanol washing and drying.

Figure 47:
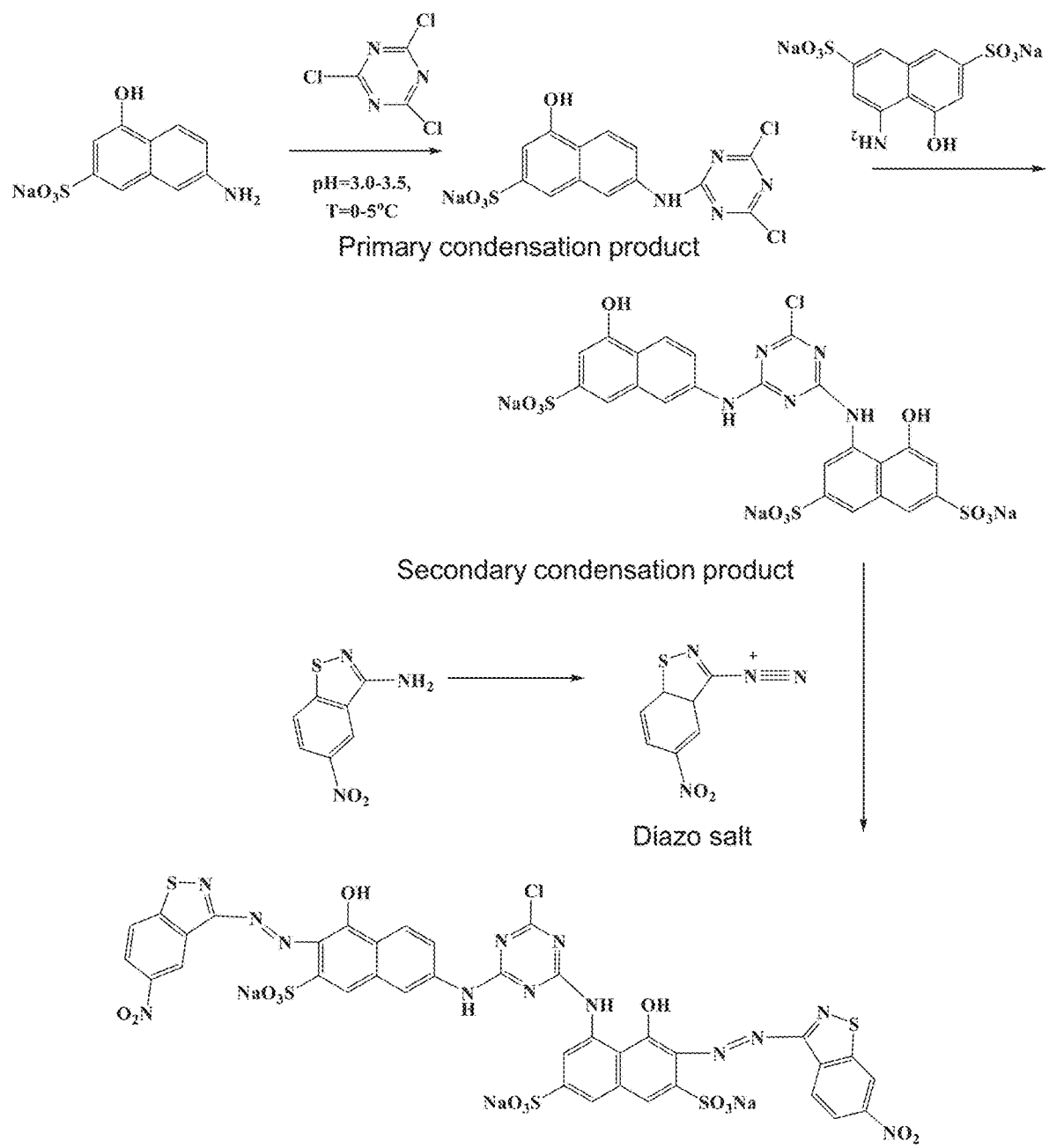
FIG. 47 illustrates a synthetic pathway of the reactive dye of Example 7.

The synthetic pathway of the reactive dye is shown in FIG. 47. The structural formula of the obtained reactive dye is as follows:

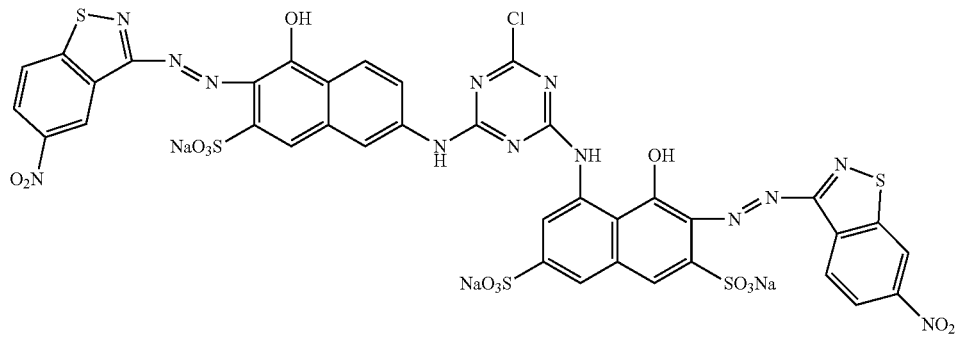

The structural characterization is as follows:

$^1$H-NMR (400 MHz, DMSO-d6): δ 9.43 (s, 2H, —NH—), 9.00 (s, 2H, —OH), 8.36, 8.34 (d, 2H, Ar—H), 8.26 (s, 2H, Ar—H), 8.19, 8.17 (d, 2H, Ar—H), 8.05 (d, 1H, hydrogen on the naphthalene ring), 7.82 (s, 1H, hydrogen on the naphthalene ring), 7.79 (d, 1H, hydrogen on the naphthalene ring), 7.52 (s, 1H, hydrogen on the naphthalene ring), 7.47 (s, 1H, hydrogen on the naphthalene ring), 7.4 Diazo salt ydrogen on the naphthalene ring), and 7.32 (s, 1H, hydrogen on the naphthalene ring).

Figure 27:
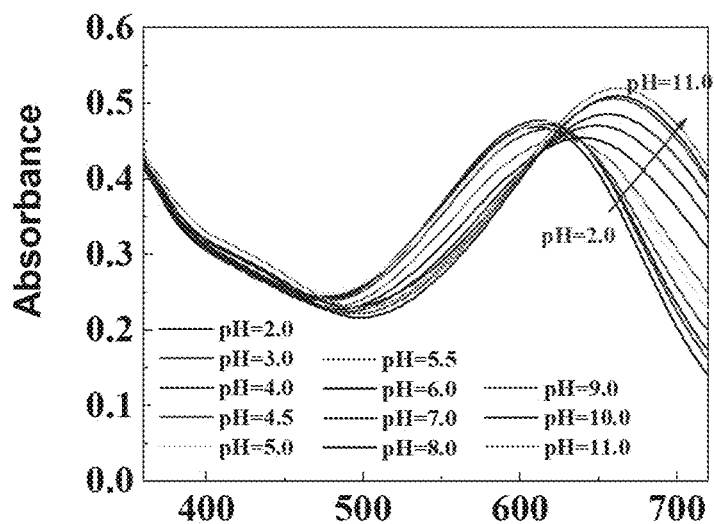
FIG. 27 is spectrum curves of a dye in Example 7 under different pH conditions (pH=2-11).
Figure 28:
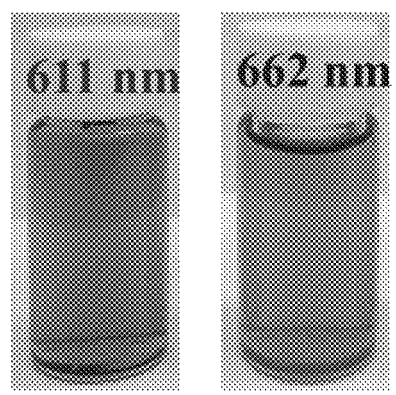
FIG. 28 is an optical picture of a dyeing solution after color changing in Example 7.

The obtained reactive dye was subjected to a performance test. The test results are as follows:

The spectral curves of the dye in Example 7 under different pH conditions (pH=2-11) are in FIG. 27, and the optical picture of the dye is in FIG. 28. It can be seen from FIG. 27 and FIG. 28 that when the pH value of the solution is greater than or equal to 6.0, the solution is green (the maximum absorption wavelength is 662 nm), and when the solution pH value is less than 6.0, the solution is blue (the maximum absorption wavelength is 611 nm).

Figure 29:
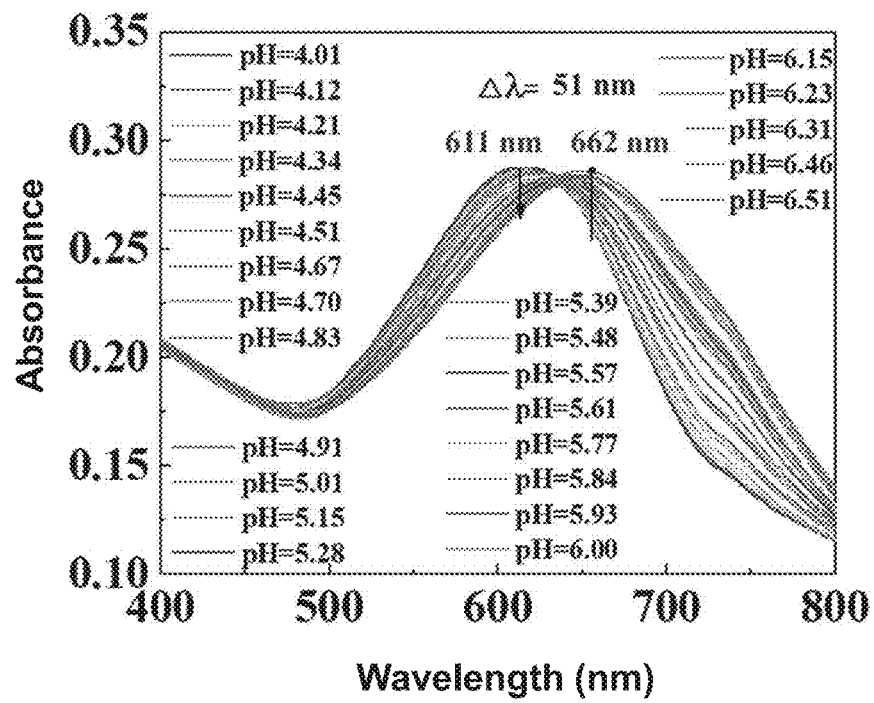
FIG. 29 is spectrum curves illustrating the dye in Example 7 under different pH conditions (pH=4.01-6.51).

The spectral curves of the dye in Example 7 under different pH conditions (pH=4.01~6.51) are in FIG. 29. It can be seen from FIG. 29 that when the pH value of the solution is 4.91, the solution is blue, and the maximum absorption wavelength of the solution is 611 nm; and when the pH value of the solution is 5.61, the solution is green, and the maximum absorption wavelength is 662 nm, which represents that the maximum absorption wavelength of the solution changes by 51 nm within 0.70 pH units of the dye, and the chromotropic precision of the dye is relatively high.

Figure 30:
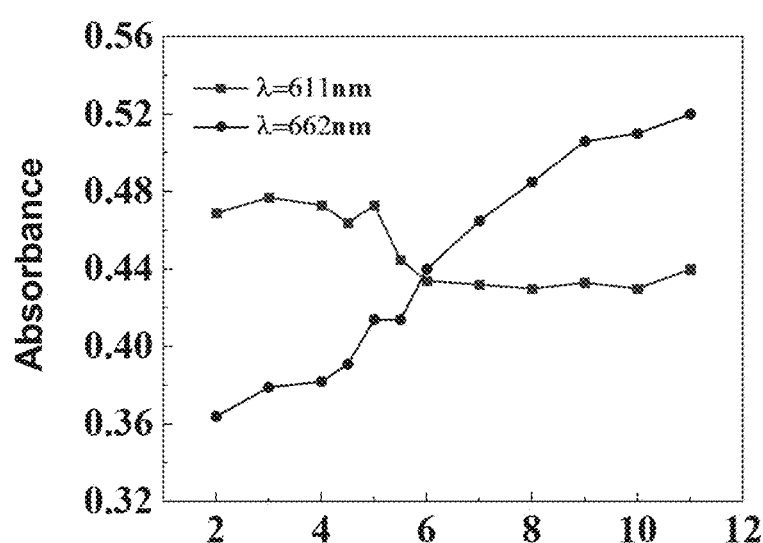
FIG. 30 illustrates a variation of an absorbance at a maximum absorption wavelength of a solution with a pH value before and after color changing of the dye in Example 7.
Figure 31:
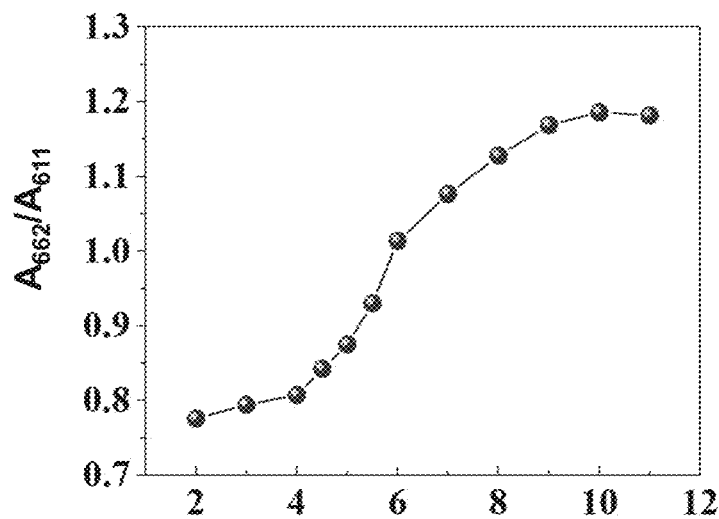
FIG. 31 illustrates a variation of an absorbance ratio of a solution with a pH value before and after color changing of the dye in Example 7.

A variation of an absorbance and an absorbance ratio at the maximum absorption wavelength with the pH value before and after color changing of the dye in Example 7 is in FIG. 30 and FIG. 31. It can be seen from FIG. 30 and FIG. 31 that the pH value at the color-changing isoelectric point (absorbance value of the solution when the color is changed) of the solution is 6.00.

Example 8

1. Primary Condensation Reaction was the Same as 1 of Example 7
2. Secondary Condensation Reaction was the Same as 2 of Example 7
3. Diazotization-Coupling Reaction
    (1) 50 g of 49% (w/w) sulfuric acid solution was added into a 250 mL three-necked flask, 4.38 g (0.02 mol) of 2-amino-5,6-dichlorobenzothiazole was slowly added, and stirred for 1 h below 50° C. to fully dissolve it;
    (2) 6.99 g (0.022 mol) of 40% (w/w) nitrosylsulfuric acid solution was slowly added dropwise below 0-5° C., and the reaction was finished in 4 h;
    (3) sulfamic acid was added to eliminate excess nitrous acid to obtain a heterocyclic primary arylamine diazo salt;
    (4) 0.01 mol 7.22 g of the secondary condensation product was dissolved in 20 mL of water, the temperature was reduced to 10-15° C., and the prepared heterocyclic primary arylamine diazo salt was slowly added, the reaction was continued for 2 h at 10-15° C., the pH was regulated to 6, the reaction was continued, and a reaction endpoint was detected using H acid (1-amino-8-hydroxy-3,6-sodium naphthalenedisulfonic acid); and
    (5) after the reaction was finished, the pH chromotropic reactive dye for sweat detection was obtained after salting out, suction filtration, ethanol washing and drying.

Figure 48:
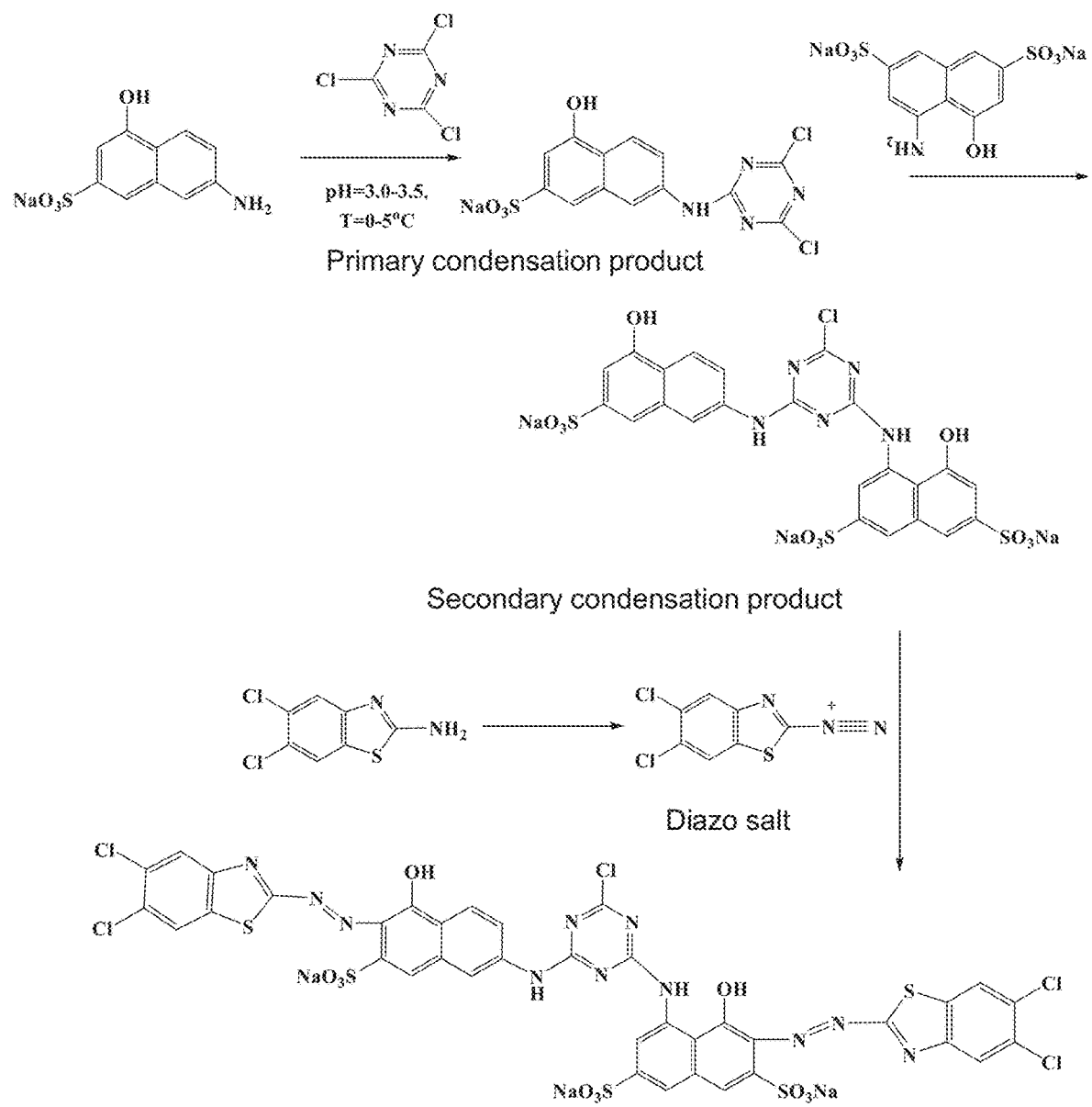
FIG. 48 illustrates a synthetic pathway of the reactive dye of Example 8.

The synthetic pathway of the reactive dye is shown in FIG. 48. The structural formula of the reactive dye is as follows:

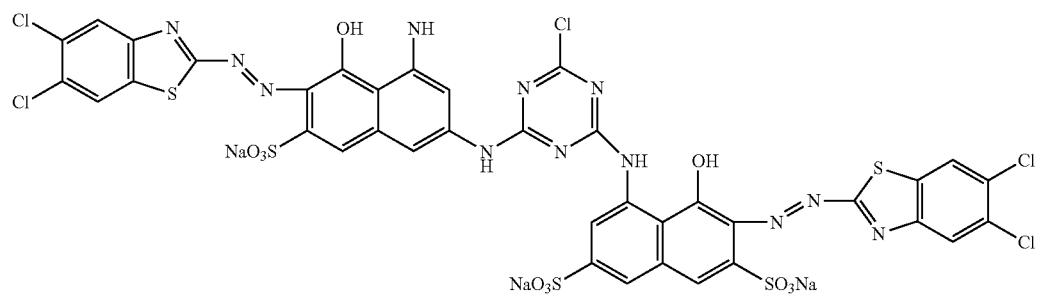

The structural characterization is as follows:

$^1$H-NMR (400 MHz, DMSO-d6): δ 9.43 (s, 2H, —NH—), 9.00 (s, 2H, —OH), 8.66, 8.64 (s, 2H, Ar—H), 8.31, 8.29 (d, 2H, Ar—H), 8.05 (d, 1H, hydrogen on naphthalene ring), 7.82 (s, 1H, hydrogen on naphthalene ring), 7.79 (d, 1H, hydrogen on naphthalene ring), 7.52 (s, 1H, hydrogen on naphthalene ring), 7.47 (s, 1H, hydrogen on naphthalene ring), 7.41 (s, 1H, hydrogen on naphthalene ring), and 7.32 (s, 1H, hydrogen on naphthalene ring).

Figure 32:
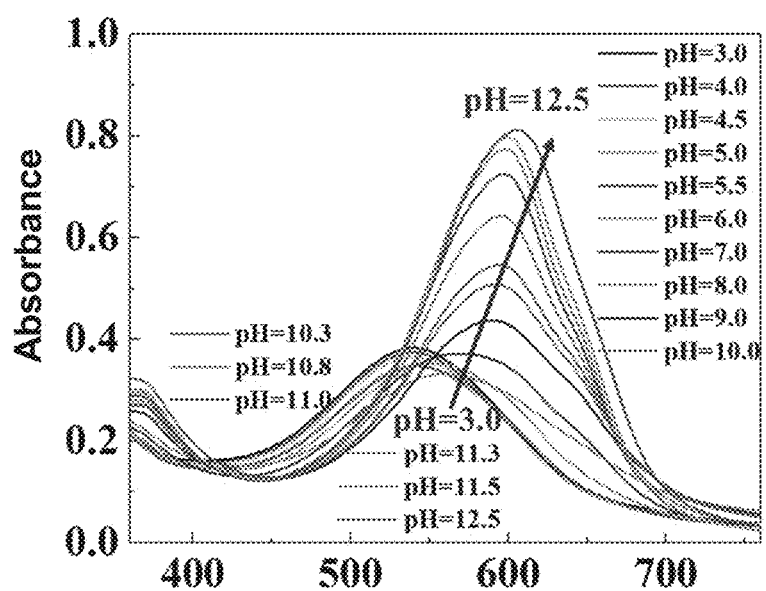
FIG. 32 is spectrum curves illustrating a dye in Example 8 under different pH conditions (pH=3-12.5).
Figure 33:
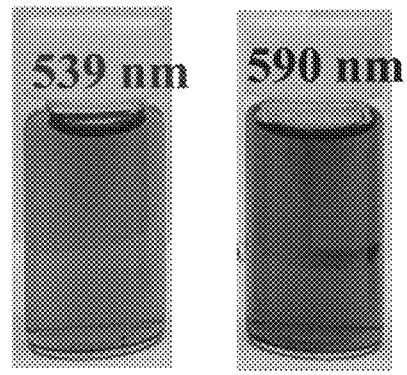
FIG. 33 is an optical picture of a dyeing solution after color changing in Example 8.

The obtained reactive dye was subjected to a performance test. The test results are as follows:

The spectral curves of the dye in Example 8 under different pH conditions (pH=2-11) are in FIG. 32, and the optical picture of the dye is in FIG. 33. It can be seen from FIG. 32 and FIG. 33 that when the pH value of the solution is greater than or equal to 7.0, the solution is blue (the maximum absorption wavelength is 590 nm), and when the solution pH value is less than 7.0, the solution is red (the maximum absorption wavelength is 539 nm).

Figure 34:
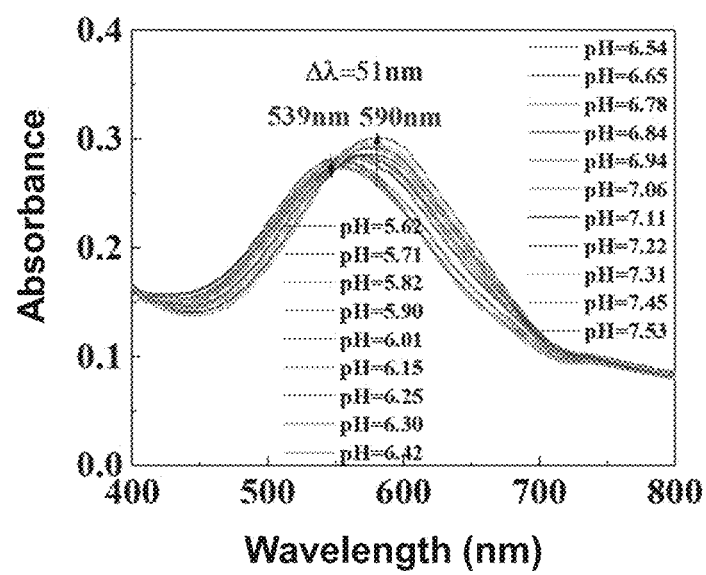
FIG. 34 is spectrum curves of the dye in Example 8 under different pH conditions (pH=5.62-7.53).

The spectral curves of the dye in Example 8 under different pH conditions (pH=4.01-6.51) are in FIG. 34. It can be seen from FIG. 34 that when the pH value of the solution is 6.30, the solution is red, and the maximum absorption wavelength of the solution is 539 nm; and when the pH value of the solution is 7.06, the solution is green, and the maximum absorption wavelength is 590 nm, which represents that the maximum absorption wavelength of the solution changes by 51 nm within 0.76 pH units of the dye, and represents that the chromotropic precision of the dye is relatively high.

Figure 35:
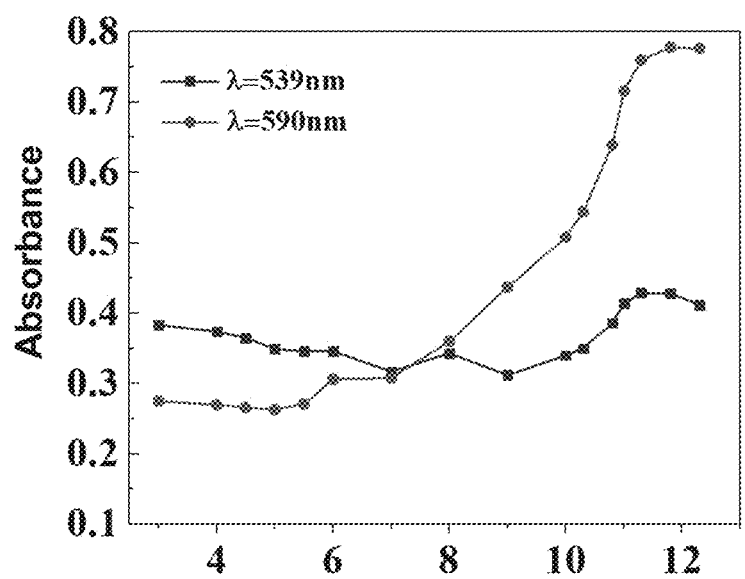
FIG. 35 illustrates a variation of an absorbance at a maximum absorption wavelength of a solution with a pH value before and after color changing of the dye in Example 8.
Figure 36:
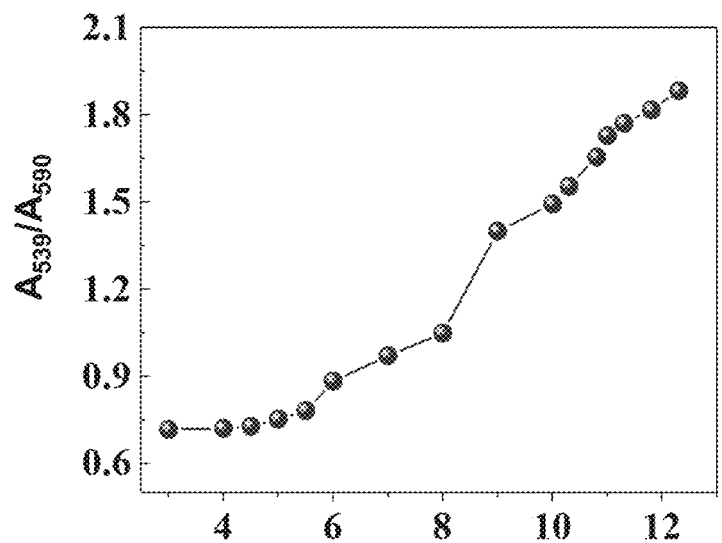
FIG. 36 illustrates a variation of an absorbance ratio of a solution with a pH value before and after color changing of the dye in Example 8.

A variation of an absorbance and an absorbance ratio of the absorbance at the maximum absorption wavelength with the pH value before and after color changing of the dye is in FIG. 35 and FIG. 36. It can be seen from FIG. 35 and FIG. 36 that the pH value at the color-changing isoelectric point (absorbance value of the solution when the color is changed) of the solution is 6.84.

Example 9 Dyeing the Cotton Fabrics Using Reactive Dyes

A preparation method of color-changingcotton fabric (140 g/m2, pure cotton bleached knitted fabric) comprises:
1. Printing color paste formula: 40 g/L of dye, 60 g/L of raw paste (sodium alginate aqueous solution with a mass concentration of 4%), 15 g/L of anti-dyeing salt S, 60 g/L of urea, 25 g/L of sodium carbonate, and adding water to make up 1000 g;
2. Printing process: printing→pre-baking (100° C., 4 min)→steaming (105° C., 6 min)→cold water washing→soaping (98° C., 10 min)→reduction cleaning (85° C., 15 min)→hot water washing (80° C.)→cold water washing→drying.

The cotton fabric obtained in Example 9 was soaked in sweat simulation solutions with different pH values (as in Table 5) for performance testing. The test results are as follows in Table 6 and FIGS. 37-40.

TABLE 5

Sweat simulation solutions with different pH values

| Component | Acid sweat simulation solution | Alkaline sweat simulation solution |
|---|---|---|
| L-histidine hydrochloride monohydrate | 0.5 g/L | 0.5 g/L |
| Sodium chloride | 5 g/L | 5 g/L |
| Sodium dihydrogen phosphate dihydrate | 2.2 g/L | — |
| Disodium hydrogen phosphate dihydrate | — | 2.5 g/L |
| 0.1 mol/L sodium hydroxide solution | Regulating pH value to 5.5 | Regulating pH value to 8.0 |

TABLE 6

Performance test of printed cotton fabric

| Indicator | | Color fixation rate K/S | Water fastness/ F % | Rubbing fastness/level Dry | Rubbing fastness/level Wet | Fastness to sunlight/ level |
|---|---|---|---|---|---|---|
| Dye of Example 7 | Acid sweat simulation solution | 10.69 | 50.23 | 4 | 4 | 3~4 | 3~4 |
| | Alkaline sweat simulation solution | 12.37 | | 4 | 4 | 3~4 | 3~4 |
| Dye of Example 8 | Acid sweat simulation solution | 15.18 | 55.36 | 4 | 4 | 4 | 4 |
| | Alkaline sweat simulation solution | 13.41 | | 4 | 4 | 4 | 4 |

It can be seen from Table 6 that the color fixation rates of the printed cotton fabric prepared by the dye in Example 7 and the dye in Example 8 all reached more than 50%, and the color fastness to washing, rubbing and sunlight all reached level 3-4 or above.

Figure 37:
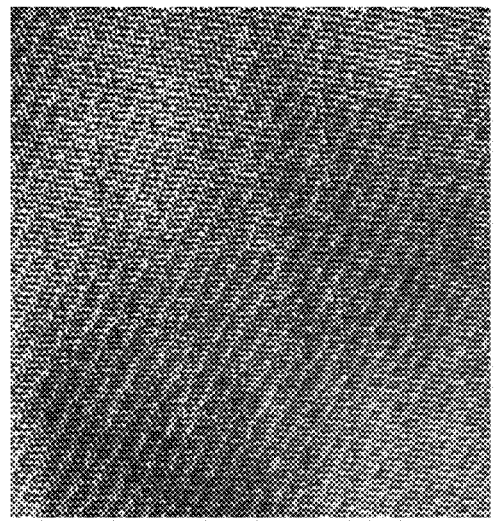
FIG. 37 illustrates a photograph of a printed cotton fabric using the dye in Example 7 under an acidic condition (pH=5.5).
Figure 38:
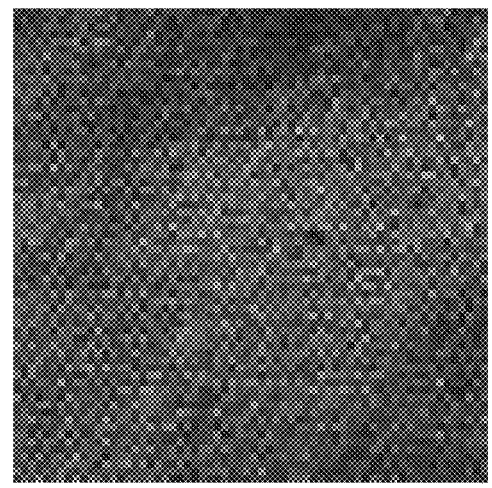
FIG. 38 illustrates a photograph of a printed cotton fabric using the dye in Example 7 under an alkaline condition (pH=8.0).

It can be seen from FIGS. 37-38 that the printed cotton fabric prepared with the dye in Example 7 is blue under an acid sweat condition, and green under an alkaline sweat condition, which can be applied to human sweat detection.

Figure 39:
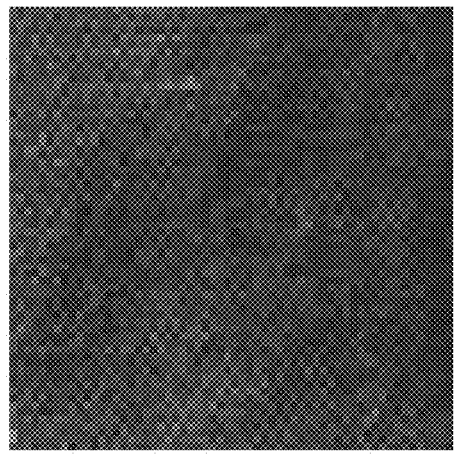
FIG. 39 illustrates a photograph of a printed cotton fabric using the dye in Example 8 under an acidic condition (pH=5.5).
Figure 40:
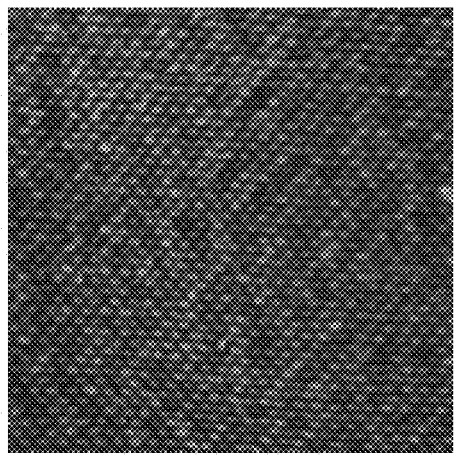
FIG. 40 illustrates a photograph of a printed cotton fabric using the dye in Example 8 under an alkaline condition (pH=8.0).

It can be seen from FIGS. 39-40 that the printed cotton fabric prepared with the dye in Example 8 is red under an acid sweat condition, and blue under an alkali sweat condition, which can be applied to human sweat detection.

Comparative Example 9

A preparation method of a dye comprises:

1. Primary Condensation Reaction Being the Same as 1 of Example 7

2. Secondary Condensation Reaction Being the Same with 2 of Example 7

3. Diazotization-Coupling Reaction (1) adding 18.45 g of 98% (w/w) sulfuric acid solution into a 250 mL three-necked flask, slowly adding 4.14 g (0.02 mol) of 2,6-dichloro-4-nitroaniline, and stirring for 1 h below 50° C. to fully dissolve it, slowly adding 6.99 g (0.022 mol) of 40% (w/w) nitrosylsulfuric acid solution dropwise below 0° C., and reacting for 4 h;

(2) after the reaction is finished, adding sulfamic acid to eliminate excess nitrous acid to obtain a heterocyclic primary arylamine diazo salt;

(3) dissolving 0.01 mol 7.22 g of the secondary condensation product in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting a reaction endpoint using H acid (1-amino-8-hydroxy-3,6-sodium naphthalenedisulfonic acid); and (4) after the reaction is finished, obtaining the pH chromotropic dye after salting out, suction filtration, ethanol washing and drying.

Figure 49:
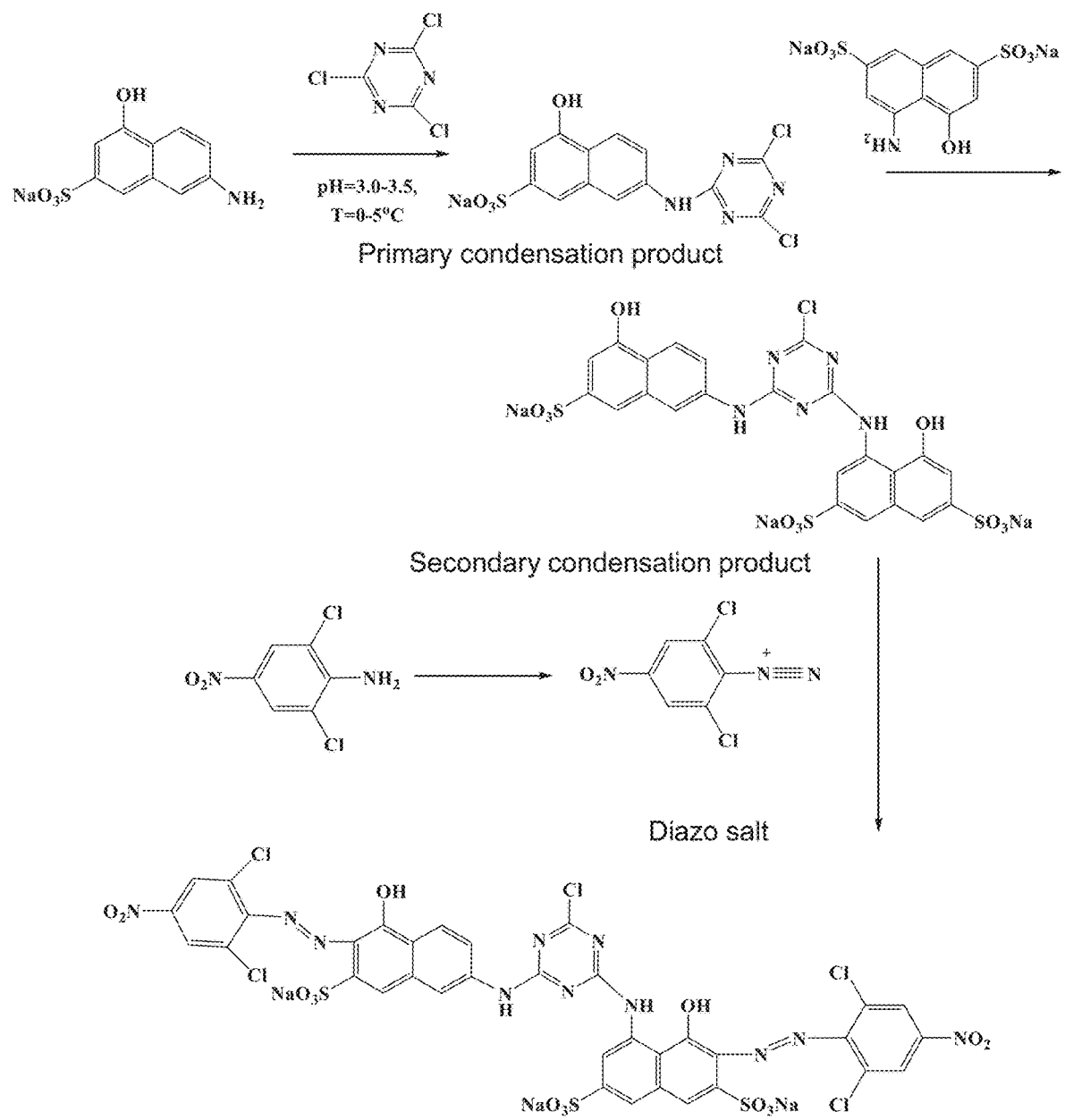
FIG. 49 illustrates a synthetic pathway of the reactive dye of Comparative Example 9.

The synthetic pathway of the dye is shown in FIG. 49. The structural formula of the obtained dye is as follows:

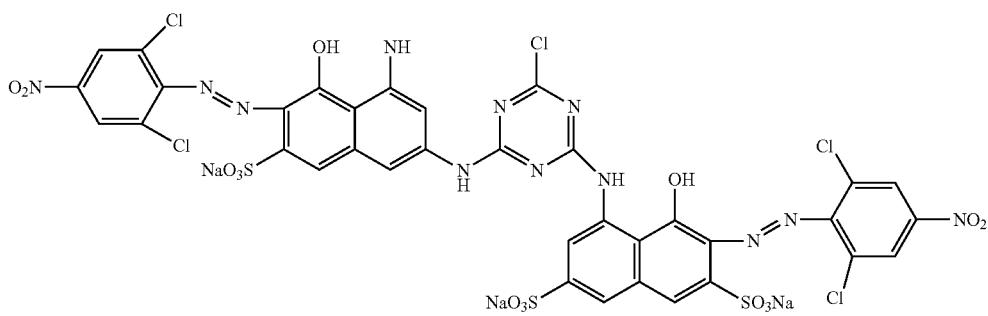

The dye prepared in Comparative Example 9 was printed on the cotton fabric according to the method in Example 9, and the color fixation rate of the dye on the cotton fabric was only 26.37%.

Comparative Example 10

A preparation method of a dye comprises:
1. Primary Condensation Reaction
(1) adding 3.74 g (0.02 mol) of cyanuric chloride and 0.19 g of sodium butylnaphthalene sulfonate into 15 g of ice-water mixture, and fully pulping for 1 h at 0-5° C. to obtain a cyanuric chloride solution;

(2) adding 4.78 g (0.02 mol) of 2-amino-5-naphthol-7-sulfonic acid into 15 g of water, regulating the pH to 6.0-6.5 using sodium carbonate, and fully dissolving to obtain a 2-amino-5-naphthol-7-sodium sulfonate solution;
(3) then mixing the 2-amino-5-naphthol-7-sodium sulfonate solution with the cyanuric chloride solution, regulating the pH to 3.0-3.5 using a saturated sodium bicarbonate solution, continuing the reaction at 0-5° C., and maintaining the pH value of the reaction solution at 3.0-3.5 using a sodium carbonate solution;
(4) detecting a reaction endpoint using an amino reagent to obtain a primary condensation solution;
(5) regulating the pH value of the primary condensation solution to 1.5 using acetic acid, and then adding a certain amount of potassium chloride to precipitate solid powder (a mass ratio of potassium chloride to the primary condensation solution was 0.3:1); and
(6) dispersing the precipitated solid powder in absolute ethanol, filtering, and freeze-drying to obtain a primary condensation product.

2. Secondary Condensation Reaction
(1) dissolving 9.44 g (0.02 mol) of the primary condensation product in 20 mL of water to prepare an aqueous solution of the primary condensation product;
(2) adding 4.78 g (0.02 mol) of 2-amino-5-naphthol-7-sulfonic acid into 15 g of water to obtain a 2-amino-5-naphthol-7-sulfonic acid solution;
(3) then slowly adding the 2-amino-5-naphthol-7-sulfonic acid solution into the aqueous solution of the primary condensation product, increasing the temperature to 30-35° C., regulating the pH to 4.5-5.0 using the saturated sodium bicarbonate solution, continuing the reaction at 30-35° C., and maintaining the pH of the reaction solution at 4.5-5.0 using the sodium carbonate solution;
(4) detecting the reaction endpoint using the amino reagent to obtain a secondary condensation solution;
(5) regulating the pH of the secondary condensation solution to 2.0 using acetic acid, and then adding a certain amount of potassium chloride to precipitate solid powder (a mass ratio of potassium chloride to the secondary condensation solution was 0.3:1); and
(6) dispersing the precipitated solid powder in absolute ethanol, filtering, and freeze-drying to obtain a secondary condensation product.

3. Diazotization-Coupling Reaction
(1) adding 50 g of 49% (w/w) sulfuric acid solution into a 250 mL three-necked flask, slowly adding 4.38 g (0.02 mol) of 2-amino-5,6-dichlorobenzothiazole, and stirring for 1 h below 50° C. to fully dissolving it;
(2) slowly adding 6.99 g (0.022 mol) of 40% (w/w) nitrosylsulfuric acid solution dropwise below 0-5° C., and reacting for 4 h;
(3) after the reaction was finished, adding sulfamic acid to eliminate excess nitrous acid to obtain a heterocyclic primary arylamine diazo salt;
(4) dissolving 5.98 g of the secondary condensation product (0.01 mol) in 20 mL of water, reducing the temperature to 10-15° C., and slowly adding the prepared heterocyclic primary arylamine diazo salt, continuing the reaction for 2 h at 10-15° C., regulating the pH to 6, continuing the reaction, and detecting the reaction endpoint using H acid (1-amino-8-hydroxy-3,6-sodium naphthalenedisulfonic acid); and
(5) after the reaction was finished, obtaining the pH chromotropic dye after salting out, suction filtration, ethanol washing and drying.

Figure 50:
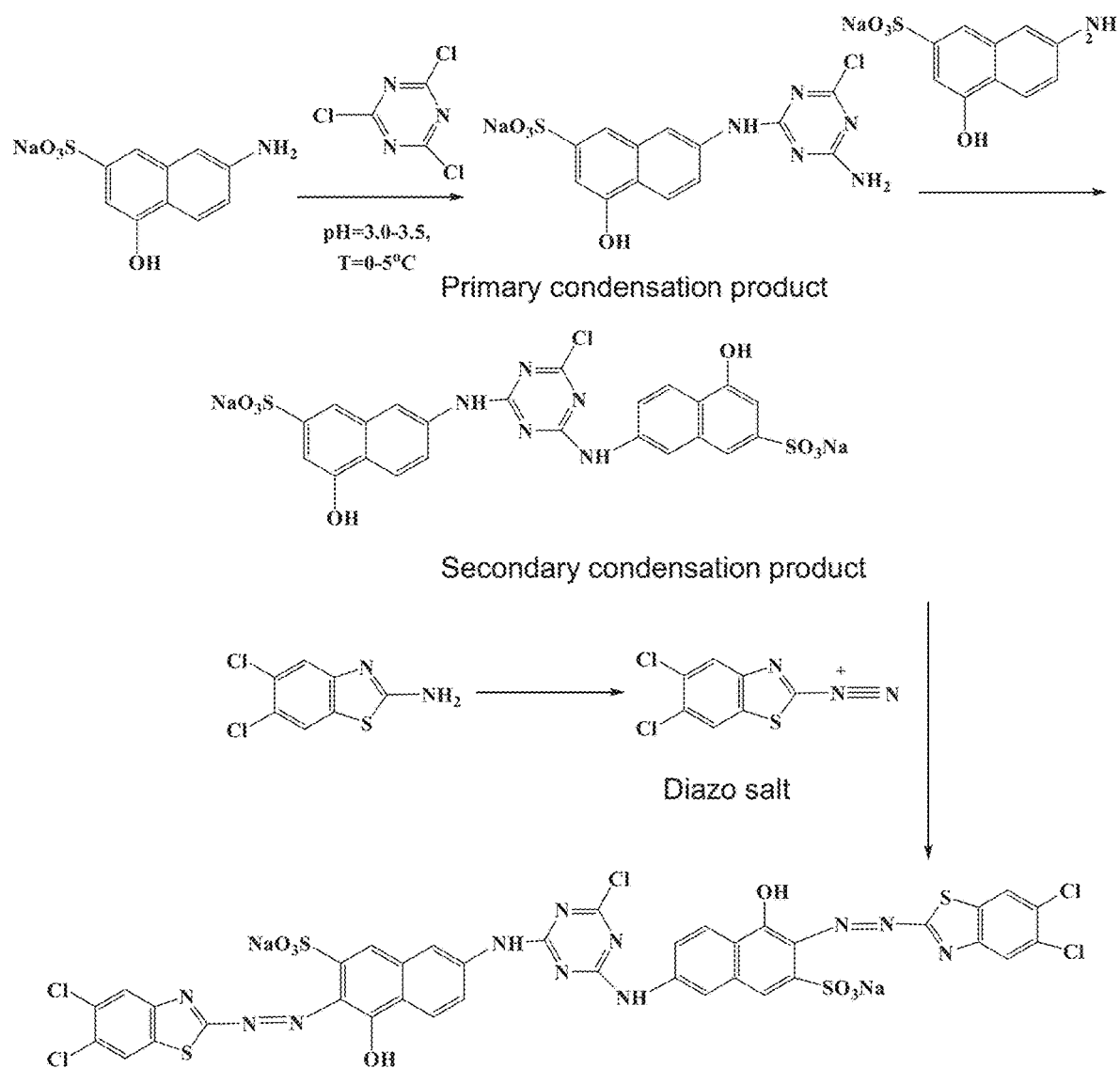
FIG. 50 illustrates a synthetic pathway of the reactive dye of Comparative Example 10.

The synthetic pathway of the dye is shown in FIG. 50. The structural formula of the obtained dye is as follows:

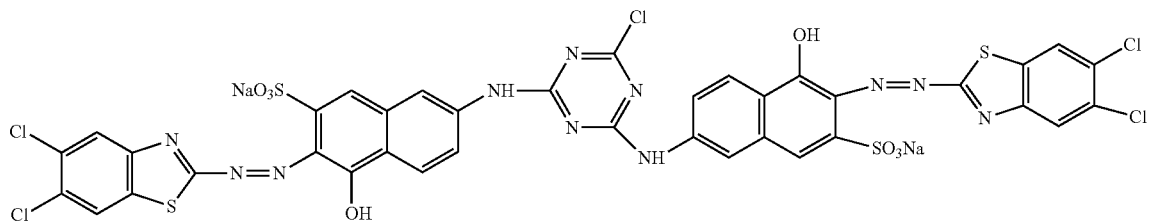

The dye prepared in Comparative Example 9 was printed on the cotton fabric according to the method in Example 9, and the color fixation rate of the dye on the cotton fabric was only 41.43%.

The basic concept has been described above. Obviously, for those skilled in the art, the above detailed disclosure is only an example, and does not constitute a limitation to the present disclosure. Although not expressly stated here, those skilled in the art may make various modifications, improvements and corrections to the present disclosure. Such modifications, improvements and corrections are suggested in this disclosure, so such modifications, improvements and corrections still belong to the spirit and scope of the exemplary embodiments of the present disclosure.

Meanwhile, the present disclosure uses specific words to describe the embodiments of the present disclosure. For example, "one embodiment", "an embodiment", and/or "some embodiments" refer to a certain feature, structure or characteristic related to at least one embodiment of the present disclosure. Therefore, it should be emphasized and noted that references to "one embodiment" or "an embodiment" or "an alternative embodiment" two or more times in different places in the present disclosure do not necessarily refer to the same embodiment. In addition, certain features, structures or characteristics in one or more embodiments of the present disclosure may be properly combined.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of ±20%. Accordingly, in some embodiments, the numerical parameters used in the disclosure and claims are approximations that can vary depending upon the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A pH-sensitive color-changing reactive dye having a double-luminescent structure, represented by formula:

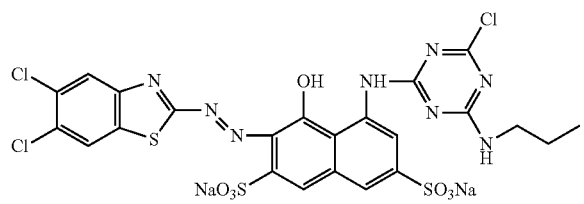

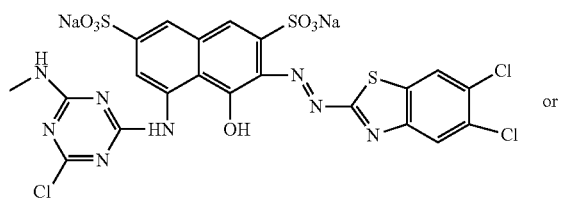

or

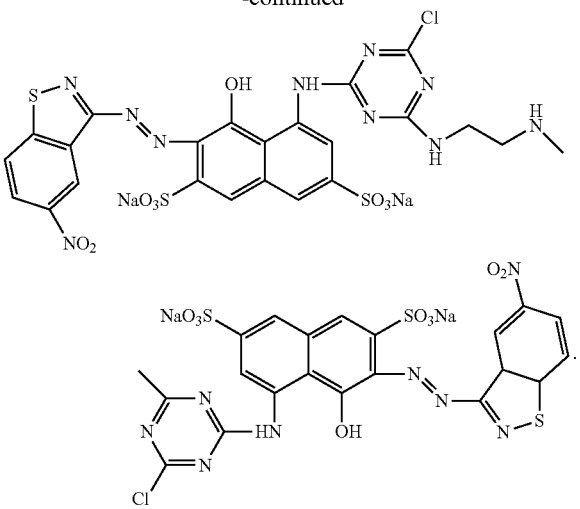

2. A preparation method of the pH-sensitive color-changing reactive dye having a double-luminescent structure of claim 1, comprising:
   (i) primary condensation reaction
   adding cyanuric chloride and sodium butylnaphthalene sulfonate into ice-water mixture and pulping at 0° C.-5° C. to obtain a cyanuric chloride solution;
   adding a parent compound of the reactive dye into water and adjusting pH to 6.0-6.5 to obtain a parent compound solution of the dye compound;
   mixing the parent compound solution with the cyanuric chloride solution, adjusting and maintaining pH to 3.0-3.5 with a sodium carbonate solution, continuously reacting at 0° C.-5° C., and detecting a reaction end point by adopting an amino reagent to obtain a primary condensation solution, wherein the parent compound of the reactive dye is 1-amino-8-hydroxy-3,6-naphthalenedisulfonic acid; and
   regulating pH of the primary condensation solution to 1.5 with acetic acid, then adding potassium chloride to precipitate solid powder, dispersing the precipitated solid powder in absolute ethanol, filtering, and freeze-drying to obtain a primary condensation product;
   (ii) secondary condensation reaction
   dissolving the primary condensation product in water to obtain an aqueous solution of the primary condensation product;
   mixing the aqueous solution of the primary condensation product with ethylenediamine, wherein the pH of the ethylenediamine is 9, increasing temperature to 30° C.-35° C., regulating and maintaining pH to 4.5-5.0 with the sodium carbonate solution, continuing the reaction at 30° C.-35° C., and detecting a reaction end point by adopting the amino reagent to obtain a secondary condensation solution;
   regulating pH of the secondary condensation solution to 2.0 with acetic acid, and then adding potassium chloride to precipitate solid powder; and
   dispersing the precipitated solid powder in absolute ethanol, filtering, and freeze-drying to obtain a secondary condensation product;
   (iii) diazotization-coupling reaction
   dissolving a heterocyclic primary arylamine derivative in acid, adding a diazotization reagent to react at 0° C.-5° C. for 3 h-4 h, and after the reaction is finished, eliminating excess nitrous acid to obtain a heterocyclic primary arylamine diazonium salt;

dissolving the secondary condensation product in water, reducing the temperature of the solution to 10° C.-15°C, slowly adding the heterocyclic primary arylamine diazo salt to react for 1 h-3 h, adjusting pH to 6, and detecting a reaction end point by adopting 1-amino-8-hydroxy-3,6-naphthalenedisulfonic acid; and after the reaction is finished, obtaining the reactive dye after salting out, suction filtration, washing with ethanol and drying.

3. The preparation method of claim 2, wherein the heterocyclic primary arylamine derivative in (iii) is formula 1 or 2:

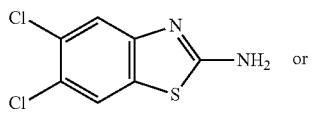

formula 1

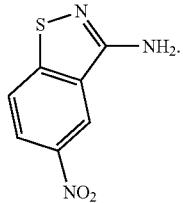

formula 2

4. The preparation method of claim 2, wherein a molar ratio of the secondary condensation solution to the heterocyclic primary arylamine diazo salt in is 1:2.

5. The preparation method of claim 2, wherein a mass ratio of the cyanuric chloride, the sodium butylnaphthalene sulfonate and the ice-water mixture in (i) is (3.5-4.0):(0.1-0.3):15.

6. A sweat detection sensor employing the pH-sensitive color-changing reactive dye having a double-luminescent structure of claim 1.

7. The preparation method of claim 2, wherein a molar ratio of the aqueous solution of the primary condensation product to the ethylenediamine in (ii) is 2:1.

* * * * *